(12) United States Patent
Shankar et al.

(10) Patent No.: US 11,319,544 B2
(45) Date of Patent: *May 3, 2022

(54) EXPRESSION CONSTRUCTS AND METHODS OF GENETICALLY ENGINEERING METHYLOTROPHIC YEAST

(71) Applicant: Impossible Foods Inc., Redwood City, CA (US)

(72) Inventors: Smita Shankar, Millbrae, CA (US); Martin Andrew Hoyt, San Francisco, CA (US)

(73) Assignee: Impossible Foods Inc., Redwood City, CA (US)

(*) Notice: Subject to any disclaimer, the term of this patent is extended or adjusted under 35 U.S.C. 154(b) by 629 days.

This patent is subject to a terminal disclaimer.

(21) Appl. No.: 16/123,121

(22) Filed: Sep. 6, 2018

(65) Prior Publication Data

US 2018/0371469 A1    Dec. 27, 2018

Related U.S. Application Data

(63) Continuation of application No. 15/678,342, filed on Aug. 16, 2017, now Pat. No. 10,273,492, which is a continuation of application No. 15/678,891, filed on Aug. 16, 2017, now Pat. No. 9,938,327, which is a continuation of application No. PCT/US2016/031797, filed on May 11, 2016.

(60) Provisional application No. 62/313,491, filed on Mar. 25, 2016, provisional application No. 62/236,506, filed on Oct. 2, 2015, provisional application No. 62/222,388, filed on Sep. 23, 2015, provisional application No. 62/220,366, filed on Sep. 18, 2015, provisional application No. 62/203,052, filed on Aug. 10, 2015, provisional application No. 62/185,921, filed on Jun. 29, 2015, provisional application No. 62/183,074, filed on Jun. 22, 2015, provisional application No. 62/159,899, filed on May 11, 2015.

(51) Int. Cl.
| | |
|---|---|
| *C12N 15/81* | (2006.01) |
| *C07K 14/39* | (2006.01) |
| *C07K 14/415* | (2006.01) |
| *C07K 14/805* | (2006.01) |
| *C12N 1/16* | (2006.01) |
| *C12N 15/63* | (2006.01) |

(52) U.S. Cl.
CPC ............ *C12N 15/815* (2013.01); *C07K 14/39* (2013.01); *C07K 14/415* (2013.01); *C07K 14/805* (2013.01); *C12N 1/16* (2013.01); *C12N 15/635* (2013.01); *C12N 15/81* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,886,753 A | 12/1989 | Marcker | |
| 4,965,188 A | 10/1990 | Mullis et al. | |
| 5,204,253 A | 4/1993 | Sanford et al. | |
| 5,538,800 A | 7/1996 | Jin et al. | |
| 5,753,465 A | 5/1998 | Chien et al. | |
| 5,824,511 A | 10/1998 | Mattoon et al. | |
| 6,013,863 A | 1/2000 | Lundquist et al. | |
| 6,261,827 B1 | 7/2001 | Elrod | |
| 6,329,571 B1 | 12/2001 | Hiei | |
| 8,021,695 B2 | 9/2011 | Gruber | |
| 8,236,528 B2 | 8/2012 | Takagi et al. | |
| 9,085,766 B2 | 7/2015 | Crane et al. | |
| 9,938,326 B2 | 4/2018 | Akeda et al. | |
| 9,938,327 B2 | 4/2018 | Shankar et al. | |
| 10,273,492 B2 | 4/2019 | Shankar | |
| 10,689,656 B2 | 6/2020 | Shankar et al. | |
| 2002/0194643 A1 | 12/2002 | Merot et al. | |
| 2007/0031832 A1 | 2/2007 | Watt | |
| 2008/0016675 A1 | 6/2008 | Bron et al. | |
| 2011/0287467 A1 | 11/2011 | Crane et al. | |
| 2013/0164850 A1 | 6/2013 | Sourdive | |
| 2015/0299716 A1 | 10/2015 | Zhou | |
| 2017/0188612 A1 | 7/2017 | Varadan | |
| 2017/0349637 A1 | 12/2017 | Shankar | |
| 2017/0349906 A1 | 12/2017 | Shankar et al. | |
| 2018/0127764 A1 | 5/2018 | Shankar et al. | |
| 2020/0340000 A1 | 10/2020 | Roy-Chaudhuri et al. | |
| 2021/0070842 A1 | 3/2021 | Fraser et al. | |

FOREIGN PATENT DOCUMENTS

| | | |
|---|---|---|
| EP | 2058398 | 5/2009 |
| EP | 2669375 | 12/2013 |
| JP | A-10-42873 | 2/1998 |
| JP | A-2008-17733 | 1/2008 |
| JP | A 2008017774 | 1/2008 |

(Continued)

OTHER PUBLICATIONS

Yurimoto et al., "Methanol-inducible gene expression and heterologous protein production in the methylotrophic yeast *Candida boidinii*" 53 Biotechnology and Applied Biochemistry 85-92 (Year: 2009).*
U.S. Appl. No. 62/835,338, filed Apr. 17, 2019, Hoyt et al.
EP Extended European Search Report in European Appln. No. 20157598-2, dated Aug. 26, 2020, 18 pages.
[No Author Listed] Impossible Foods Inc. "GRAS Notification for Soybean Leghemoglobin Protein Derived from Pichia Pastoris." GRAS notice 000737, Retrieved from internet <URL:https://www.fda.gov/downloads/Food/IngredientsPackagingLabeling/GRAS/NoticeInventory/default.htm, 1063 pages, Oct. 2, 2017.

(Continued)

*Primary Examiner* — Nancy J Leith
(74) *Attorney, Agent, or Firm* — Fish & Richardson P.C.

(57) ABSTRACT

Methods and materials for genetically engineering methylotrophic yeast are provided.

29 Claims, 11 Drawing Sheets

Specification includes a Sequence Listing.

(56) References Cited

FOREIGN PATENT DOCUMENTS

| | | |
|---|---|---|
| JP | A-2009-505657 | 2/2009 |
| WO | WO 1998/012913 | 4/1998 |
| WO | WO 2004/057946 | 7/2004 |
| WO | WO 2004/099405 | 11/2004 |
| WO | WO 2008090211 | 7/2008 |
| WO | WO 2009/009142 | 1/2009 |
| WO | WO 2012/083424 | 6/2012 |
| WO | WO 2013/010042 | 1/2013 |
| WO | WO 2014/008729 | 1/2014 |
| WO | WO 2014/110532 | 7/2014 |
| WO | WO 2014/110539 | 7/2014 |
| WO | WO 2015/153666 | 10/2015 |
| WO | 2016183163 | 11/2016 |
| WO | WO 2018102656 | 6/2018 |
| WO | WO 2018102721 | 6/2018 |

OTHER PUBLICATIONS

Chenna et al., "Multiple sequence alignment with the Clustal series of programs" Nucleic Acids Res., 31(13):3497-500 (2003).

Chiruvolu et al., "Recombinant protein production in an alcohol oxidase-defective strain of Pichia pastoris in fedbatch fermentations" Enzyme Microb. Technol., 21: 277-83 (1997).

Cregg et al, "Recombinant protein expression in Pichia pastoris," Molecular Biotechnology, 16:23-52 (2000).

Dayhoff et al., "A Model of Evolutionary Change in Proteins," Atlas of Protein Sequence and Structure, 5: 345-352 (1978).

GenBank Accession No. AAA33980, "leghemoglobin [Glycine max]," Apr. 1993, 1 page.

GenBank Accession No. AB365355, "Candida boidinii TRM1 gene for Zn(II)2Cys6-type transcription factor Trm1, complete cds," dated Jan. 24, 2008, 3 pages.

GenBank Accession No. AB548760, "Candida boidinii TRM2 gene for C2H2-type transcription factor Trm2, complete cds," dated May 14, 2010, 3 pages.

GenBank Accession No. ABD57365, "methanol expression regulator I [Komagataella pastoris]," dated Mar. 4, 2006, 2 pages.

GenBank Accession No. AEOI02000005, bases 858873 to 862352, "Ogataea parapolymorpha DL-1 chr3, whole genome shotgun sequence," dated Dec. 3, 2013, 186 pages.

GenBank Accession No. BAF99700, "Zn(II)2Cys6-type transcription factor Trm1 [Candida boidinii]," dated Jan. 23, 2008, 2 pagges.

GenBank Accession No. BAJ07608, "C2H2-type transcription factor Trm2 [Candida boidinii]," dated May 13, 2010, 2 pages.

GenBank Accession No. DQ395124, "Pichia pastoris methanol expression regulator I gene, complete cds," dated Mar. 4, 2006, 2 pages.

GenBank Accession No. ESX01253, "Regulatory protein ADR1 [Ogataea parapolymorpha DL-1]," dated Dec. 2, 2013, 2 pages.

GenBank Accession No. FJ752551, "Pichia pastoris dihydroxyacetone synthase 1 (DAS1) gene, complete cds" dated Mar. 21, 2009, 2 pages.

GenBank Accession No. X02425, "Hansenula polymorpha MOX gene for methanol oxidase" dated Apr. 20, 1993, 3 pages.

GenBank Accession No. YSAAOD1A, "Candida boidinii methanol oxidase (AOD1) gene, complete cds," dated Apr. 27, 1993, 2 pages.

Hargrove et al., "Characterization of recombinant soybean leghemoglobin a and apolar distal histidine mutants" J Mol. Biol. 266, 1032-1042 (1997).

Inan & Meagher, "Non-repressing carbon sources for alcohol oxidase (AOX1) promoter of Pichia pastoris" J. Biosci. Bioeng., 92:585-9 (2001).

International Preliminary Report on Patentability in International Application No. PCT/US2016/031797, dated Nov. 14, 2017, 7 pages.

International Search Report and Written Opinion in International Application No. PCT/US2014/055227, dated Mar. 20, 2015, 20 pages.

Jokipii-Lukkari et al., "Intrinsic non-symbiotic and truncated haemoglobins and heterologous Vitreoscilla haemoglobin expression in plants," Journal of Experimental Botany, 60(2):409-422 (Jan. 2009).

Kranthi et al., "Identification of Mxr1p-binding sites in the promoters of genes encoding dihydroxyacetone synthase and peroxin 8 of the methylotrophic yeast Pichia pastoris" Yeast, 27:705-11 (2010).

Liachko & Dunham, "An autonomously replicating sequence for use in a wide range of budding yeasts" FEMS Yeast Res., 14:364-7 (2014).

Lin-Cereghino et al., "Mxr1p, a key regulator of the methanol utilization pathway and peroxisomal genes in Pichia pastoris," Molecular and Cellular Biology, 26:883-897 (Feb. 2006).

Lloyd et al., "Targeted mutagenesis using zinc-finger nucleases in Arabidopsis" Proc. Natl. Acad. Sci. USA, 102:2232-2237 (2005).

Londer et al. "Production and preliminary characterization of a recombiant triheme cytochrom c(7) from Geobatcher sulfurreducens in Escherichia coli." Biochem Biophy Act 1 1554(3): 202-211 (2002).

Lutz et al., "A guide to choosing vectors for transformation of the plastid genome of higher plants" Plant Physiol. 145: 1201-1210 (2007).

Miele et al., "A GATA-type transcription factor regulates expression of the high-affinity iron uptake system in the methylotrophic yeast Pichia pastoris" Arch. Biochem. Biophys., 465: 172-9 (2007).

Nakagawa et al., "Alcohol oxidase hybrid oligomers formed in vivo and in vitro" Yeast, 15: 1223-30 (1999).

Qu et al., "Ectopic expression of the cotton non-symbiotic hemoglobin gene GhHb1 triggers defense responses and increases disease tolerance in Arabidopsis," Plant Cell Physiol., 47:1058-1068 (2006).

Raymond et al., "Development of the methylotrophic yeast Pichia methanolica for the expression of the 65 kilodalton isoform of human glutamate decarboxylase" Yeast, 14: 11-23 (1998).

Richards et al., "Construction of a GFP-BAR plasmid and its use for switchgrass transformation" Plant Cell. Rep. 20:48-20 54 (2001).

Sievers et al., "The Primary Structure of Soybean (Glycine max) Leghemoglobin c*," Acta Chemica Scandinavico B, 32:380-386 (1978).

Sinagawa-Garcia et al., "Next generation synthetic vectors for transformation of the plastid genome of higher plants" Plant Afol Biol 70: 487-498 (2009).

Somleva et al., "Agrobacterium-Mediated Genetic Transformation of Switchgrass" Crop Sci. 42:2080-2087 (2002).

Supplementary European Search Report in International Application No. EP 14844701.4, dated Jan. 27, 2017, 7 pages.

Tanaka and Tanaka, "Tetrapyrrole biosynthesis in higher plants" Annu. Rev. Plant Biol. 58: 321-46 (2007).

Tovkach et al., "A toolbox and procedural notes for characterizing novel zinc finger nucleases for genome editing in plant cells" Plant J, 57: 747-757 25 (2009).

Townsend et al., "High-frequency modification of plant genes using engineered zinc-finger nucleases" Nature 459: 442-445 (2009).

UniprotKB Accession No. P02236, "Leghemoglobin C2," dated Nov. 1, 1988, 9 pages.

Wu et al., "Efficient production of a functional single-chain antidigoxin antibody via an engineered Bacillus subtilis expression-secretion system" Bio/Technology (NY) 11(1): 71-76 (1993) (abstract only).

Xie and Yang, "RNA-guided genome editing in plants using a CRISPR-Cas system" Mal. Plant 6: 1975-1983 (2013).

Zhang et al., "Transcription activator-like effector nucleases enable efficient plant genome engineering" Plant Physiology 161: 20-27 (2013).

Krainer et al., "Optimizing cofactor availability for the production of recombinant heme peroxidase in Pichia pastoris", Microbial Cell Factories, vol. 14, No. 1, Jan. 13, 2015.

Liu et al., "Balanced globin protein expression and heme biosynthesis improve production of human hemoglobin in Saccharomyces cerevisiae", Metabolic Engineering, vol. 21, pp. 9-16, 2014.

Fraser et al., "Safety Evaluation of Soy Leghemoglobin Protein Preparation Derived From Pichia pastoris , Intended for Use as a Flavor Catalyst in Plant-Based Meat", International Journal of Toxicology, vol. 37, No. 3, Apr. 11, 2018, pp. 241-262.

(56) References Cited

OTHER PUBLICATIONS

Proulx et al., "Iron Bioavailability of Hemoglobin from Soy Root Nodules Using a Caco-2 Cell Culture Model", J Agric Food Chem, vol. 54, pp. 1518-1522, 2006.

Liu et al., "Developing *Bacillus* spp. as a cell factory for production of microbial enzymes and industrially important biochemicals in the context of systems and synthetic biology," Jul. 2013, 6113-6127, 97(14), Applied microbiology and biotechnology, Germany.

Nguyen et al., "Expression vectors for the rapid purification of recombinant proteins in Bacillus subtilis," Aug. 2007, 89-93, 55(2), Current microbiology, Germany.

Vasileuskaya et al., "Mg-protoporphyrin IX and heme control HEMA, the gene encoding the first specific step of tetrapyrrole biosynthesis, in Chlamydomonas reinhardtii," Eukaryotic cell, Oct. 1, 2005, 4(10):1620-1628, Freiburg, Germany.

Dailey et al, "Examination of mitochondrial protein targeting of haem synthetic enzymes: in vivo identification of three functional haem-responsive motifs in 5-aminolaevulinate synthase" Biochem J., 2005, 386(Pt2):381-386.

GenBank Accession No. AJ313360.1, "Hansenula polymorpha partial ORF1 DNA and MOX gene promoter region," dated Jul. 25, 2016, 2 pages.

GenBank Accession No. E06147.1, "Promoter of Candida alcohol oxidase gene," dated Nov. 4, 2005, 2 pages.

GenBank Accession No. KJ755994.1, "Komagataella pastoris strain GS115 FLD1 gene, promoter region and 5' UTR," dated Jul. 30, 2014, 1 page.

GenBank Accession No. NM_173881.2, "Bos taurus myoglobin (MB), mRNA," dated Feb. 23, 2019, 2 pages.

GenBank Accession No. U96967.1, "Pichia pastoris strain NRRL Y-11430 alcohol oxidase (AOX1) gene, complete cds," dated Oct. 30, 2001, 2 pages.

GenBank Accession No. X79871.1, "P.pastoris AOX2 gene, promoter region," dated Jul. 26, 2016, 2 pages.

González-Domínguez et al., "Haem Regulation of the Mitochondrial Import of the Kluyveromyces Lactis 5-aminolaevulinate Synthase: An Organelle Approach," Yeast, 2001, 18(1):41-48.

Goodfellow et al., "The solution structure and heme binding of the presequence of murine 5-aminolevulinate synthase," FEBS Letters, 2001, 404(2):325-331.

International Search Report and Written Opinion in PCT Appln. No. PCT/US2020/029946, dated Jul. 14, 2020, 12 pages.

Kubota, et al., "Novel Mechanisms for Heme-dependent Degradation of ALAS1 Protein as a Component of Negative Feedback Regulation of Heme Biosynthesis," J. Biol. Chem., 2016, 291(39):20516-20529.

Mense and Zhang, "Heme: a versatile signaling molecule controlling the activities of diverse regulators ranging from transcription factors to MAP kinases," Cell Res., 2006, 16:681-692.

Munakata et al., "Role of the Heme Regulatory Motif in the Heme-Mediated Inhibition of Mitochondrial Import of 5-aminolevulinate Synthase," J. Biochem., 2004, 136(2):233-238.

Sudhamsu et al., "Co-expression of ferrochelatase allows for complete heme incorporation into recombinant proteins produced in *E. coli*," Protein Expr. Purif., 2010, 73(1):78-82.

UniParc Accession No. UPI0001A4D18B, retrieved from URL <https://www.uniprot.org/uniparc/UPI0001A4D18B?sort=score>, available on or before Sep. 2018, 3 pages.

GenBank Accession No. AF066054.1, "Pichia pastoris formaldehyde dehydrogenase (FLD1) gene, complete cds," dated Sep. 17, 1998, 2 pages.

GenBank Accesston No. AY288296.1, "Pichia pastoris 3-phosphoglycerate kinase (PGK1) gene, complete cds," dated Jul. 22, 2005, 2 pages.

GenBank Accession No. CAY70887.1, "Hypothetical protein PAS_chr3_0836 [Komagataella phaffii GS115]," dated Feb. 27, 2015, 2 pages.

GenBank Accession No. U62648.1, "Pichia pastoris glyceraldehyde-3-phosphate dehydrogenase (GAP) gene, complete cds," dated Mar. 7, 1997, 2 pages.

GenBank Accession No. XM_002490678.1, "Komagataella phaffii GS 115 Hypothetical protein (PAS_chr1-4_0586), partial Mrna," dated Jul. 22, 2009, 2 pages.

Hoffman, et al., "Identification of rate-limiting steps in yeast heme biosynthesis," Biochem. Biophys. Res. Commun., 2003, 310(4):1247-1253.

Mitrophanov, et al., "Positive autoregulation shapes response timing and intensity in two component signal transduction systems," J. Mol. Biol., 2010, 401(4):671-680.

Mitrophanov, et al., "Positive feedback cellular control systems," Bioessays, 2008, 30(6):542-555.

PCT International Search Report and Written Opinion in International Appln. No. PCT/US2016/031797, dated Sep. 20, 2016, 9 pages.

Sasano, et al., "Trm2p-dependent depression is essential for methanol-specific gene activation in the methylotrophic yeast *Candid boidinii*," FEMS Yeast Res., 2010, 10:535-544.

Supplementary European Search Report and Opinion in EP Appln. No. EP 16793420.7, dated Aug. 29, 2018,8 pages.

Dailey, "Enzymes of heme biosynthesis," JBIC Journal of Biological Inorganic Chemistry, Aug. 1997, 2(4):411-417.

International Preliminary Report on Patentability in International Appln. No. PCT/US2020/029946, dated Nov. 4, 2021, 7 pages.

Pereira et al., "Conserved regulation of the Hansenula polymorpha MOX promoter in *Saccharomyces cerevisiae* reveals insights in the transcriptional activation by AdrIp," European journal of biochemistry, May 1996, 238 (1):181-191.

Sasano et al., "Trm1p, a Zn (II) 2Cys6-type transcription factor, is a master regulator of methanol-specific gene activation in the methylotrophic yeast *Candida boidinii*," Eukaryotic Cell, Mar. 2008, 7(3):527-536.

Vogl et al., "Regulation of Pichia pastoris promoters and its consequences for protein production," New biotechnology, May 25, 2013, 30(4):385-404.

Wang et al., "Mit1 transcription factor mediates methanol signaling and regulates the alcohol oxidase 1 (AOX1) promoter in Pichia pastoris," Journal of Biological Chemistry, Mar. 18, 2016, 291(12):6245-6261.

\* cited by examiner

| MXY Strain | Yield on glycerol co-feed | Yield on dextrose co-feed |
|---|---|---|
| 183 | 1X | 1X |
| 207 | 4.4X | 4.4X |
| 291 | 5.8X | 5.8X |
| 306 | 5.8X | 5.8X |
| 330 | 6.9X | 6.9X |
| 333 | 5.8X | 5.8X |
| 338 | 6.9X | 6.9X |

Figure 11

EXPRESSION CONSTRUCTS AND METHODS OF GENETICALLY ENGINEERING METHYLOTROPHIC YEAST

CLAIM OF PRIORITY

This application is a Continuation of U.S. patent application Ser. No. 15/678,342 filed Aug. 16, 2017, which is a Continuation of U.S. patent application Ser. No. 15/678,891 filed Aug. 16, 2017, which is a Continuation of PCT/US2016/031797 filed May 11, 2016, which claims the benefit of priority to U.S. Provisional Application No. 62/313,491 filed Mar. 25, 2016, U.S. Provisional Application No. 62/236,506 filed Oct. 2, 2015, U.S. Provisional Application No. 62/222,388 filed Sep. 23, 2015, U.S. Provisional Application No. 62/220,366 filed Sep. 18, 2015, U.S. Provisional Application No. 62/203,052 filed Aug. 10, 2015, U.S. Provisional Application No. 62/185,921 filed Jun. 29, 2015, U.S. Provisional Application No. 62/183,074 filed Jun. 22, 2015, and U.S. Provisional Application No. 62/159,899 filed May 11, 2015, the entire contents of which are hereby incorporated by reference.

STATEMENT REGARDING SEQUENCE LISTING

This application contains a Sequence Listing that has been submitted electronically as an ASCII text file named "SEQ". The ASCII text file, created on Sep. 5, 2018 is 44,992 bytes in size. The material in the ASCII text file is hereby incorporated by reference in its entirety. The sequence listing is being submitted electronically via EFS-Web herewith.

TECHNICAL FIELD

This disclosure generally relates to DNA constructs and methods of using such DNA constructs to genetically engineer methylotrophic yeast.

BACKGROUND

Methylotrophic yeast such as *Pichia pastoris* are commonly used for expression of recombinant proteins. Constructs that can be used to efficiently express one or more polypeptides in a methylotrophic yeast are provided herein.

SUMMARY

This disclosure describes the use of *P. pastoris* strains that overexpress the transcriptional activator, Mxr1, from the AOX1 promoter to increase expression of transgenes that also are expressed from the AOX1 promoter, which significantly improves the recombinant production of one or more proteins. In addition, expression of Mxr1 from the AOX1 promoter creates a positive feedback loop that allows for expression of other transgenes from the AOX1 promoter in the absence of methanol, the normally obligate inducer, when repressing carbon sources are depleted. Expression of Mxr1 results in a significant increase in the amount of protein produced.

In one aspect, a methylotrophic yeast cell is provided that includes a recombinant nucleic acid molecule. The recombinant nucleic acid molecule typically includes an exogenous nucleic acid encoding a transcriptional activator operably linked to at least one methanol-inducible promoter element. Representative methylotrophic yeast can be of the genus *Candida*, *Hansenula*, *Pichia* or *Toruplosis*. A representative methylotrophic yeast is *Pichia pastoris*.

In some embodiments, the recombinant nucleic acid molecule is stably integrated into the genome of the methylotrophic yeast cell. In some embodiments, the recombinant nucleic acid molecule is extrachromosomally expressed from a replication-competent plasmid.

In some embodiments, the exogenous nucleic acid encoding a transcriptional activator comprises a Mxr1 sequence from *Pichia pastoris*, a Adr1 sequence from *Hansenula polymorpha*, a Trm1 sequence from *Candida boidinii*, and a Trm2 sequence from *Candida boidinii*. A representative nucleic acid encoding a transcriptional activator is shown in DQ395124. A representative transcriptional activator has an amino acid sequence shown in ABD57365.

In some embodiments, the at least one methanol-inducible promoter element is an alcohol oxidase 1 (AOX1) promoter element from *Pichia pastoris*, an AOD1 promoter element from *Candida boidinii*, a MOX promoter element from *Hansenula polymorpha*, a MOD1 promoter element from *Pichia methanolica*, a DHAS promoter element from *Pichia pastoris*, a FLD1 promoter element from *Pichia pastoris*, or a PEX8 promoter element from *Pichia pastoris*.

In some embodiments, the methylotrophic yeast cell further includes a nucleic acid molecule that includes at least one heterologous nucleic acid encoding a polypeptide operably linked to at least one methanol-inducible promoter element. In some embodiments, the at least one heterologous nucleic acid encodes one or more polypeptides involved in the biosynthesis of an iron co-factor such as heme (e.g., ALA synthase, ALA dehydratase, porphogilinogen deaminase, UPG III synthase, UPG III decarboxylase, CPG oxidase, PPG oxidase, and/or ferrochelatase). In some embodiments, one or more of the polypeptides involved in the biosynthesis of the iron co-factor are linked to at least one methanol-inducible promoter element.

In another aspect, a method for expressing a heterologous polypeptide in a cell is provided. Such a method typically includes providing a methylotrophic yeast cell as described herein; introducing a recombinant nucleic acid molecule into methylotrophic yeast cell, the recombinant nucleic acid molecule comprising at least one heterologous nucleic acid encoding a polypeptide operably linked to at least one *Pichia pastoris* alcohol oxidase 1 (AOX1) promoter element; and culturing the cell under conditions suitable for expression of the recombinant nucleic acid molecule, thereby expressing the heterologous polypeptide.

In some embodiments, the conditions under which the cells are cultured includes the addition of iron or a pharmaceutically or metabolically acceptable salt thereof. In some embodiments, the introducing step includes a technique such as transduction, electroporation, biolistic particle delivery, or chemical transformation. In some embodiments, the culturing step includes culturing the cell in the present of methanol.

In another aspect, a recombinant organism is provided that includes a transcriptional activator operably linked to the promoter it activates. In some embodiments, a recombinant organism is provided that expresses a polypeptide operably linked to the promoter. In yet another aspect, a method of expressing a polypeptide from an inducible promoter without addition of an inducer is provided as described herein.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 11 is a summary table showing relative yields of strains described herein when grown in the presence of methanol with glycerol or methanol with glucose in 2 L fermenter tanks.

DETAILED DESCRIPTION

Figure 1:
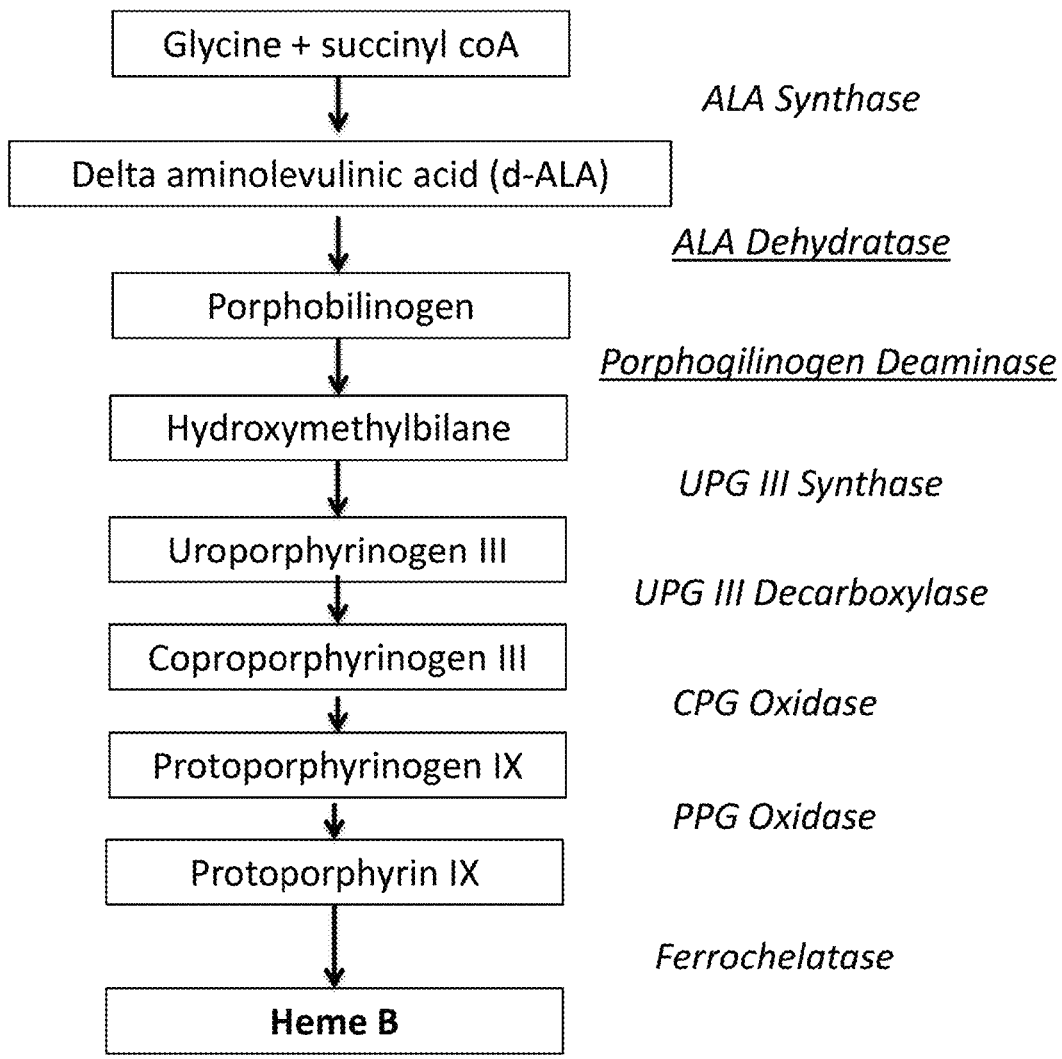
FIG. 1 is a schematic depicting the steps involved in the heme biosynthesis pathway.

Nucleic acid constructs are provided herein that allow for genetically engineering a cell to increase the recombinant expression of a polypeptide. In some embodiments, nucleic acid constructs are provided herein that allow for genetically engineering a cell to increase the recombinant expression of a polypeptide from an inducible promoter in the absence of the inducing molecule. Without being bound by any particular mechanism, the methods described herein create a positive feedback loop where the low level native expression of a transcriptional activator induces a promoter that is operably linked to a transcriptional activator. This leads to an increased expression of the transcriptional activator as well as one or more target polypeptides that are operably linked to the same inducible promoter.

Nucleic acid constructs are provided herein that allow for genetically engineering a methylotrophic yeast cell. While the methods are exemplified herein using a *Pichia* species (i.e., *P. pastoris*), other species of the *Pichia* genus can be used or species from any of the *Candida*, *Hansenula*, *Pichia* and *Torulopsis* genera.

Genetically engineering a methylotrophic yeast cell typically includes introducing a recombinant nucleic acid molecule into the cell. As described herein, a recombinant nucleic acid molecule typically includes an exogenous nucleic acid that encodes a transcriptional activator operably linked to at least one inducible promoter element.

Recombinant nucleic acid molecules used in the methods described herein are typically DNA, but RNA molecules can be used under the appropriate circumstances. As used herein, "exogenous" refers to any nucleic acid sequence that is introduced into the genome of a cell from an external source, where the external source can be the same or a different organism or a nucleic acid generated synthetically. For example, an exogenous nucleic acid can be a nucleic acid from one microorganism (e.g., one genus or species of methylotrophic yeast) that is introduced into a different genus or species of methylotrophic yeast, however, an exogenous nucleic acid also can be a nucleic acid from a methylotrophic yeast that is introduced recombinantly into a methylotrophic yeast as an additional copy despite the presence of a corresponding native nucleic acid sequence. For example, *P. pastoris* contains an endogenous nucleic acid encoding a Mxr1 transcriptional activator; an additional *P. pastoris* Mxr1 nucleic acid (e.g., introduced recombinantly into *P. pastoris*) or modifying the endogenous *P. pastoris* Mxr1 nucleic acid is considered exogenous.

Transcriptional activators, and nucleic acids encoding transcriptional activators (e.g., exogenous nucleic acids encoding transcriptional activators), are known in the art. For example, a transcriptional activator from *Pichia pastoris* is the Mxr1 sequence, but suitable transcriptional activators also can be found in *Hansenula polymorpha* (the Adr1 sequence; see, for example, GenBank Accession No. AEOI02000005, bases 858873 to 862352, for the nucleic acid sequence and GenBank Accession No. ESX01253 for the amino acid sequence) and *Candida boidinii* (the Trm1 sequence; see, for example, GenBank Accession No. AB365355 for the nucleic acid sequence and GenBank Accession No. BAF99700 for the amino acid sequence; the Trm2 sequence; see, for example, GenBank Accession No. AB548760 for the nucleic acid sequence and GenBank Accession No. BAJ07608 for the amino acid sequence). A representative *P. pastoris* Mxr1 nucleic acid sequence can be found, for example, in GenBank Accession No. DQ395124, while a representative *P. pastoris* Mxr1 polypeptide sequence can be found, for example, in GenBank Accession No. ABD57365.

Transcriptional activators such as Mxr1 may be normally expressed at low levels. Therefore, it is desirable to place the exogenous nucleic acid (i.e., the transcriptional activator) under control of a promoter that is inducible. As used herein, "operably linked" means that a promoter or other expression element(s) are positioned relative to a nucleic acid coding sequence in such a way as to direct or regulate expression of the nucleic acid (e.g., in-frame).

There are a number of inducible promoters that can be used when genetically engineering methylotrophic yeast. For example, a methanol-inducible promoter, or a promoter element therefrom, can be used. Methanol inducible promoters are known in the art. For example, a commonly used methanol-inducible promoter from *P. pastoris* is the promoter, or a portion thereof, from the alcohol oxidase 1 (AOX1) gene, which is strongly transcribed in response to methanol. Other methanol-inducible promoters, or promoter elements therefrom, however, can be used, including, without limitation, the alcohol oxidase (AOD1) promoter from *Candida boidinii* (see, for example, GenBank Accession No. YSAAOD1A), the alcohol oxidase (MOX) promoter from *Hansenula polymorpha* (see, for example, GenBank Accession No. X02425), the MOD1 or MOD2 promoter from *Pichia methanolica* (see, for example, Raymond et al., 1998, Yeast, 14:11-23; and Nakagawa et al., 1999, Yeast, 15:1223-30), the DHAS promoter from *P. pastoris* (see, for example, GenBank Accession No. FJ752551) or a promoter element therefrom, the formaldehyde dehydrogenase (FLD1) promoter from *Pichia pastoris* (see, for example, GenBank Accession No. AF066054), or the PEX8 promoter from *P. pastoris* (see, for example, Kranthi et al., 2010, Yeast, 27:705-11). In some embodiments, the transcriptional activator is a Mit1 sequence from *Pichia pastoris* (see, for example, GenBank Accession No. CAY70887). All of these promoters are known to be induced by methanol.

A skilled artisan would understand that the recombinant nucleic acid molecule described herein can be stably integrated into the genome of the methylotrophic yeast cell, or can be extrachromosomally expressed from a replication-competent plasmid. Methods of achieving both are well known and routinely used in the art.

As demonstrated herein, the methanol-regulated transcriptional activators in *Pichia* can bind to the AOX1 promoter and act cooperatively with Mxr1 to activate transcription from the AOX1 promoter. In some embodiments, two methanol-regulated transcriptional activators (e.g., Mxr1 and Mit1) can be operably linked to a methanol inducible promoter element.

A strain that includes a recombinant nucleic acid molecule as described herein can be used to regulate (e.g., overexpress) a second recombinant nucleic acid molecule in the methylotrophic yeast cell. A second recombinant nucleic acid molecule can include, for example, one or more heterologous nucleic acids encoding one or more polypeptides of interest. Similar to the exogenous nucleic acid encoding the transcriptional activator, a heterologous nucleic acid refers to any nucleic acid sequence that is not native to the genome or in the genome of an organism (e.g., a heterologous nucleic acid can be a nucleic acid from one microorganism (e.g., one genus or species of methylotrophic yeast) that is introduced into a different genus or species of methylotrophic yeast).

Simply by way of example, heterologous nucleic acids encoding the one or more polypeptides of interest can be the nucleic acids involved in the biosynthesis of a heme-co-factor. Exemplified herein are nucleic acids encoding the 8 different enzymes involved in heme biosynthesis as determined and annotated from the sequence of the *Pichia pastoris* genome. For example, heterologous nucleic acids encoding ALA synthase, ALA dehydratase, porphobilinogen deaminase, UPG III synthase, UPG III decarboxylase, CPG oxidase, PPG oxidase, and ferrochelatase can be expressed in the methylotrophic yeast strains described herein. For genetically engineering methylotrophic yeast to contain more than one heterologous nucleic acids (e.g., transgenes), a combination of methanol-inducible and constitutive promoters, or elements therefrom, can be combined to further increase the expression of such nucleic acids.

Previous studies in *Saccharomyces cerevisiae* identified ALA dehydratase and porphobilinogen deaminase as rate limiting enzymes in heme biosynthesis (see, for example, Hoffman et al., 2003, Biochem. Biophys. Res. Commun., 310(4):1247-53). However, heterologous expression of individual heme enzymes in *P. pastoris* from the glyceraldehyde-3-phosphate dehydrogenase (GAP) promoter failed to overcome limitations associated with the expression of a recombinant protein containing a heme co-factor (see Krainer et al., 2015, Microb. Cell Fact., 13; 14:4). As described herein, highly efficient expression of a recombinant heme containing protein in *P. pastoris* was achieved by co-expressing the entire heme biosynthetic pathway from methanol-inducible promoters, although it would be appreciated that one or more of the genes involved in the heme biosynthetic pathway could be expressed from one or more constitutive promoters.

In addition to the enzymes involved in iron-co-factor biosynthesis, it would be understood that a nucleic acid encoding a member of the globin family of proteins (PF00042 in the Pfam database) including plant hemoglobins can be present. In the Examples herein, a nucleic acid encoding soybean leghemoglobin (LegH) is present. LegH is a protein that binds to the iron co-factor, heme, which results in a characteristic absorption at 415 nm and a distinct red color. The LegH protein (also known as LGB2) is naturally found in root nodules of soybean (see, for example, UniprotKB Accession No. P02236), and the nucleic acid sequence used herein was codon optimized for expression in *P. pastoris*. See, for example, WO 2014/110539 and WO 2014/110532.

Alternatively, a heterologous nucleic acid encoding a polypeptide of interest can be, for example and without limitation, a dehydrin, a phytase, a protease, a catalase, a lipase, a peroxidase, an amylase, a transglutaminase, an oxidoreductase, a transferase, a hydrolase, a lyase, an isomerase, a ligase, or an antibody against any such polypeptides. In other embodiments, a heterologous nucleic acid can encode one or more enzymes involved in the pathway for production of small molecules, such as ethanol, lactic acid, butanol, adipic acid, or succinic acid.

Similar to the exogenous nucleic acid encoding the transcriptional activator, the heterologous nucleic acid encoding a polypeptide of interest can be operably linked to an inducible promoter element (e.g., a methanol-inducible promoter element), or the heterologous nucleic acid encoding a polypeptide of interest can be operably linked to a constitutive promoter or constitutive promoter element. Inducible promoters and elements therefrom are discussed above. Constitutive promoters and constitutive promoter elements are known in the art. For example, a commonly used constitutive promoter from *P. pastoris* is the promoter, or a portion thereof, from the transcriptional elongation factor EF-1α gene (TEF1), which is strongly transcribed in a constitutive manner. Other constitutive promoters, or promoter elements therefrom, however, can be used, including, without limitation, the glyceraldehyde-3-phosphate dehydrogenase (GAPDH) promoter from *P. pastoris* (see, for example, GenBank Accession No. U62648.1), the promoter from the potential glycosyl phosphatidyl inositol (GPI)-anchored protein, GCW14p (PAS_chr1-4_0586), from *P. pastoris* (see, for example, GenBank Accession No. XM_002490678), or the promoter from the 3-phosphoglycerate kinase gene (PGK1) from *P pastoris* (see, for example, GenBank Accession No. AY288296).

Similar to the recombinant nucleic acid molecule described herein, the second recombinant nucleic acid molecule can be stably integrated into the genome of the methylotrophic yeast cell, or can be extrachromosomally expressed from a replication-competent plasmid.

It would be understood by the skilled artisan that a combination of inducible (e.g., methanol-inducible) and constitutive promoters (or promoter elements therefrom) can be combined to further increase the expression of any of the nucleic acids operably linked thereto.

It would be appreciated by a skilled artisan that a heterologous nucleic acid encoding a polypeptide of interest operably linked to a promoter element can be separate from the recombinant nucleic acid molecule described herein, or can be contiguous with the exogenous nucleic acid encoding a transcriptional activator operably linked to a promoter element contained within the recombinant nucleic acid molecule described herein. It also would be appreciated by a skilled artisan that, if the second nucleic acid molecule is contiguous with the recombinant nucleic acid molecule described herein, that a single promoter, or promoter element therefrom, can be used to drive transcription of both or all of the genes (e.g., the exogenous nucleic acid encoding the transcriptional activator as well as the one or more heterologous nucleic acids encoding the polypeptide(s) of interest).

Methods of introducing nucleic acids into methylotrophic yeast cells are known in the art, and include, without limitation, transduction, electroporation, biolistic particle delivery, and chemical transformation.

In addition, methods of culturing methylotrophic yeast cells are known in the art. See, for example, Pichia Protocols, *Methods In Molecular Biology*, 389, Cregg, Ed., 2007, $2^{nd}$ Ed., Humana Press, Inc. Under some circumstances, it may be desirable to introduce or add methanol to the culture media, although, as demonstrated herein, methanol is not required to obtain efficient expression at high levels of one or more polypeptides of interest. Under some circumstances (e.g., when one or more nucleic acids encoding enzyme(s) involved in an iron-co-factor biosynthesis are expressed), it may be desirable to supplement the culture media with iron or a pharmaceutically or metabolically acceptable (or GRAS) salt thereof.

*Pichia* strains are able to grow on methanol as the sole carbon source. Methanol utilization is initiated by the conversion of methanol to formaldehyde by the action of alcohol oxidase. The methylotrophic yeast, *Pichia pastoris*, contains two genes for alcohol oxidases, AOX1 and AOX2. Strains with reduced alcohol oxidase activity ("methanol utilization slow" or MutS strains) often produce more of a recombinant protein expressed from the AOX1 promoter than strains that do not have reduced alcohol oxidase activity. Strains mutated in both AOX genes and completely lacking alcohol oxidase activity cannot metabolize methanol, but can still be induced for expression from the AOX1 promoter by methanol. These strains retain the ability to use other carbon sources for growth, but still express heterologous proteins from the AOX1 promoter upon the addition of methanol. Because these strains do not metabolize methanol ("methanol utilization minus" or Mut– strains), much less methanol is required for induction of protein expression, and strains carrying these mutations avoid issues related to methanol feeding in large-scale fermentations. See, for example, Chiruvolu et al., 1997, Enzyme Microb. Technol., 21:277-83. It was determined herein that expression of LegH from the AOX1 promoter in Mut-strains greatly improved the LegH yield. Thus, a methylotrophic yeast having a mutation in both the AOX1 gene and the AOX2 gene can be used in the methods described herein.

The protein of interest, or a complex that includes one or more proteins of interest (e.g., heme-bound LegH, a dehydrin, a phytase, a protease a catalase, a lipase, a peroxidase, an amylase, a transglutaminase, an oxidoreductase, a transferase, a hydrolase, a lyase, an isomerase, a ligase, or an antibody) can be purified from the yeast cells. Methods of purifying polypeptides are known in the art. As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

As used herein, nucleic acids can include DNA and RNA, and includes nucleic acids that contain one or more nucleotide analogs or backbone modifications. A nucleic acid can be single stranded or double stranded, which usually depends upon its intended use. Also provided are nucleic acids and polypeptides that differ from a given sequence. Nucleic acids and polypeptides can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a given nucleic acid or polypeptide sequence.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule, thereby leading to changes in the amino acid sequence of the encoded polypeptide. For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5 (Suppl. 3):345-352), which provides frequency tables for amino acid substitutions), and a non-conservative substitution is one in which an amino acid residue is replaced with an amino acid residue that does not have a similar side chain. Nucleic acid and/or polypeptide sequences may be modified as described herein to improve one or more properties including, without limitation, increased expression (e.g., transcription and/or translation), tighter regulation, deregulation, loss of catabolite repression, modified specificity, secretion, thermostability, solvent stability, oxidative stability, protease resistance, catalytic activity, and/or color.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A construct or vector containing a nucleic acid (e.g., a nucleic acid that encodes a polypeptide) also is provided. Constructs or vectors, including expression constructs or vectors, are commercially available or can be produced by recombinant DNA techniques routine in the art. A construct or vector containing a nucleic acid can have expression elements operably linked to such a nucleic acid, and further can include sequences such as those encoding a selectable marker (e.g., an antibiotic resistance gene). A construct or vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as $E.$ $coli$, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Methods are described herein that can be used to generate a strain that lacks sequences for selection (i.e., that lacks a selectable marker). These methods include using a circular plasmid DNA vector and a linear DNA sequence; the circular plasmid DNA vector contains a selection marker and an origin of DNA replication (also known as an autonomously replicating sequence (ARS)), and the linear DNA sequence contains sequences for integration into the *Pichia* genome by homologous recombination. The linear DNA molecule additionally can include nucleic acid sequences encoding one or more proteins of interest such as, without limitation, heme-bound LegH, a dehydrin, a phytase, a protease a catalase, a lipase, a peroxidase, an amylase, a transglutaminase, an oxidoreductase, a transferase, a hydrolase, a lyase, an isomerase, a ligase, one or more enzymes involved in the pathway for production of small molecules, such as ethanol, lactic acid, butanol, adipic acid or succinic acid, or an antibody against any such proteins.

*Pichia* cells can be transformed with both DNA molecules and the transformants selected by the presence of the selectable marker on the circular plasmid. Transformants then can be screened for integration of the linear DNA molecule into the genome using, for example, PCR. Once transformants with the correct integration of the marker-free linear DNA molecule are identified, the cells can be grown in the absence of selection for the circular plasmid. Because the marker-bearing plasmid is not stably maintained in the absence of selection, the plasmid is lost, often very quickly, after selection is relaxed. The resulting strain carries the integrated linear DNA in the absence of heterologous sequences for selection. Therefore, this approach can be used to construct *Pichia* strains that lack a selectable marker (e.g., a heterologous selection marker) with little to no impact on recombinant protein yield.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

PART A. Materials and Methods

Example 1—Polymerase Chain Reaction

Genes of interest were amplified from genomic DNA or plasmid DNA templates using PHUSION® Hi-fidelity DNA polymerase (New England Biolabs). Briefly, 0.6 µM each of forward and reverse primers are incubated with 10-50 ng of template DNA and 400 µM of nucleotide mix in the presence of 1-2 U of PHUSION® DNA polymerase. The reaction conditions were as follows in Table 1:

TABLE 1

| Reaction Parameters | | | |
|---|---|---|---|
| 1 cycle | Initial Denaturation | 98° C. | 1 min |
| 25 cycles | Denaturation | 98° C. | 10 sec |
| | Annealing | | 20 sec |
| | Extension | 72° C. | 30 sec per kb |
| 1 cycle | Final Extension | 72° C. | 5 min |
| 1 cycle | Hold | 4° C. | Forever |

Example 2—Plasmid Construction by Ligation 50-100 ng of restriction enzyme digested plasmid and 3× molar excess of PCR amplified inserts were incubated in the presence of T4 DNA ligase (New England Biolabs). Ligation was carried out at 16° C. for greater than 2 hr. 2 µl of ligation reaction was transformed into DH10B electrocompetent *E. coli* cells

Example 3—Transformation into *E. coli* ElectroMax DH10B T1 Phage-Resistant Competent Cells 1.5-2 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV using a 1 mm gap cuvette (BioRad, Cat #165-2089); after a pulse 1 ml SOC was added to cells and cells were incubated at 37° C. for 1 h with shaking at 200 rpm. 10 μl of recovery mixture was plated on LB agar plates containing ampicillin at a concentration of 100 μg/ml. Plates were incubated overnight at 37° C.

Example 4—Linearization of Plasmid DNA for Transformation into *P. pastoris*

Plasmid DNA was digested with either PmeI restriction endonuclease (New England BioLabs, Cat #R0560L) in 1× CUTSMART® Buffer for 1-4 hours at 37° C. or SfiI restriction endonuclease in 1× CUTSMART® Buffer for 1-4 hours at 50° C. (New England BioLabs, Cat #R0123L). Linearized plasmid was gel purified from a 0.8% agarose gel using ZYMOCLEAN™ Gel DNA Recovery Kit (Zymo Research, Cat #D4002). DNA was eluted in 20 μl $H_2O$.

Example 5—Preparation of *P. pastoris* Transformation-Competent Cells

Selected strains of *P. pastoris* were grown to mid-exponential growth phase (~2 OD) in 25 ml YPD medium. Cells were collected by centrifugation at 930×g for 15 minutes. The cell pellet was resuspended in 2 ml of a solution of 80% YPD and 200 mM HEPES, pH 6.8. 75 μl of 1 M DTT was added. The resuspended cell pellet was mixed at 100 rpm at 30° C. for 25 minutes. A 40 ml volume of ice cold, sterile water was added to the suspension, and the cells were collected by centrifugation at 1125×g for 15 minutes and placed on ice. The cell pellet was resuspended in 40 ml ice cold water and collected as before for two additional wash steps. The cell pellet was then resuspended in 20 ml of ice cold 1 M sorbitol and collected by centrifugation as before. The final cell pellet was suspended in 0.3 ml ice cold, sterile sorbitol, aliquoted and frozen at −80° C.

Example 6—Transformation into *P. pastoris*

30-100 ng of linearized plasmid DNA was transformed into 30 μl of electrocompetent *P. pastoris* cells using a 1 mm gap GenePulser cuvette (BioRad) with a GenePulser (BioRad) set at 1.15 kV. 1 ml of YPD/1M sorbitol was added and mixed at a 1:1 ratio to the cells. The cells were allowed to recover for 3 h at 30° C. with shaking at 100 rpm. 100 μl of the recovery mixture was plated on a YPD plate containing the appropriate antibiotic, and the rest of the cells were plated on a YPD plate with the appropriate antibiotic. Plates were incubated at 30° C. for 48 hours. Primary transformation plates were streaked onto YPD plates with appropriate antibiotic, and plates were incubated for 48 h at 30° C. Individual clones were patched onto YPD plates with antibiotics and the patches were used to do colony PCR or gDNA prep to confirm integration into the chromosome and to grow the strains in shake flasks for further analysis.

Example 7—Growing Cultures in Shake Flasks for Production of LegH

A strain from a fresh patch was inoculated into growth media BMGY (BMY supplemented with 0.75% glycerol) and grown overnight at 30° C. with shaking at 200 rpm. The next day, expression of LegH was induced with methanol by diluting the ON culture with BMMY media (BMY+1% methanol) supplemented with 0.1 mM Ammonium Fe(III) citrate. The culture was grown to an OD600 of 0.5-0.7. Antifoam was added to a final concentration of 0.01%. The cultures were grown for 72 hours total; cultures were supplemented with methanol every 24 hours by adding 1/10 of shake flask volume of 10×BMMY media (BMY+10% methanol). Cells were harvested after 72 h of induced growth by centrifugation.

Example 8—Shake Flask Medium

BMY media was prepared by dissolving 10 g of yeast extract and 20 g soytone in 790 ml water. The mixture was sterilized by autoclaving, and cooled to room temperature. 100 ml 1 M Potassium Phosphate buffer (pH 6.0) and 100 ml 10× Yeast Nitrogen Base without amino acids (13.4 g of YNB powder per 100 mL; Sigma-Aldrich) was filter sterilized (0.2 μm pore size PES) and added to the media. No pH adjustment is required. Table 2 contains BMY media components.

TABLE 2

BMY Media Components

| Component | Amount, per 1 L |
|---|---|
| Yeast Extract | 10 g |
| Soy peptone (BD) | 20 g |
| Yeast Nitrogen Base without amino acids, 10X solution | 100 mL (results in 13.4 g/L in BMY) |
| 1M Potassium Phosphate Buffer, pH 6.0 | 100 mL |

The following components were dissolved in water, and autoclaved to sterilize (Table 3).

TABLE 3

Low-Osmolarity Medium for Shake Flask

| Component | Amount, g/L |
|---|---|
| Ammonium Sulfate | 15.7 |
| Potassium Phosphate Monobasic | 9.4 |
| Calcium Sulfate Dihydrate | 0.43 |
| Magnesium Sulfate Heptahydrate | 11.7 |
| Sodium Citrate Dihydrate | 1.13 |

Example 9—Fermentation Medium and Feeds

The components indicated below were dissolved and the volume adjusted with water (Table 4). The components were FCC food grade or equivalent. The medium was sterilized by autoclaving, by steaming in place, or with an equivalent.

TABLE 4

Low-Osmolarity Medium with 95 g/L Glycerol for Fermentation

| Component | Amount, g/L |
|---|---|
| Ammonium Sulfate | 15.7 |
| Potassium Phosphate Monobasic | 9.4 |
| Calcium Sulfate Dihydrate | 0.43 |
| Magnesium Sulfate Heptahydrate | 11.7 |
| Sodium Citrate Dihydrate | 1.13 |
| Glycerol, USP grade 99.7% | 95 |

After sterilization, the medium was allowed to cool down to room temperature, and the following in Table 5 was added:

TABLE 5

Additional Components

| Component | Amount, mL/L |
|---|---|
| Trace Metals PTM1 Solution | 2 |
| Vitamin Solution | 4 |
| Sigma 204 antifoam or equivalent | 1 |

Trace metals PTM1 solution is available as a powdered mix from Sunrise Science (Cat No. 4052-A-B-1L) (Table 6). Pouch A and pouch B were mixed in 950 mL water, and 5 mL sulfuric acid was added. Some precipitation is expected upon mixing; the mixture was filter sterilized (0.2 μm pore size PES) and stored at 4° C. in the dark.

TABLE 6

Vitamin solution recipe

| Component | Amount, g/L |
|---|---|
| biotin | 0.2 |
| calcium pantothenate | 1 |
| folic acid | 0.2 |
| inositol | 1 |
| niacin | 0.2 |
| p-aminobenzoic acid | 0.2 |
| Pyridoxine hydrochloride | 1 |
| riboflavin | 0.5 |
| thiamine hydrochloride | 1 |
| B12 | 0.1 |

Alternatively, trace metals PTM1 can be made as follows (Table 7):

TABLE 7

Trace metal PTM1

| Component | Amount |
|---|---|
| Cupric sulfate - 5H2O | 6.0 g |
| Sodium iodide | 0.08 g |
| Manganese sulfate - H2O | 3.0 g |
| Sodium molybdate - 2H2O | 0.2 g |
| Boric acid | 0.02 g |
| Cobalt chloride | 0.5 g |
| Zinc chloride | 0.5 g |
| Ferrous sulfate - 7H2O | 65.0 g |
| Biotin | 0.2 g |
| Sulfuric acid | 5.0 ml |
| Water | To a final volume of 1 L |

The components are mixed together, filter sterilized and stored at room temperature. The glycerol feed mix was prepared by mixing 17.5 g of AmberFerm 4000 into 320 mL water and stirring to dissolve. The water-Amberferm mixture was added to 850 g of glycerol and mixed well by vigorous stirring. The feed mix was sterilized by autoclaving. See Table 8 for recipe.

TABLE 8

Glycerol feed solution

| Component | Amount, g/L |
|---|---|
| USP grade glycerol | 850 |
| Water | 320 |
| Sensient AmberFerm4000 soy hydrolysate | 17.5 |

The methanol feed was made using 99-100% methanol supplemented with 12 mL/L of PTM1 solution.

Example 10 Protocol for Lab-Scale High Oxygen Transfer Fermentation

Seed Shake Flask Protocol

In a aseptic biosafety hood, low-osmolarity medium and BMY were mixed in a 9:1 low-osmo:BMY ratio. Glycerol, at a concentration of 12.5 g/L, was added to the medium. USP food grade glycerol/glycerin (99.7% purity in a 50% v/v (63% w/w) glycerol/water solution) was used and autoclaved to sterilize. Sigma 204 or an equivalent antifoam was added to the medium at a concentration of 0.25 mL/L. Glycerol seed vials were retrieved, sprayed outside with 70% IPA or ethanol and thawed inside a biosafety hood at room temperature for about 5 min. Baffled shake flasks were inoculated with glycerol seed vials; 1 mL of inoculum vial were used for every 1 L of shake flask medium. Cultures were grown at 30° C. for 24 hours with shaking (200 RPM with a 1" throw). A ratio of between 1:10 and 1:5 of actual medium volume:nominal shake flask volume was used. 2.8 L nominal volume flask with 250 to 500 mL of medium were routinely use with success. The OD at 600 nm was measured after 24 hours of growth; if the OD was 15 or higher, the culture was used to inoculate a fermenter. If the OD was less than 15, the culture was grown for 1-2 more hours before the OD was determined again. If an OD of 15 was not reached after 15 to 30 hours, the seed flask was considered to have failed.

Fermentation Protocol

The fermentation medium and feeds were prepared as described herein. The initial volume should be about 40% of the maximum fermenter volume, e.g., 4 L, if the maximum working volume of the fermenter is 10 L. This is because the process will approach the maximum working volume by the end of the fermentation. The fermenter is inoculated with shake flask seed at 10% inoculum-fermenter ratio, e.g. if 4 L of initial media are present in the fermenter, the fermenter is inoculated with about 0.4 L of shake flask seed. The total volume in the fermenter at this point is referred to T0 volume, e.g. 4.4 L in this representative example. Process controls include the following: 30° C. temperature; dissolved oxygen controlled by agitation-aeration cascade to maintain a 20% saturation set point; and pH controlled via addition of 28% $NH_4OH$, the set point will depend on the phase of the process.

Batchphase (from inoculation to depletion of glycerol, signaled by DO spike): Depending on the responsiveness of the PID control for dissolved oxygen, a strong DO spike or a fast drop in agitation-aeration rates or a combination of both may be observed when the cells deplete the glycerol present in the medium. Fed-batch phase is initiated when this occurs. The duration of the batch phase is approximately 20 hours, but up to 24 hours is considered acceptable. The pH set point is 5.0. The wet cell weight at the end of the batch phase will be approximately 220 g/L.

Fed-batch phase: glycerol feed is initiated to achieve 12-14 g/L/hr of neat glycerol based on T0 volume. The federate was maintained until approximately 350 g/L wet cell weight was reached, which should take about 7-10 hours. The pH set point is 5.0.

Transition phase: A sample is taken before beginning the transition phase. Methanol feed was initiated to achieve 1 g/L/hr of neat methanol, based on the T0 volume, until 1-2 g/L methanol concentration was reached in the fermentation broth. The methanol feed rate was adjusted during the remainder of fermentation so as to maintain a methanol concentration of 0.25-1 g/L in broth. Glycerol federate was reduced from 12-14 g/L/hr to 8-9 g/L/hr of neat glycerol, based on T0 volume, linearly over the course of 2 hours. Stepwise reduction in feed rate every 20 min would be acceptable as well. The pH set point was changed to 3.5, and the fermentation was allowed to naturally adjust to the new set point (i.e., with no addition of acid).

Production phase (from end of glycerol feed ramp-down to end of fermentation): The pH set point was 3.5. A methanol concentration of 0.25-1 g/L was maintained in the fermentation broth. The feed rate of the glycerol was maintained at 8-9 g/L/hr of neat glycerol, based on the T0 volume. Samples were taken approximately every 12 hours. Samples were spun at 4000 to 7000 RCF at 4° C., and the supernatant decanted. The supernatant was saved in a separate tube. Pellets and 3 samples of 5 mL of supernatants at each time point were frozen at −80° C. If a 15-20% DO during production is unable to be maintained, even at maximum aeration and agitation rates for the vessel, the glycerol feed rate can be lowered up to 5 g/L/hr of neat glycerol, based on the T0 volume. Fermentation ended 60 hours after inoculation. At 1000 L scale, the harvest process consisted of shutting down feeds and aeration, chilling the broth to 8° C., and concentrating the paste using a sharpless or disk stack centrifuge. Harvesting usually takes about 5-10 hours and does not incur a detectable loss of quality of the product. For lab scale, it is sufficient to collect, in addition to the 3×5 mL samples, an additional 50 mL sample at the end. Wet cell weight was >450 g/L, and spun pellets looked pink, as opposed to spun pellets from pre-induction samples, which looked more white. The color change of the broth from white to a more pronounced pink started following about 6-12 hours of induction.

Part B. Construction of Production Strains
Production Strain MXY0183

Example 11 Cloning Each Enzyme of Heme Biosynthesis Pathway into pGAN or pGAZ Integration Vector pGAN (with the nat selection marker) and pGAZ (with the ZEOCIN™ selection marker) were purchased from Biogrammatics, Inc (Carlsbad, Calif.). Each gene was placed under control of the AOX1 promoter, and the FDH terminator was placed immediately after the stop codon of each gene. The genes in the heme biosynthesis pathway were PCR amplified from wild type *P. pastoris* strain or subcloned from previous constructs.

The heme biosynthetic pathway, including the enzymes involved in the biosynthesis of heme, are shown in FIG. 1. The intermediates produced during the biosynthesis of heme are shown in the boxes, and the enzyme catalyzing each step is shown to the right. The rate limiting enzymatic steps, as shown in *S. cerevisiae*, are shown with underlining.

ALA synthase, ALA dehydratase, UPGIII synthase, UPGIII decarboxylase, CPG oxidase and PPG oxidase genes were PCR amplified with primers containing sites for recognition by the restriction endonuclease, BsaI (Table 9). Oligonucleotides were synthesized by ElimBiopharm.

TABLE 9

Primer Sequences

| Primer Designation | Gene | Sequence | SEQ ID NO: |
|---|---|---|---|
| Mx00187 | ALAsynth_F | GAGGGTCTCGGATGGAGTTTGTCGCCCGTC | 19 |
| Mx00188 | ALAsynth_R | GAGGGTCTCGATTACAATCTGACTCCTGATGAGG | 20 |
| Mx00189 | ALAdehyd_F | GAGGGTCTCGGATGGTGCATAAGGCTGAATACTTG | 21 |
| Mx00190 | ALAdehyd_R | GAGGGTCTCGATTATTCAGATAACCACTCCAGG | 22 |
| Mx00191 | UroporSynth_F | GAGGGTCTCGGATGCCAAAAGCCATTCTTCTGAAG | 23 |
| Mx00192 | UroporSynth_R | GAGGGTCTCGATTAGTGCACTTTTTGTATAGAC | 24 |
| Mx00193 | UroporDecarb_F | GAGGGTCTCGGATGAGTAGATTTCCAGAACTGAAG | 25 |
| Mx00194 | UroporDecarb_R | GAGGGTCTCGATTATTGAGATCCAATGCG | 26 |
| Mx00195 | CoproOx_F | GAGGGTCTCGGATGGCCATCGACTCTGATATC | 27 |
| Mx00196 | CoproOx_R | GAGGGTCTCGATTATACCCATTCAATAGGAT | 28 |

TABLE 9-continued

Primer Sequences

| Primer Designation | Gene | Sequence | SEQ ID NO: |
|---|---|---|---|
| Mx00197 | ProtoporOx_F | GAGGGTCTCGGATGCTGAAAAGTCTTGCACCAAA | 29 |
| Mx00198 | ProtoporOx_R | GAGGGTCTCGATTAAATGCCACTGAGGGTAGC | 30 |

PHUSION® High-Fidelity DNA Polymerase (New England BioLabs, Cat #M0530L) was used to amplify genes from genomic DNA. PCR products were obtained and purified using DNA Clean&Concentrator-5 (Cat #D4004) and DNA was eluted in 25 µl of H₂O. Vector DNA, pGAZ and pGAN, and PCR products were digested with BsaI (New England BioLabs, Cat #R0535S) in 50 µl reaction volume at 37° C.

Linearized vectors and digested PCR products were purified from 0.8% agarose gel using ZYMOCLEAN™ Gel DNA Recovery Kit (Zymo Research Cat #D4002). DNA was eluted in 20 µl H₂O. Ligation reactions were set up in 10 µl at 16° C. overnight using T4 DNA Ligase (New England BioLabs, Cat #M0202S).

PBD and ferrochelatase genes were subcloned from previously constructed plasmids: pJAZ_PBD was digested with BstBI(Bsp119I) (ThermoScientific, FD0124) and NotI (ThermoScientific, FD0596) in 1× Fast Digest buffer for 5 min at 37° C. pJAZ_Ferroch was digested with MfeI (MunI, ThermoScientific, FD0753) and NotI (ThermoScientific, FD0596) in 1× Fast Digest buffer for 5 min at 37° C.

Digested products were purified from 0.8% agarose gel using ZYMOCLEAN™ Gel DNA Recovery Kit (Zymo Research Cat #D4002). DNA was eluted in 20 µl H₂O.

Ligation reactions were set up in 10 µl reaction at 16° C. overnight using T4 DNA Ligase (New England BioLabs, Cat #M0202S).

1.5 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV; cells were incubated at 37° C. in 1 ml SOC for 1 h with shaking at 200 rpm. 10 µl of recovery mixture was plated on LB agar plates containing ampicillin at concentration 100 µg/ml. Plates were incubated overnight at 37° C. Colonies were screened by colony PCR for the presence of the insert. The sequences of the genes were confirmed. Strain designation and genetic constructs are in Table 10.

TABLE 10

Strain Designations and Genetic Constructs.

| Designation | Construct | Gene |
|---|---|---|
| pMx0308 | pGAN-ALAsynth | ALA synthase |
| pMx0309 | pGAN-ALAD | ALAD |
| pMx0310 | pGAN-UPGIIIsyn | Uroporphyrinogen synthase |
| pMx0311 | pGAN-UPGIIIdecarb | Uroporphyrinogen decarboxylase |
| pMx0312 | pGAN-CPGoxi | CPG oxidase |
| pMx0313 | pGAN-PPGoxi | Protoporphyrin oxidase |
| pMx0314 | pGAZ-ALAsyn | ALA synthase |
| pMx0315 | pGAZ-ALAD | ALAD |
| pMx0316 | pGAZ-UPGIIIsyn | Uroporphyrinogen synthase |
| pMx0317 | pGAZ-UPGIIIdecarboxilase | UPGIII decarboxylase |
| pMx0318 | pGAZ-PPGoxidase | PPG oxidase |
| pMx0319 | pGAZ-CPG oxidase | CPG oxidase |
| pMx0320 | pGAN-PBD | PBD |
| pMx0321 | pGAZ-PGC | PBD |
| pMx0322 | pGAZ-Fc | Ferrochelatase |
| pMx0323 | pGAN-Fc | Ferrochelatase |

Example 12—Assembling Heme Biosynthesis Genes on Plasmids for Integration into *P. pastoris* mutS Genome The whole cassette "promoter-gene-terminator" was PCR amplified with primers containing sites for restriction endonucleases to assemble plasmids for integration into the *Pichia* genome.

Assembling Paox1_UPS_FDHterm-Paox1_UPD_FDHterm-Paox1_CPO_FDH term. on pGAN plasmid (pMx327)

pGAN-CPGoxidase (pMx312) was used as a vector to clone the UPS and UPD cassettes. UPG III synthase cassette was PCR amplified from pMx310 with primers to AOX1 promoter/FDH1 terminator containing NheI and SphI recognition sites for restriction endonucleases correspondingly (Table 11):

TABLE 11

Primer Sequences

| Primer Designation | Recognition Sites | Sequence | SEQ ID NO: |
|---|---|---|---|
| Mx00399 | NheI-pAOX1-F | CAA TCG CTA GCA TCC AAC ATC AAC AGA CGA AAG G | 31 |
| Mx00401 | SphI-FDH1-R | GGA TAG CAT GCA CCT TAT CAA GAT AGC TAG AAA TAG AAA TGG | 32 |

UPG III decarboxylase cassette was PCR amplified from pMx311 with primers to AOX1 promoter/FDH1 terminator containing SphI and AgeI recognition sites for restriction endonucleases correspondingly (Table 12):

TABLE 12

Primer Sequences

| Primer Designation | Recognition Sites | Sequence | SEQ ID NO: |
|---|---|---|---|
| Mx00402 | SphI-pAOX1I-F | CAA TAG CAT GCA ACA TCC AAA GAC GAA AGG TTG AAT G | 33 |
| Mx00404 | AgeI-FDH1-R | CAT GGT ACC GGT ACC TTA TCA AGA TAG CTA GAA ATA GAA ATG G | 34 |

PHUSION® High-Fidelity DNA Polymerase (New England BioLabs, Cat #M0530L) was used to amplify DNA from plasmids.

Obtained PCR products were purified using DNA Clean&Concentrator-5 (Zymo Research, Cat #D4004) and DNA was eluted in 25 µl of H$_2$O.

pGAN-CPGoxidase (pMx312) designated as a vector was digested in 1× CUTSMART® Buffer with NheI-HF (New England BioLabs, Cat #R3131S) and AgeI-HF (New England BioLabs, Cat #R3552S) over night at 37° C.

UPG III synthase cassette PCR product was digested in 1× CUTSMART® Buffer with NheI-HF (New England BioLabs, Cat #R3131S) and SphI-HF (New England BioLabs, Cat #R3182S) over night at 37° C.

UPG III decarboxylase cassette PCR product was digested in 1× CUTSMART® Buffer with SphI-HF (New England BioLabs, Cat #R3182S) and AgeI-HF (New England BioLabs, Cat # R3552S) over night at 37° C.

Digested vector and PCR products were gel purified from 0.8% agarose using ZYMOCLEAN™ Gel DNA Recovery Kit (Zymo Research, Cat #D4002). DNA was eluted in 20 µl H$_2$O.

Three way ligation between UPG III synthase cassette digested with NheI-SphI, UPG III decarboxylase cassette digested with SphI-AgeI and a vector digested with NheI-AgeI was set up in 10 µl at 16° C. overnight using T4 DNA Ligase (New England BioLabs, Cat #M0202S).

1.5 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV; cells were incubated at 37° C. in 1 ml SOC for 1 h with shaking at 200 rpm. 10 µl of recovery mixture was plated on LB agar plates containing ampicillin at a concentration of 100 µg/ml. Plates were incubated overnight at 37° C. Colonies were screened by colony PCR for the presence of the insert. The sequences of the junctions between vector and inserts were confirmed. AssemblingPaox1_ALAsynthase_FDH1term.-Paox1_PPGoxidase_FDH1term-Paox1_Fc_FDH1term.-Paox1_PBD_FDH1term Cassette (pMx330)

a. PCR amplification of gene-cassettes:

ALAsynthase cassette was PCR amplified from pMx310 with primers to AOX1 promoter/FDH1 terminator containing NheI and XhoI recognition sites for restriction endonucleases correspondingly (Table 13):

TABLE 13

Primer Sequences

| Primer Designation | Recognition Sites | Sequence | SEQ ID NO: |
|---|---|---|---|
| Mx00399 | NheI-pAOX1-F | CAA TCG CTA GCA TCC AAC ATC AAA AGA CGA AAG G | 35 |
| Mx00400 | XhoI-FDH1-R | GAT ATT GCT CGA GAC CTT ATC AAG ATA GCT AGA AAT AGA AAT G | 36 |

PPGoxidase cassette was PCR amplified from pMx313 with primers to AOX1 promoter/FDH1 terminator containing XhoI and AflII recognition sites for restriction endonucleases correspondingly (Table 14):

TABLE 14

Primer Sequences

| Primer Designation | Recognition Sites | Sequence | SEQ ID NO: |
|---|---|---|---|
| Mx00403 | XhoI-pAOX1-F | CAA TCT CGA GAA CAT CCA AAG ACG AAA GGT TG | 37 |
| Mx00437 | AflII-FDH1-R | CAA CCA TTT CTA TTT CTA GCT ATC TTG ATA AGG TCT AAG TCA | 38 |

Ferrochelatase cassette was PCR amplified from pMx323 with primers to AOX1 promoter/FDH1 terminator containing AflII and AgeI recognition sites for restriction endonucleases correspondingly (Table 15):

TABLE 15

Primer Sequences

| Primer Designation | Recognition Sites | Sequence | SEQ ID NO: |
|---|---|---|---|
| Mx00404 | AgeI-FDH1-R | CAT GGT ACC GGT ACC TTA TCA AGA TAG CTA GAA ATA GAA ATG G | 39 |
| Mx00436 | AflII-pAOX1-F | TTA CTT AAG TCC AAC ATC AAA AGA CGA AAG GTT G | 40 |

G418 marker was PCR amplified from pJAG plasmid purchased from Biogrammatics using the following primers (Table 16):

TABLE 16

Primer Sequences

| Primer Designation | Recognition Sites | Sequence | SEQ ID NO: |
|---|---|---|---|
| Mx00438 | Mlu-G418-F | TCA CAG ACG CGT TGA ATT GTC C | 41 |
| Mx00439 | BbvCI-G418-R | TTG CTC CTC AGC TTA GAA GAA CTC GTC CAA CAT CAA GTG | 42 |

PHUSION® High-Fidelity DNA Polymerase (New England BioLabs, Cat #M0530L) was used to amplify DNA from plasmids. The PCR products were obtained and purified using DNA Clean&Concentrator-5 (Zymo Research, Cat #D4004) and DNA was eluted in 25 μl of H₂O.

b. Preparation of Vectors pGAZ-PBD (pMx321) designated as a vector was digested in 1× CUTSMART® Buffer with NheI-HF (New England BioLabs, Cat #R3131S) and XhoI (New England BioLabs, Cat #R0146S) overnight at 37° C.

pGAZ-ALAsyn.-PBD (pMx328) was digested in 1×NEBuffer3.1 with MluI (New England BioLabs, Cat #R0198S) and BbvCI (New England BioLabs, Cat #R0601S) overnight at 37° C.

pGAG-ALAsyn-PBD (pMx332) was digested in 1× CUTSMART® Buffer with XhoI (New England BioLabs, Cat #R0146S) and AgeI-HF (New England BioLabs, Cat #R3552S) overnight at 37° C.

c. Making Intermediate Constructs and Assembling a Final Cassette

Digested vector and PCR products were gel purified from 0.8% agarose using ZYMOCLEAN™ Gel DNA Recovery Kit (Zymo Research, Cat #D4002). DNA was eluted in 20 μl of H₂O.

pGAZ-PBD (pMx321) vector, digested with NheI-XhoI restriction endonucleases, was ligated with ALAsynthase cassette PCR product digested with the same enzymes in 10 μl reaction at 16° C. overnight using T4 DNA Ligase (New England BioLabs, Cat #M0202S) to yield a pGAZ-ALAsyn.-PBD plasmid (pMx328).

pGAG-ALAsyn-PBD (pMx332) digested with XhoI and AgeI-HF restriction endonucleases was ligated with PPGoxidase cassette and Ferrochelatase cassette PCR products digested with XhoI, AflII and AflIII, AgeI-HF restriction endonucleases correspondingly in a three way ligation reaction using T4 DNA Ligase (New England BioLabs, Cat #M0202S) to yield a pGAG-ALAsynthase_PPGoxidase_Fc_PBD (pMx330).

1.5 µl of ligation mixture was transformed into 20 µl of ElectroMax DH10B T1 Phage-Resistant Competent Cells (Invitrogen, Cat #12033-015) by electroporation using MICROPULSER™ (BioRad) set at 1.7 kV; cells were incubated at 37° C. in 1 ml SOC for 1 h with shaking at 200 rpm. 10 µl of recovery mixture was plated on LB agar plates containing ampicillin at a concentration of 100 µg/ml. Plates were incubated overnight at 37° C. Colonies were screened by colony PCR for the presence of the insert. The sequences of junctions between the vector and the inserts were confirmed. Strain designations and genetic constructs are described in Table 17.

strain MXY0118 contained several copies of the LegH gene, likely due to concatamerization of the plasmid, pMX282, at the time of recombination.

Figure 2:
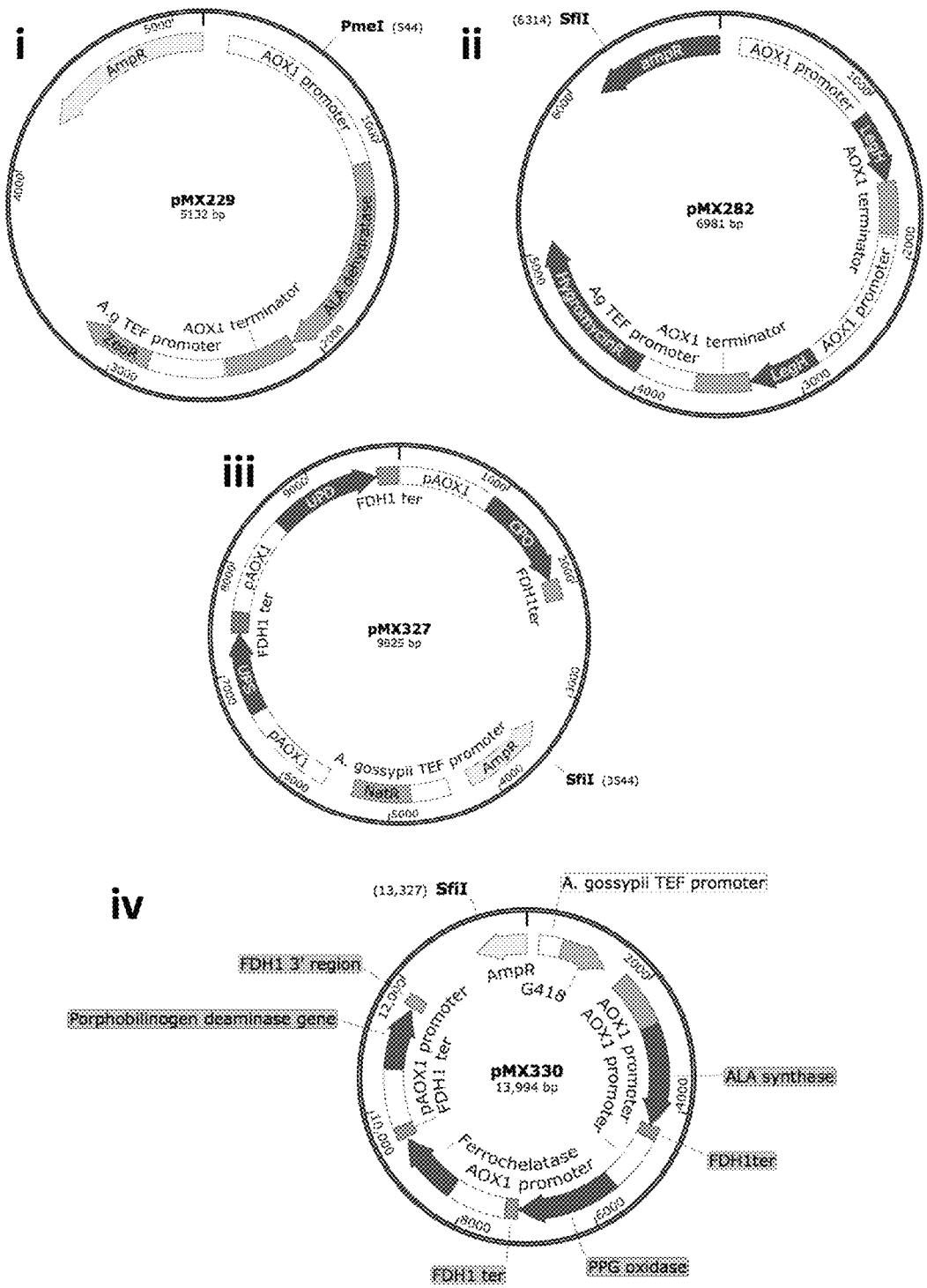
FIG. 2 are schematics of plasmids used in the construction of production strain MXY0183.
Figure 3:
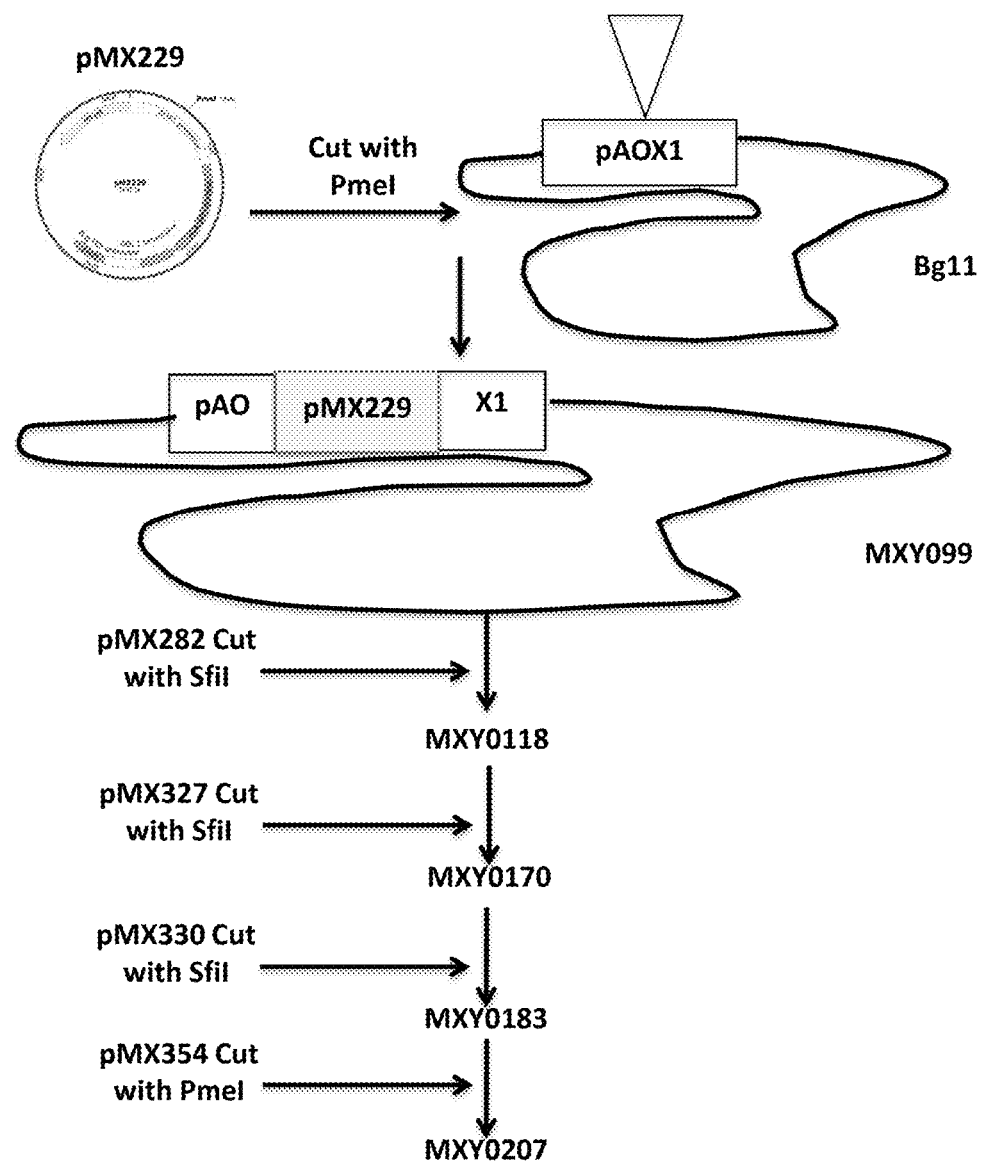
FIG. 3 is a schematic showing the generation of the production strains, MXY0183 and MXY0207, from the parent strain, Bg11.

Plasmid pMX327 (FIG. 2iii and FIG. 3) containing genes encoding Uroporphyrinogen III synthase (UPS), Uroporphyrinogen III decarboxylase (UPD) and Coproporphyrinogen III oxidase (CPO) (the enzymes catalyzing steps 4, 5 and 6, respectively) under control of the AOX1 promoter was linearized with the SfiI restriction endonuclease and introduced into MXY0118, yielding strain MXY0170 (FIG. 3).

Genes encoding ALA synthase (ALAS), Protoporphyrin III oxidase (PPO), Ferrochelatase (FC) and Porphobilinogen deaminase (PBD) (the enzymes catalyzing steps 1, 7, 8 and 3, respectively) from the *P. pastoris* genome were assembled on plasmid pMX330 (FIG. 2iv and FIG. 3). pMX330 was linearized with the SfiI restriction endonuclease and transformed into MXY0170, leading to the generation of strain

TABLE 17

Strain Designation and Genetic Constructs

| Designation | Construct | Gene |
|---|---|---|
| pMx0327 | pGAN-UPGsyn_UPGdecarb_CPGoxy | UPGsyn_UPGdecarb_CPGoxy |
| pMx0328 | pGAZ-ALAsyn-PGC | ALAsyn-PBD |
| pMx0330 | pGAG-ALAsyn_PBD_PPG_Fc | ALAsyn_PBD_PPG_Fc |
| pMx0332 | pGAG-ALAsyn_PBD | G418 marker |

Example 13—Integration of Linearized Plasmids with Gene Cassettes into *P. pastoris* Bg11 Genome The plasmids that were used to generate the production strain, MXY0183, are shown in FIG. 2. The steps taken to make the modifications that led to production strain, MXY0183, are depicted in FIG. 3.

The first enzyme to be introduced into the *P. pastoris* Bg11 genome was ALAD. A plasmid containing pAOX1-driven ALAD (pMX229, FIG. 2i and FIG. 3) was linearized using PmeI restriction enzyme (New England BioLab). Linearized plasmid was purified from 0.8% agarose gel as described and transformed into *P. pastoris* using homologous recombination at the native AOX1 locus, generating strain MXY099 (FIG. 3).

A plasmid containing two copies of the soybean LegH gene (sequence optimized for *P. pastoris*; SEQ ID NO:3) under the control of the pAOX1 promoter designated pMX282 (FIG. 2ii and FIG. 3) was linearized using SfiI restriction enzyme. Linearized plasmid was purified from a 0.8% agarose gel as described and transformed into the *P. pastoris* strain containing ALAD, generating the strain MXY0118 (FIG. 3). qPCR was used and determined that MXY0183 (FIG. 3). The genotype of MXY0183 was confirmed using PCR and qPCR.

Production Strain MXY0207

Example 14—Construction of pGAB Expression Vector

The pGAB expression vector (FIG. 4A) was constructed by replacing the open reading frame of the ZEOCIN™ resistance gene in the pGAZ vector (BioGrammatics, Inc., Carlsbad, Calif.) with the open reading frame from the Blasticidin S deaminase (BSD) gene from *Aspergillus terreus*, which allows for selection of transformants carrying the plasmid with the antibiotic Blasticidin S.

The BSD open reading frame was amplified from a commercially synthesized DNA molecule using oligonucleotide primers Mx00476 and Mx00477 using a high fidelity polymerase chain reaction as described herein (Table 18).

TABLE 18

Primer Sequences.

| Primer Designation | Description | Sequence | SEQ ID NO: |
|---|---|---|---|
| Mx00477 | BSD_Reverse | TTA GTC TTG CTC CTC AGC TTA GCC | 43 |
| Mx00476 | BSD_Forward | TCA CAG ACG CGT TGA ATT GTC C | 44 |

The BSD PCR product was purified by gel electrophoresis on a 1% agarose gel in 1×TBE buffer (89 mM Tris, 89 mM boric acid, 2 mM EDTA, pH 8.3) and visualized using SYBR™ Safe DNA gel stain (Life Technologies, Carlsbad, Calif.). The desired DNA fragment was excised from the agarose gel and the DNA was recovered using the ZYMO-CLEAN™ Gel DNA Recovery Kit (Zymo Research, Irvine, Calif.).

The purified BSD PCR product and pGAZ vector were digested with 10 units each of the MluI and BbvCI restriction endonucleases (New England Biolabs, Ipswich, Mass.) for 1 hour at 37° C. in 1×NEBuffer 3.1 (100 mM NaCl, 50 mM Tris-HCl, 10 mM $MgCl_2$, 100 µg/ml BSA, pH 7.9 @ 25° C.). Digested DNA products were recovered by gel electrophoresis as described above.

The purified, MluI and BbvCI digested BSD product and pGAZ vector were incubated with 400 units of T4 DNA ligase (New England Biolabs) in 1× T4 DNA ligase reaction buffer (50 mM Tris-HCl, 10 mM $MgCl_2$, 1 mM ATP, 10 mM DTT, pH 7.5 @ 25° C.) in a 20 µl reaction, at 16° C. for 2 hours in a 20 µl reaction. Electrocompetent *E. coli* DH10B cells were transformed with 2 µl of the ligation reaction and antibiotic resistant transformants were selected on LSB agar plates supplemented with 100 µg/µl ampicillin.

Example 15—Construction of Mxr1 Expression Vector

Figure 4:
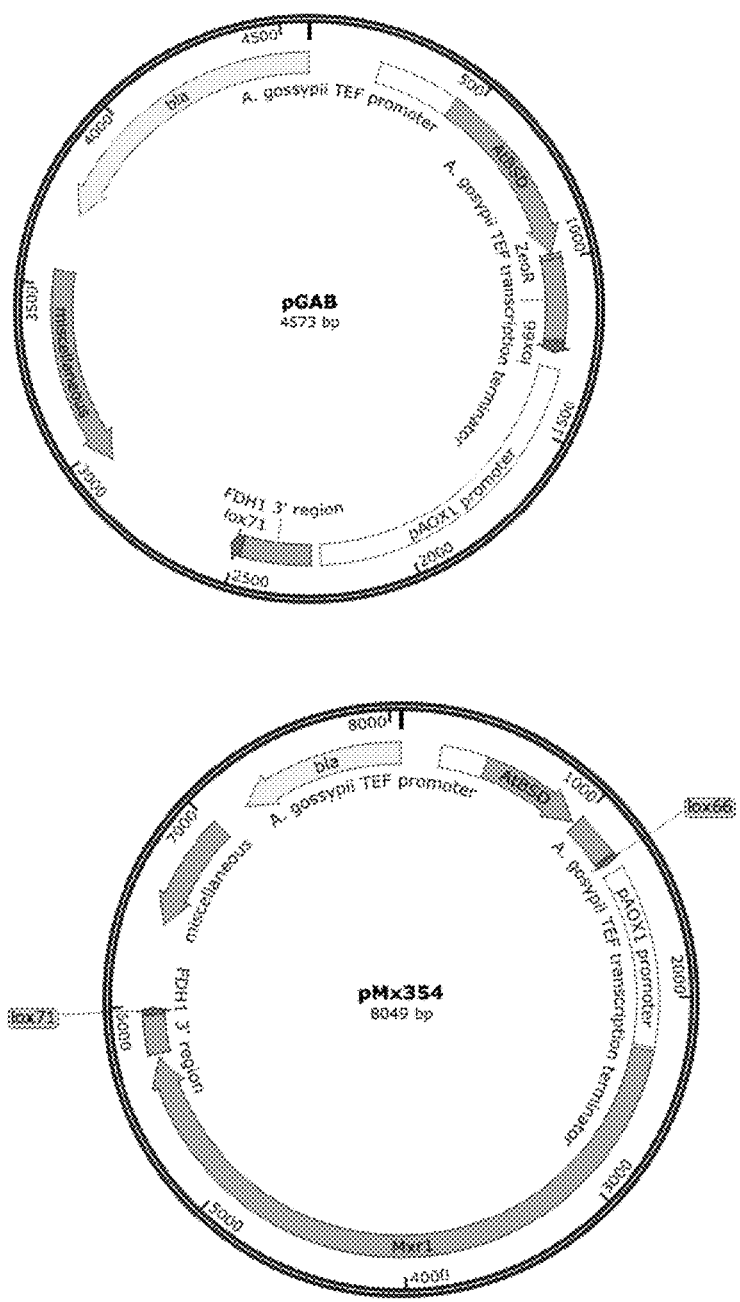
FIG. 4 are schematics showing plasmids pGAB and pMx354.

The Mxr1 expression vector, pMx354, was constructed by introducing the Mxr1 open reading frame into the pGAB vector (FIG. 4B). The Mxr1 open reading frame was inserted into pGAB with the translation start immediately downstream of the methanol-inducible alcohol oxidase 1 (AOX1) promoter from *Pichia pastoris* and the translation stop signal immediately followed by the transcription terminator sequence from the *P. pastoris* FDH1 gene.

The open reading frame encoding the Mxr1 protein was amplified from genomic DNA isolated from *Pichia pastoris* strain Bgl1 MutS obtained from BioGrammatics, Inc. (Carlsbad, Calif.). The Mxr1 open reading frame was amplified from *P. pastoris* genomic DNA with primers Mx00495 (TTT TGC GGC CGC ATG AGC AAT CTA CCC CCA ACT TTT G (SEQ ID NO:45)) and Mx00496 (AAA AGC GGC CGC CTA GAC ACC ACC ATC TAG TCG GTT (SEQ ID NO:46)), which appended flanking NotI restriction endonuclease recognition sites. Amplification was accomplished using the polymerase chain reaction as described herein.

The amplified Mxr1 PCR product and the pGAB vector were digested with 10 units of NotI restriction endonuclease (New England Biolabs) for 1 hour at 37° C. in 1×NEBuffer 3.1 (100 mM NaCl, 50 mM Tris-HCl, 10 mM $MgCl_2$, 100 µg/ml BSA, pH 7.9 @ 25° C.). Following digestion, the NotI-digested pMx352 vector was treated with 5 units Antarctic phosphatase (New England Biolabs) for 15 minutes at 37° C. in 1× Antarctic phosphatase buffer (50 mM Bis-Tris-Propane-HCl, 1 mM $MgCl_2$, 0.1 mM $ZnCl_2$, pH 6 @ 25° C.).

The NotI-digested amplified Mxr1 fragment and pMx352 vector were separated by electrophoresis on a 1% agarose gel in 1×TBE buffer (89 mM Tris, 89 mM boric acid, 2 mM EDTA, pH 8.3) and visualized using SYBR™ Safe DNA gel stain (Life Technologies, Carlsbad, Calif.). The desired DNA fragments were excised from the agarose gel and the DNA was recovered using the ZYMOCLEAN™ Gel DNA Recovery Kit (Zymo Research, Irvine, Calif.).

The NotI-digested fragment containing Mxr1 open reading frame was introduced into pGAB at a NotI site immediately downstream of the AOX1 promoter by ligation. A mixture containing 137 ng of NotI-digested DNA encoding the Mxr1 open reading frame and 60 ng of NotI-digested, phosphatase-treated pMx352 was incubate with 400 units of T4 DNA ligase (New England Biolabs) in 1× T4 DNA ligase reaction buffer (50 mM Tris-HCl, 10 mM $MgCl_2$, 1 mM ATP, 10 mM DTT, pH 7.5 @ 25° C.) in a 20 µl reaction, at 16° C., for 2 hours in a 20 µl reaction. Electrocompetent *E. coli* DH10B cells were transformed with 2 µl of the ligation reaction and antibiotic resistant transformants were selected on LSB agar plates supplemented with 100 µg/µl ampicillin. Plates were incubated overnight at 37° C. Colonies were screened for the presence of the insert by PCR using primers Mx00495 and Mx00496. The sequence of the final vector was confirmed by DNA sequencing.

During cloning, 6 additional amino acids were introduced at the N-terminus of Mxr1. The Mxr1 open reading frame is shown under the section "Nucleic acid sequences", with residual amino acids from the cloning shown with underlining. *Pichia* production strains containing the Mxr1 sequence having the additional 6-amino acids at the N-terminus and *Pichia* strains containing the wild type Mxr1 (i.e., without the additional 6 amino acids at the N-terminus) were indistinguishable in fermentation tanks.

Example 16—Construction of Native Mxr1 Expression Vector

A plasmid containing the Mxr1 transcription regulator gene under the control of the pAOX1 promoter, designated pMX354, was used as a template for PCR amplification. The 3' end of the AOX1 promoter, the LegH open reading frame, and the AOX1 terminator were amplified from pMX354 using primers Mx00617 and Mx00647 shown below. The AOX1 terminator, linker and the 5' end of the AOX1 promoter were amplified from pMX382 using primers Mx00618 and Mx00646 (Table 19).

TABLE 19

Primer Sequences.

| Primer Designation | Sequence | SEQ ID NO: |
|---|---|---|
| Mx00646 | ACTAGATGGTGGTGTCTAGTCAAGAGGATGTCAGAATGCCATTTG | 47 |
| Mx00647 | TCTGACATCCTCTTGACTAGACACCACCATCTAGTCGGTTTTCTAG | 48 |

PCR products were obtained and purified using DNA Clean&Concentrator-5 and DNA was eluted in 12 µl of $H_2O$. The purified PCR products were then combined and used as a template for a subsequent round of PCR amplification using primers Mx00617 and Mx00618. The resulting PCR product was composed of the 3' end of the AOX1 promoter, followed by the Mxr1 open reading frame, the AOX1 terminator, a short linker sequence, and the 5' end of the AOX1 promoter. The PCR product was obtained and purified as described herein. The purified PCR product was cloned into the pCR™-Blunt II-TOPO® vector using the Zero Blunt® TOPO® PCR Cloning Kit (Invitrogen, Cat #K2800-20) to create the pMX402 vector.

Example 17—Construction of *P. pastoris* Strains MXY0206 and MXY0207

The pMx354 Mxr1 expression vector (FIG. 4B) was introduced into the MXY0183 strain by DNA transformation (FIG. 3).

The pMx354 vector (1.5 µg) was linearized at a unique PmeI site in the AOX1 promoter sequences by digestion with 20 units of the PmeI restriction endonuclease (New England Biolabs) for 1 hour at 37° C. in 1×NEBuffer 4 (50 mM Potassium Acetate, 20 mM Tris-acetate, 10 mM Magnesium Acetate, 1 mM DTT, pH 7.9@25° C.).

The PmeI-digested pMX354 vector was purified by gel electrophoresis recovered using the ZYMOCLEAN™ Gel DNA Recovery Kit as described above. The linearized pMX354 vector was introduced into strain MXY0183 by transformation and selection on blasticidin-containing medium. Two independent clones were obtained from the transformation, and they were designated MXY0206 and MXY0207. The presence of an additional copy of Mxr1 under the control of the AOX1 promoter in these strains was confirmed by PCR.
Production Strain MXY0291

Example 18—Construction of Strains MXY0213 and MXY0260

Figure 5:
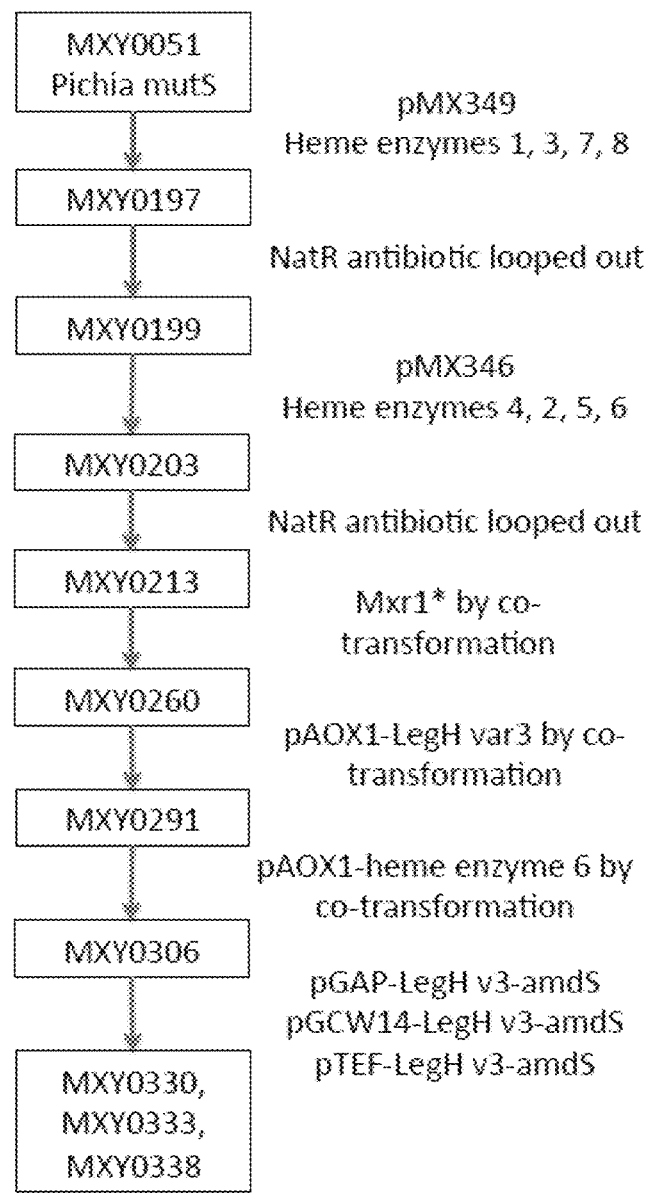
FIG. 5 is a schematic showing the generation of the antibiotic selection free production strains, MXY0291 and MXY0338, from the parent strain, Bg11.
Figure 6:
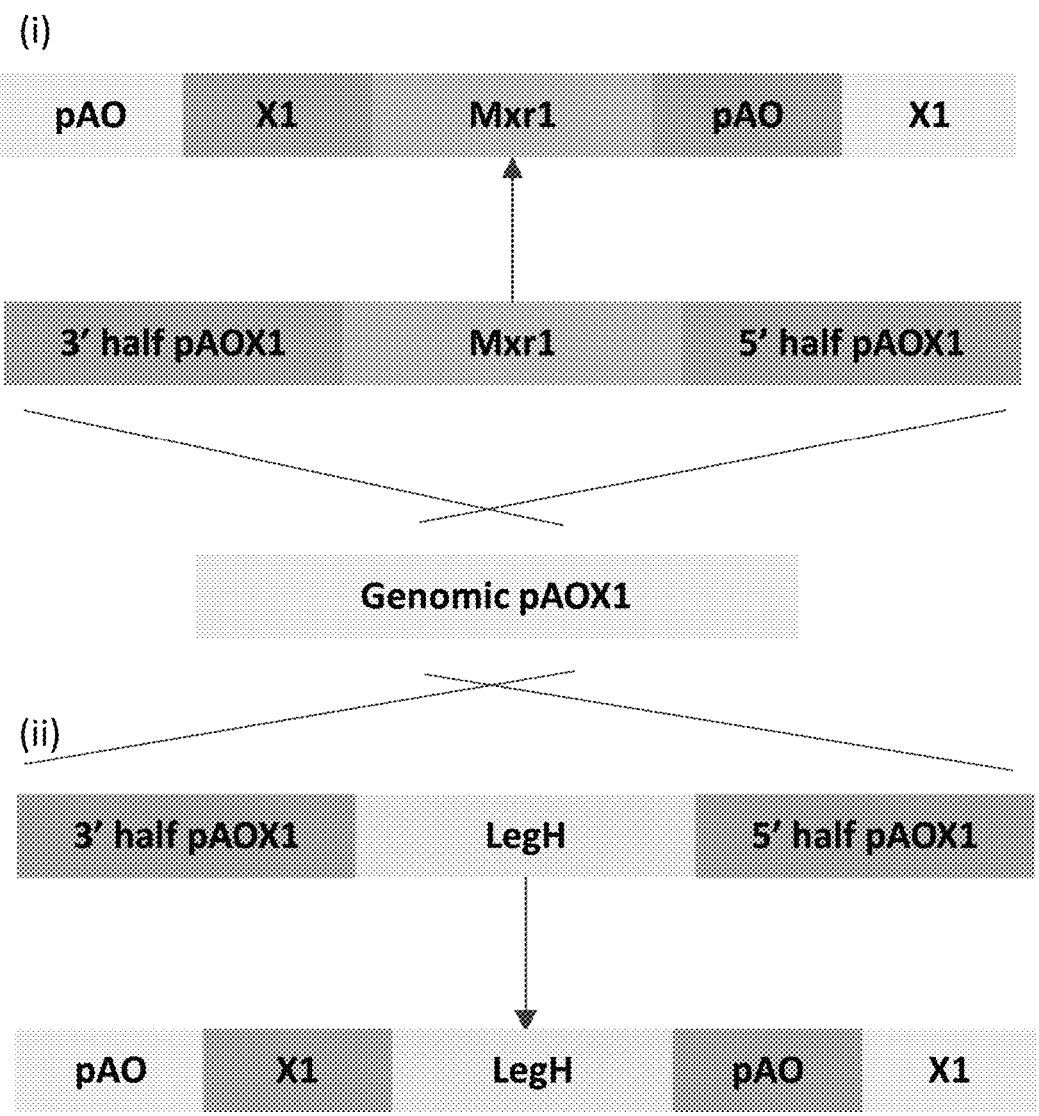
FIG. 6 is a schematic of the linear pieces of DNA containing Mxr1 and LegH var 3 that were introduced by co-transformation to make the production strain MXY0291.

FIG. 5 shows the steps taken to construct antibiotic marker free strain MXY0213 that contains 7 enzymes of the heme biosynthetic pathway. A linear piece of DNA containing variant Mxr1 (6 extra amino acids at N terminus) under pAOX1, with homology to the pAOX1 promoter on each end, was introduced using co-transformation (FIG. 5 and FIG. 6*i*). This linear Mxr1 expression cassette was simultaneously introduced into *Pichia* strain MXY213 with the pIL75 plasmid by transformation. The pIL75 vector carries a panARS autonomous replication sequence (Liachko & Dunham, 2014, FEMS Yeast Res., 14:364-7), which allows for maintenance of the plasmid vector without integration into the genome of the transformed cells, and a kanMX marker for selection of transformants with the antibiotic G418. Transformed cells were selected on media supplemented with G418 for the presence of kanMX marker on the pIL75 plasmid. *Pichia* transformants were screened by colony PCR for transformants that took up both the pIL75 plasmid and had correctly integrated the Mxr1 expression cassette.

Example 19—Co-Transformation to Introduce the LegH Expression Cassette into *Pichia*

A plasmid containing a different *Pichia pastoris*-codon optimized variant of soybean LegH gene (variant 3; SEQ ID NO:5) under the control of the pAOX1 promoter designated pMX399 was used as a source of template for PCR amplification of the gene. The backbone from TOPO cloning plasmid pMX401 was PCR amplified. The insert and vector were assembled using GIBSON ASSEMBLY® (NEB GIBSON ASSEMBLY® kit) to generate plasmid pMX422. This plasmid was used as a template for a subsequent round of PCR amplification using primers Mx00617 and Mx00618 shown below (Table 20).

TABLE 20

Primer Sequences.

| Primer Designation | Sequence | SEQ ID NO: |
|---|---|---|
| Mx00617 | AAACGCTGTCTTGGAACCTAATATGAC | 49 |
| Mx00618 | AAACTGTCAGTTTTGGGCCATTTG | 50 |

The resulting PCR product was composed of, in the 5' to 3' direction, the 3' end of the AOX1 promoter, followed by the LegH var 3 open reading frame, the AOX1 terminator, a short linker sequence, and the 5' end of the AOX1 promoter (FIG. 6*ii*). The PCR product was obtained and purified by agarose gel electrophoresis as described herein.

Transformants with LegH expression cassette integrated into the genome were screened by PCR and characterized for LegH gene copy number using qPCR.

Example 20 Curing Transformants of Plasmid Vectors Bearing Selection Markers In clones where the soybean LegH expression cassette was shown to be correctly integrated by colony PCR and in high copy number by qPCR, the pIL75 plasmid required for selection on G418 was eliminated by relaxing selection for the antibiotic. Transformants were streaked out for single colonies on media lacking G418 antibiotic. Because the panARS plasmid is not stably maintained in the absence of selection, the pIL75 was rapidly lost from the transformed cells under this condition. The resulting *Pichia* strain, MXY0291, contains sequences for LegH expression in copy number similar to MXY0207, but lacks heterologous sequences for selection.
Production Strains MXY0330, MXY0333, and MXY0338

Example 21—Construction of Strain MXY0306

Genotype PCR of strain MXY0291 revealed that a portion of the CPGoxidase coding sequence had been deleted during construction of this strain. The full-length CPGoxidase coding region was restored by replacement of the truncated copy. Briefly, a linear DNA fragment containing the pAOX1 promoter and full-length CPGoxidase coding region was generated by PCR amplification from plasmid pMX312 using primers Mx00866 and Mx00867 shown below (Table 21).

TABLE 21

Primer Sequences.

| Primer Designation | Sequence | SEQ ID NO: |
|---|---|---|
| Mx00866 | ACGCTGTCTTGGAACCTAATATGAC | 51 |
| Mx00867 | TACCCATTCAATAGGATTTTGTAGTACCTGC | 52 |

The linear pAOX1-CPGoxidase DNA fragment was introduced into strain MXY0291 by co-transformation with the pIL75 plasmid. Transformants were selected on media containing G418 and then screened for the presence of the full-length CPGoxidase coding region by PCR. An isolate containing the full-length CPGoxidase was identified and subsequently cured of the plasmid vector required for selection on G418 as described above. This strain was designated MXY0306 (see FIG. 5).

Example 22—Linear Constructs for Hybrid Promoter Strains

Figure 7:
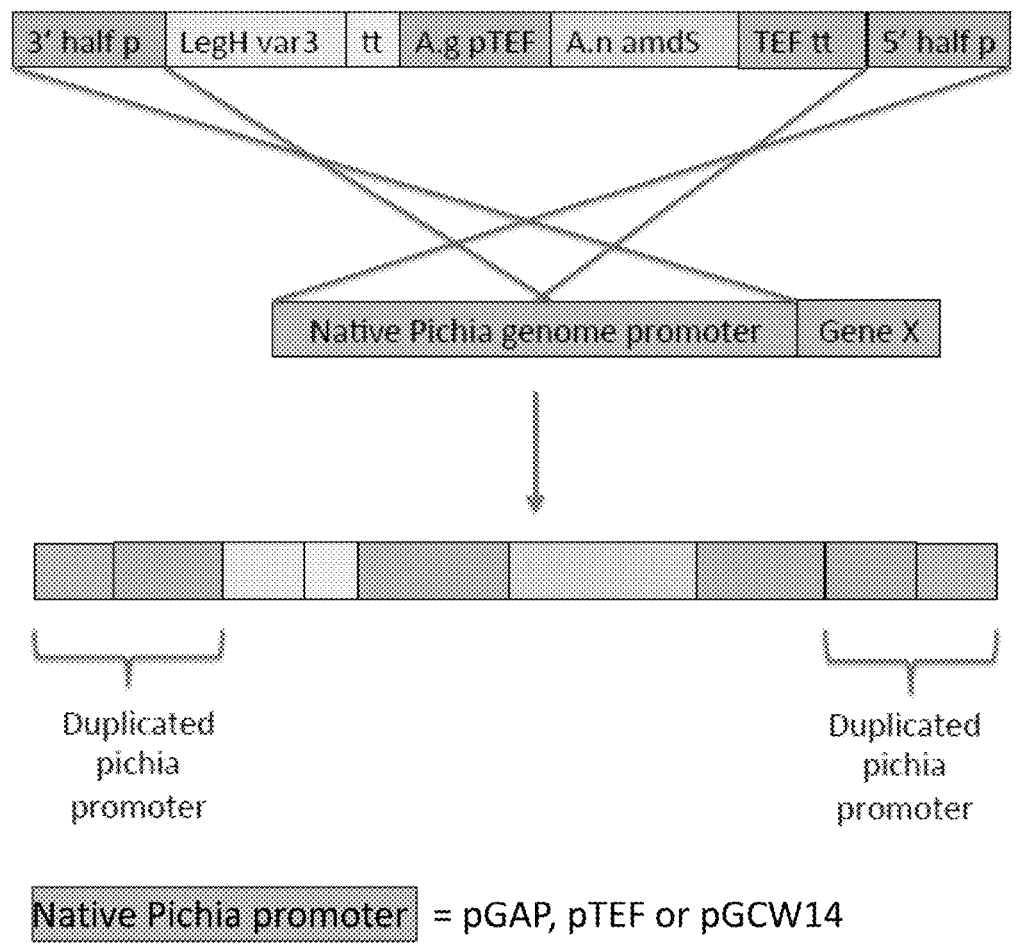
FIG. 7 is a schematic showing the linear construct expressing LegH under control of native *Pichia* non-pAOX1 constitutive promoters.

LegH variant 3 was expressed under the direction of each of the three native *Pichia pastoris* constitutive promoters indicated herein. The linear constructs are shown in FIG. 7, and contained the 3' half of the promoter, followed by LegH var3, followed by the FDH1 transcription terminator. This was immediately followed by the antibiotic resistance cassette containing the pTEF promoter from *Ashbya gossypii*, the acetamidase gene (amdS) from *Aspergillus nidulans* and the TEF terminator from *Ashbya gossypii*. Finally, the construct contained the 5' half of the promoter. This linear cassette was amplified using the oligonucleotide primers listed in Table 22 below to generate constructs that contain several hundred base pairs on the 5' and 3' ends that are homologous to the respective promoter in the native *Pichia* genome.

TABLE 22

Primers used to amplify the linear constructs

| Primer designation | Sequence | SEQ ID NO: |
|---|---|---|
| MXO0718 | GAGCTTCTTCTACGGCCCCC | 53 |
| MXO0723 | TCCAGCAGAGTAAAATTTCCTAGGGAC | 54 |

TABLE 22-continued

Primers used to amplify the linear constructs

| Primer designation | Sequence | SEQ ID NO: |
|---|---|---|
| MXO0724 | CTCTTTTAGGTTTTAAGTTGTGGGAACAGTA ACA | 55 |
| MXO0729 | GTGGGTGCTTCTTTGCGTGG | 56 |
| MXO0730 | AGAATTGCCATCAAGAGACTCAGGACT | 57 |
| MXO0735 | GATAGAGAGAAATCGCAAACTTTGAGAGGAAG | 58 |

Competent MXY0306 cells were transformed with each of the linear cassettes and transformants containing the amdS selection cassette were selected based on their ability to grow on agar plates containing acetamide as the sole nitrogen source. These strains were purified, isolated and the presence of LegH under control of the constitutive promoter was verified by PCR (FIG. 5).

Example 23—Nucleic Acid Sequences

Mxr1 nucleic acid sequence (the underlined nucleotides encode 6 amino acid at N-term introduced during cloning)
(SEQ ID NO: 1)
ATGCGAGACCGCGGCCGCATGAGCAATCTACCCCCAACTTTTGGTTCCACTAGACAATCTCCAGA

AGACCAATCACCTCCCGTGCCCAAGGAGCTGTCATTCAATGGGACCACACCCTCAGGAAAGCTAC

GCTTATTTGTCTGTCAGACATGTACTCGAGCATTTGCTCGTCAGGAACACTTGAAACGACACGAA

AGGTCTCACACCAAGGAGAAACCTTTCAGCTGCGGCATTTGTTCTCGTAAATTCAGCCGTCGAGA

TCTGTTATTGAGACATGCCCAAAAACTGCACAGCAACTGCTCTGATGCGGCCATAACAAGACTAA

GGCGCAAGGCAACTCGTCGGTCTTCTAATGCCGCGGGTTCCATATCTGGTTCTACTCCGGTGACA

ACGCCAAATACTATGGGTACGCCCGAAGATGGCGAGAAACGAAAAGTTCAGAAACTGGCCGGCCG

CCGGGACTCAAATGAACAGAAACTGCAACTGCAACAACAACATCTACAGCAACAACCACAGTTGC

AATACCAACAATCTCTTAAGCAGCATGAAAATCAAGTCCAGCAGCCTGATCAAGATCCATTGATA

TCCCCGAGAATGCAATTATTCAATGATTCCAACCATCACGTAAACAATTTGTTTGATCTTGGACT

AAGAAGAGCTTCCTTCTCCGCCGTTAGTGGAAATAATTATGCCCATTATGTGAATAATTTTCAAC

AAGATGCCTCTTCTACCAATCCAAATCAAGATTCAAATAATGCCGAATTTGAGAATATTGAATTT

TCTACCCCACAAATGATGCCCGTTGAAGATGCTGAAACTTGGATGAACAACATGGGTCCAATTCC

GAACTTCTCTCTCGATGTGAACAGGAACATTGGTGATAGCTTTACAGATATACAACACAAGAATT

CAGAGCCTATTATATCCGAACCGCCCAAGGACACCGCTCCAAACGACAAGAAGTTGAATGGCTAC

TCTTTTTACGAAGCCCCCATCAAGCCATTAGAATCCCTATTTTCTGTCAGGAATACAAAGAGAAA

CAAGTATAAAACAAATGACGACTCTCCAGACACCGTGGATAATAACTCCGCACCGGCTGCTAATA

CCATTCAAGAACTTGAGTCTTCTTTGAATGCATCCAAGAATTTTTGCTTGCCAACTGGTTATTCC

TTCTATGGTAATTTGGACCAACAGACTTTCTCTAACACGTTATCATGCACTTCTTCTAATGCCAC

AATTTCGCCCATTCTACTCGATAACTCCATTAATAATAACTCCACTAGTGACGTGAGACCAGAAT

-continued

```
TTAGAACACAAAGTGTCACCTCTGAAATGAGTCAAGCCCCTCCCCCTCCTCAAAAAAACAACTCG
AAATATTCCACCGAAGTTCTTTTTACCAGCAACATGCGGTCGTTTATTCACTACGCTCTTTCCAA
GTATCCTTTTATTGGTGTGCCCACTCCAACTCTTCCGGAGAACGAAAGACTAAATGAATATGCTG
ATTCATTCACCAACCGTTTCTTAAATCATTATCCTTTCATACATGTCACGATTCTCAAAGAATAC
TCCCTTTTCAAGGCAATTTTAGATGAGAATGAGTCGACTAAGAACTGGGAAAATAATCAGTTTTA
CTTAGAGAACCAACGAATATCAATTGTTTGTCTTCCTCTTTTGGTGGCTACGATAGGTGCAGTAC
TATCAAACAACAAAAGGATGCTTCGAATTTATACGAAGCTTCAAGGCGTTGTATTCATGTTTAC
TTAGATTCCAGGAAAAAGATACCCACTTCCTTGTCCGCAAATAACAATGACTCTCCACTTTGGCT
AATTCAATCCCTGACGTTATCTGTTATGTATGGGTTATTTGCGGACAATGACATTAGTTTGAATG
TCGTGATCAGACAAGTTAACGCACTTAATTCTCTGGTCAAGACTTCGGGCCTGAATAGGACCTCA
ATTATAGATCTTTTCAACATCAACAAACCTTTGGATAATGAACTCTGGAATCAATTCGTGAAAAT
AGAGTCCACCGTAAGGACAATCCACACGATTTTTCAAATCAGTTCCAACTTAAGCGCCTTGTACA
ATATTATTCCATCGTTGAAAATTGATGACCTAATGATTACTCTACCAGTTCCCACAACACTTTGG
CAAGCTGATTCTTTTGTGAAATTCAAAAGTCTAAGTTACGGAAATCAGATCCCTTTTCAATATAC
AAGAGTACTACAGAATTTGATTGATTACAATCAGCCATTGAGCGATGGAAAATTTTTGTATGAAA
ACCATGTAAGTGAGTTTGGACTCATATGCCTACAGAATGGTCTACACCAATACAGCTATTTCCAA
AAATTGACTGCTGTCAATAACAGAGAAGATGCGCTATTCACAAAGGTTGTTAATTCACTTCACAG
TTGGGATAGGATGATTTCGAATTCTGATTTGTTTCCAAAGAAGATATATCAGCAGAGTTGCTTGA
TTTTGGACTCAAAGTTGCTTAATAATTTCCTGATTGTCAAGAGCTCATTGAAAGTTTCGACCGGA
GACGTTAGTTCTTTGAATAAGTTAAAAGAAAACGTGTGGCTTAAAAACTGGAATCAAGTGTGTGC
TATCTATTATAACAGCTTCATGAACATTCCTGCTCCCAGTATTCAAAAGAAGTACAATGACATAG
AGTTTGTGGATGACATGATTAATTTGAGTCTAATCATCATCAAGATTATGAAACTCATTTTCTAT
AACAATGTCAAAGACAATTATGAGGATGAAAATGACTTCAAATTGCAAGAGTTAAATTTAACATT
TGACAATTTTGATGAGAAAATATCCTTGAATTTGACAATATTATTCGATATATTTTTGATGATCT
ACAAGATAATTACCAATTACGAAAAGTTTATGAAGATCAAACACAAGTTTAATTACTACAATTCT
AATTCGAATATAAGCTTCTTGCATCATTTCGAACTCTCCTCGGTTATCAATAACACCCAAATGAA
CCAGAATGATTATATGAAAACAGATATTGATGAAAAGCTTGATCAGCTTTTCCACATCTATCAAA
CATTTTTCCGGCTGTATCTGGATTTAGAAAAGTTTATGAAGTTCAAATTCAACTATCATGACTTT
GAGACAGAGTTTTCAAGTCTCTCAATATCCAATATACTGAACACTCATGCTGCTTCTAACAATGA
CACAAATGCTGCTGATGCTATGAATGCCAAGGATGAAAAAATATCTCCCACAACTTTGAATAGCG
TATTACTTGCTGATGAAGGAAATGAAAATTCCGGTCGTAATAACGATTCAGACCGCCTGTTCATG
CTGAACGAGCTAATTAATTTTGAAGTAGGTTTGAAATTTCTCAAGATAGGTGAGTCATTTTTTGA
TTTCTTGTATGAGAATAACTACAAGTTCATCCACTTCAAAAACTTAAATGACGGAATGTTCCACA
TCAGGATATACCTAGAAAACCGACTAGATGGTGGTGTCTAG
```

Mxr1 protein sequence (the underlined 6 amino acid at N-term introduced during cloning)

(SEQ ID NO: 2)

<u>MRDRGR</u>MSNLPPTFGSTRQSPEDQSPPVPKELSFNGTTPSGKLRLFVCQTCTRAFARQEHLKRHE

RSHTKEKPFSCGICSRKFSRRDLLLRHAQKLHSNCSDAAITRLRRKATRRSSNAAGSISGSTPVT

TPNTMGTPEDGEKRKVQKLAGRRDSNEQKLQLQQQHLQQQPQLQYQQSLKQHENQVQQPDQDPLI

SPRMQLFNDSNHHVNNLFDLGLRRASFSAVSGNNYAHYVNNFQQDASSTNPNQDSNNAEFENIEF

STPQMMPVEDAETWMNNMGPIPNFSLDVNRNIGDSFTDIQHKNSEPIISEPPKDTAPNDKKLNGY

SFYEAPIKPLESLFSVRNTKRNKYKTNDDSPDTVDNNSAPAANTIQELESSLNASKNFCLPTGYS

FYGNLDQQTFSNTLSCTSSNATISPILLDNSINNNSTSDVRPEFRTQSVTSEMSQAPPPPQKNNS

KYSTEVLFTSNMRSFIHYALSKYPFIGVPTPTLPENERLNEYADSFTNRFLNHYPFIHVTILKEY

SLFKAILDENESTKNWENNQFYLENQRISIVCLPLLVATIGAVLSNNKKDASNLYEASRRCIHVY

LDSRKKIPTSLSANNNDSPLWLIQSLTLSVMYGLFADNDISLNVVIRQVNALNSLVKTSGLNRTS

IIDLFNINKPLDNELWNQFVKIESTVRTIHTIFQISSNLSALYNIIPSLKIDDLMITLPVPTTLW

QADSFVKFKSLSYGNQIPFQYTRVLQNLIDYNQPLSDGKFLYENHVSEFGLICLQNGLHQYSYFQ

KLTAVNNREDALFTKVVNSLHSWDRMISNSDLFPKKIYQQSCLILDSKLLNNFLIVKSSLKVSTG

DVSSLNKLKENVWLKNWNQVCAIYYNSFMNIPAPSIQKKYNDIEFVDDMINLSLIIIKIMKLIFY

NNVKDNYEDENDFKLQELNLTFDNFDEKISLNLTILFDIFLMIYKIITNYEKFMKIKHKFNYYNS

NSNISFLHHFELSSVINNTQMNQNDYMKTDIDEKLDQLFHIYQTFFRLYLDLEKFMKFKFNYHDF

ETEFSSLSISNILNTHAASNNDTNAADAMNAKDEKISPTTLNSVLLADEGNENSGRNNDSDRLFM

LNELINFEVGLKFLKIGESFFDFLYENNYKFIHFKNLNDGMFHIRIYLENRLDGGV*

*Pichia pastoris*-Codon-optimized LegH nucleic acid sequence
(SEQ ID NO: 3)
ATGGGTGCTTTCACCGAGAAGCAGGAAGCACTTGTTTCCTCTTCGTTCGAAGCTTTTAAGGCTAA

CATCCCTCAATACTCTGTTGTGTTTTACACGTCCATTCTAGAAAAAGCTCCTGCTGCCAAGGACC

TCTTCTCTTTTCTGTCCAACGGTGTAGATCCATCCAATCCCAAATTAACAGGTCACGCTGAGAAA

TTGTTCGGTTTAGTCAGAGATAGCGCTGGACAATTGAAAGCAAATGGTACTGTGGTTGCTGATGC

TGCCTTGGGCAGCATCCATGCACAGAAGGCAATTACAGACCCACAATTTGTTGTTGTGAAGGAAG

CTCTGCTTAAAACTATAAAGGAAGCCGTCGGAGACAAATGGAGTGACGAGTTGTCATCAGCTTGG

GAGGTAGCTTATGATGAGTTGGCCGCAGCAATCAAAAAGGCATTCTAA

*Pichia pastoris*-Codon-optimized LegH amino acid sequence (SEQ ID NO: 4)

MGAFTEKQEALVSSSFEAFKANIPQYSVVFYTSILEKAPAAKDLFSFLSNGVDPSNPKLTGHAEK

LFGLVRDSAGQLKANGTVVADAALGSIHAQKAITDPQFVVVKEALLKTIKEAVGDKWSDELSSAW

EVAYDELAAA

IKKAF

*Pichia pastoris*-Codon-optimized LegH variant 3 nucleic acid sequence (SEQ ID NO: 5)

ATGGGTGCATTTACAGAAAAACAAGAGGCTTTAGTATCCTCATCTTTTGAAGCTTTCAAAGCCAA

TATTCCTCAATACTCCGTTGTTTTCTATACGTCCATTTTGGAAAAGGCTCCAGCAGCTAAGGACC

TTTTCTCTTTCTTGTCGAACGGCGTGGATCCCTCAAATCCTAAGCTGACTGGTCACGCCGAGAAG

CTTTTTGGTTTGGTCAGAGACAGCGCCGGACAGCTGAAAGCTAACGGTACAGTTGTGGCAGATGC

TGCCTTGGGATCTATACATGCACAAAAGGCTATCACCGACCCACAGTTTGTGGTTGTAAAAGAGG

CTCTACTCAAAACTATCAAGGAAGCAGTTGGTGACAAATGGAGCGATGAATTGTCCAGTGCATGG

GAGGTCGCTTACGATGAGTTAGCTGCTGCAATCAAAAAGGCTTTCTAA

*Pichia pastoris*-Codon-optimized LegH variant 3 amino acid sequence (SEQ ID NO: 6)

MGAFTEKQEALVSSSFEAFKANIPQYSVVFYTSILEKAPAAKDLFSFLSNGVDPSNPKLTGHAEK

LFGLVRDSAGQLKANGTVVADAALGSIHAQKAITDPQFVVVKEALLKTIKEAVGDKWSDELSSAW

EVAYDELAAAIKKAF

*Pichia pastoris* pAOX1 promoter (SEQ ID NO: 7)

GATCTAACATCCAAAGACGAAAGGTTGAATGAAACCTTTTTGCCATCCGACATCCACAGGTCCAT

TCTCACACATAAGTGCCAAACGCAACAGGAGGGGATACACTAGCAGCAGACCGTTGCAAACGCAG

GACCTCCACTCCTCTTCTCCTCAACACCCACTTTTGCCATCGAAAAACCAGCCCAGTTATTGGGC

TTGATTGGAGCTCGCTCATTCCAATTCCTTCTATTAGGCTACTAACACCATGACTTTATTAGCCT

GTCTATCCTGGCCCCCCTGGCGAGGTTCATGTTTGTTTATTTCCGAATGCAACAAGCTCCGCATT

ACACCCGAACATCACTCCAGATGAGGGCTTTCTGAGTGTGGGGTCAAATAGTTTCATGTTCCCCA

AATGGCCCAAAACTGACAGTTTAAACGCTGTCTTGGAACCTAATATGACAAAAGCGTGATCTCAT

CCAAGATGAACTAAGTTTGGTTCGTTGAAATGCTAACGGCCAGTTGGTCAAAAGAAACTTCCAA

AAGTCGGCATACCGTTTGTCTTGTTTGGTATTGATTGACGAATGCTCAAAAATAATCTCATTAAT

GCTTAGCGCAGTCTCTCTATCGCTTCTGAACCCCGGTGCACCTGTGCCGAAACGCAAATGGGGAA

ACACCCGCTTTTTGGATGATTATGCATTGTCTCCACATTGTATGCTTCCAAGATTCTGGTGGGAA

TACTGCTGATAGCCTAACGTTCATGATCAAAATTTAACTGTTCTAACCCCTACTTGACAGCAATA

TATAAACAGAAGGAAGCTGCCCTGTCTTAAACCTTTTTTTTATCATCATTATTAGCTTACTTTC

ATAATTGCGACTGGTTCCAATTGACAAGCTTTTGATTTTAACGACTTTTAACGACAACTTGAGAA

GATCAAAAAACAACTAATTATTCGAAACG

*Pichia pastoris* pGAP promoter (SEQ ID NO: 8)

CGACTATTATCGATCAATGAAATCCATCAAGATTGAAATCTTAAAATTGCCCCTTTCACTTGACA

GGATCCTTTTTTGTAGAAATGTCTTGGTGTCCTCGTCCAATCAGGTAGCCATCTCTGAAATATCT

GGCTCCGTTGCAACTCCGAACGACCTGCTGGCAACGTAAAATTCTCCGGGGTAAAACTTAAATGT

GGAGTAATGGAACCAGAAACGTCTCTTCCCTTCTCTCTCCTTCCACCGCCCGTTACCGTCCCTAG

GAAATTTTACTCTGCTGGAGAGCTTCTTCTACGGCCCCCTTGCAGCAATGCTCTTCCCAGCATTA

CGTTGCGGGTAAAACGGAGGTCGTGTACCCGACCTAGCAGCCCAGGGATGGAAAAGTCCCGGCCG

TCGCTGGCAATAATAGCGGGCGGACGCATGTCATGAGATTATTGGAAACCACCAGAATCGAATAT

AAAAGGCGAACACCTTTCCCAATTTTGGTTTCTCCTGACCCAAAGACTTTAAATTTAATTTATTT

GTCCCTATTTCAATCAATTGAACAACTATCAAAACACG

*Pichia pastoris* pGCW14 promoter (SEQ ID NO: 9)

CAGGTGAACCCACCTAACTATTTTTAACTGGGATCCAGTGAGCTCGCTGGGTGAAAGCCAACCAT

CTTTTGTTTCGGGGAACCGTGCTCGCCCCGTAAAGTTAATTTTTTTTCCCGCGCAGCTTTAATC

TTTCGGCAGAGAAGGCGTTTTCATCGTAGCGTGGGAACAGAATAATCAGTTCATGTGCTATACAG

GCACATGGCAGCAGTCACTATTTTGCTTTTTAACCTTAAAGTCGTTCATCAATCATTAACTGACC

AATCAGATTTTTTGCATTTGCCACTTATCTAAAAATACTTTTGTATCTCGCAGATACGTTCAGTG

GTTTCCAGGACAACACCCAAAAAAAGGTATCAATGCCACTAGGCAGTCGGTTTTATTTTTGGTCA

CCCACGCAAAGAAGCACCCACCTCTTTTAGGTTTTAAGTTGTGGGAACAGTAACACCGCCTAGAG

CTTCAGGAAAAACCAGTACCTGTGACCGCAATTCACCATGATGCAGAATGTTAATTTAAACGAGT

GCCAAATCAAGATTTCAACAGACAAATCAATCGATCCATAGTTACCCATTCCAGCCTTTTCGTCG

TCGAGCCTGCTTCATTCCTGCCTCAGGTGCATAACTTTGCATGAAAAGTCCAGATTAGGGCAGAT

TTTGAGTTTAAAATAGGAAATATAAACAAATATACCGCGAAAAAGGTTTGTTTATAGCTTTTCGC

CTGGTGCCGTACGGTATAAATACATACTCTCCTCCCCCCCCTGGTTCTCTTTTTCTTTTGTTACT

TACATTTTACCGTTCCGTCACTCGCTTCACTCAACAACAAAA

-continued

*Pichia pastoris* pTEF1 promoter (SEQ ID NO: 10)
ATAACTGTCGCCTCTTTTATCTGCCGCACTGCATGAGGTGTCCCCTTAGTGGGAAAGAGTACTGA

GCCAACCCTGGAGGACAGCAAGGGAAAAATACCTACAACTTGCTTCATAATGGTCGTAAAAACAA

TCCTTGTCGGATATAAGTGTTGTAGACTGTCCCTTATCCTCTGCGATGTTCTTCCTCTCAAAGTT

TGCGATTTCTCTCTATCAGAATTGCCATCAAGAGACTCAGGACTAATTTCGCAGTCCCACACGCA

CTCGTACATGATTGGCTGAAATTTCCCTAAAGAATTTcTTTTTCACGAAAATTTTTTTTTACAC

AAGATTTTCAGCAGATATAAAATGGAGAGCAGGACCTCCGCTGTGACTCTTCTTTTTTTTCTTTT

ATTCTCACTACATACATTTTAGTTATTCGCCAAC

Heme biosynthesis enzyme 1-ALA Synthase (SEQ ID NO: 11)
ATGGAGTTTGTCGCCCGTCAGTCCATGAATGCCTGTCCCTTTGTCAGGTCAACTTCTACCCACCA

TTTGAAGAAGTTGGCAGCAAACAGTTCTCTAGCTGCTACTGCTAGTCATTGTCCCGTGGTTGGCC

CTGCTCTCCAACAGCAGAGATACTACTCTCAACCTTCCAAGCCAGCCCAAGCCCAAACCTCCGAC

ATTGCTACTGGGATCAAGAAGGATGTTTCTCCGATCCGTATGGACTCTAATGAAACCGCCTTTGA

TTACAATGGAATGTATGAGTCTGATCTTGCGAATAAACGTAAAGATAACTCGTATCGTTATTTCA

ATAACATCAACCGTCTAGCCAAGGAGTTTCCCAAGGCACATCGCCAGACCGAAGATGACAAGGTG

ACCGTCTGGTGCTCTAACGACTACTTAGGAATGGGTAGGCATCCTGAGATTATCAAAACCATGAA

GGCTACCATGGACAAGTACGGTTCCGGAGCAGGAGGAACTAGGAACATTGCAGGTCATAACCACG

CCGCTATCAATTTGGAAAGCGAGTTGGCTTGCTTGAACAAGAAGGAAGCGGCTCTGGTGTTTTCA

TCATGTTTCATAGCTAACGATGCAATCATCTCGTTGTTGGGACAAAAAATCAAAAATTTGGTCAT

TTTCTCTGACCAGTCGAATCATGCTTCCATGATATTGGGTGTGCGTAACTCCAAAGCGAAGAAGC

ACATCTTCAAGCACAACAATTTGAAGGATCTGGAGTCGCAGTTAGCTCAGTACCCCAAGTCGACT

CCTAAACTGATCGCCTTCGAGTCAGTTTACTCTATGTGTGGATCTGTGGCTCCCATTGAGAAGAT

TTGCGATTTGGCTAAAAGGTACGGTGCCCTCACCTTCTTGGATGAAGTTCATGCTGTTGGAATGT

ATGGTCCTCATGGACAGGGTGTAGCTGAGCATTTGGACTTTGATCTGCATTTACAGTCTGGAATC

GCCAGTCCTAGCGTGGTGGACAAACGCACCATATTGGATCGTGTCGACATGATTACTGGTACTTG

CGGAAAGTCATTTGGTACTGTTGGAGGTTACGTTGCTGGTAGTGCCAACCTAATTGATTGGTTAA

GATCCTATGCGCCAGGTTTCATTTTCACTACCACACTTCCTCCTGCTATCATGGCTGGTACAGCC

ACTTCTGTTCGTATTGTTAGGGCCGACATTGAGGCCCGTATCAAGCAACAGCTTAATACTCGCTA

CGTCAAAGACTCATTTGAAAACCTTGGTATTCCAGTCATTCCAAACCCAAGTCACATTGTTCCTG

TTCTAGTTGGAAATGCTGCAGATGCCAAGAAGGCATCCGATATGTTAATGAACAAACACCGTATT

TATGTTCAAGCTATTAACTACCCTACTGTGCCTGTCGGTGAAGAACGACTAAGGATTACTCCTAC

TCCAGGTCATGGAAAGGAGATTTGTGACCAGCTGATCAGCGCTGTCGACGATGTTTTTACTGAGC

TTAATTTACCAAGAATCAACAAATGGCAGTCCCAAGGTGGTCATTGCGGTGTTGGTGATGCTAAT

TACGTACCAGAACCCAATCTGTGGACTCAGGACCAGCTCAGCTTGACAAACCAAGACTTGCACTC

CAATGTGCACAACCCAGTGATTGAGCAGATCGAAACCTCATCAGGAGTCAGATTGTAG

Heme biosynthesis enzyme 2-ALA dehydratase (SEQ ID NO: 12)
ATGGTGCATAAGGCTGAATACTTGGACGACCACCCAACTCAGATTTCCAGCATTCTTTCAGGAGG

TTACAACCACCCATTACTTCGTGAATGGCAACATGAACGTCAACTCAACAAAAACATGTTCATCT

TTCCCCTGTTTGTCACAGATCGACCAGACGAAGAAGAACTTATTCCTAGTCTACCTAATATCAAG

AGGTTTGGCGTTAACAAGTTGATTCCTTATGTAGGAGGTTTGGTTTCCAAAGGATTGAGGGCGGT

GATCCTATTTGGTGTTCCTCTGAAGCCCGGTGTGAAAGATGAAGAAGGAACGGCCGCTGATGATC

-continued

```
CAGAGGGACCTGTTATCCAAGCCATCAAACACTTGAGAAAGAACTTTCCTGACCTGTATATCATC
ACCGATGTCTGTCTATGTGAGTACACCAGCCATGGACATTGTGGAATACTATATGAGGATGGCAC
TATCAACAGAGAGCTCTCAGTCCGTCGTATTGCTGCTGTAGCTGTCAAATATGCTCAAGCTGGAG
CCAACTCTGTGGCTCCTTCTGATATGACTGACGGCAGAATAAGAGATATTAAAGAAGGCTTACTA
AGTGCAGGACTGGCACATAAAACGTTTGTTATGTCCTACGCTGCAAAATTCTCTGGTAATTTGTA
TGGCCCTTTCAGAGATGCTGCAGGTTCCTGTCCATCTCAAGGGGACAGAAAATGTTACCAGCTTC
CTTCTGGAGGAAAAGGGTTGGCCCATCGTGCTCTGATTCGTGATATGAATGAAGGCACTGATGGA
ATTATTGTCAAACCATCTACATTCTATTTGGACATTGTCGCTGATGCTTATCAGCTTTGTAAAGA
CTATCCTATCTGCTGTTACCAGGTTTCTGGAGAGTACGCCATGCTACATGCAGCGGCAGAGAAGA
ATATTGTTGATCTGAAATCAATCGCTTTTGAAGCTCATCAAGGATTCTTGCGGGCTGGAGCTCGT
TTAATCATTAGTTACTTTACCCCTGAATTCCTGGAGTGGTTATCTGAATGA
```

Heme biosynthesis enzyme 3-Porphobilinogen deaminase (SEQ ID NO: 13)
```
ATGAACCAAATCGAACAGAGCGGACCCATTGATTGCAGTTCCTTGAAATTGGGGTCCCGAAAGTC
CGCTCTGGCTATAATCCAGGCAGAAATCGTCCGCCAATTGATATTGAAAGAATACCCTGAATTGG
AGACGAAGTTGGTCAGTGTGTCCACCCTGGGGGACCAAGTCCAGAATAAAGCACTTTTCACGTTT
GGAGGAAAATCTTTGTGGACCAAAGAACTTGAGATGTTGTTGTTGGAGAGTGTGGGAGGATTTGA
CCAAATAGACATGATTGTACACTCGTTGAAAGACATGCCAACTCATTTACCAGACGAATTTGAGC
TGGGTTGCATTATTGAAAGAGAAGACCCTAGAGACGCTTTGGTCGTGCAAGATGGTTTATCTTAC
AAGTCATTGGCCGACCTTCCAGAGGGAGCTGTGGTCGGTACGTCTTCGGTTAGAAGATCGGCTCA
ACTACTGAAGAATTTCCCTCATCTGAAATTCAAATCTGTTAGAGGAAACCTTCAGACCAGACTAA
GAAAATTAGATGATCCAGATTCCGAGTACTGCTGTCTCCTCCTTGCAGCAGCCGGTTTAATCAGG
ACAGGCTTACAACACAGAATTTCAATGTATTTGAACGACGATGTGATGTACCACTCCGTCGGACA
AGGAGCATTAGGAGTAGAGATCAGAAAAGGTGACCAATTCATGAAAAATATCTGTGAAAAGATTG
GGCATAGAACCACCACCCTTCGTTGTCTTGCAGAGAGCACTGCTGAGATATCTAGAGGGAGGC
TGCTCGGTGCCAATTGGGGTCTCCACTATTTATAGCGAGGATACGAAGGAACTTACCATGAACTC
CCTAGTCGTCAGTTGTAACGGTCGTGACTCGGTAACAGAATCAATGACTGAAGTCGTGACTACTG
AAGAGCAAGCTGAAGATTTCGGTGAAAGGCTGGCCCAGAAGCTCATAGATCAAGGTGCGAAACGC
ATTCTTGACGAGATCAACTTCAACAAGATCAAAGAGATTAAGGAAGAGGGTTTACATTAA
```

Heme biosynthesis enzyme 4-Uroporphyrinogen III synthase (SEQ ID NO: 14)
```
ATGCCAAAAGCCATTCTTCTGAAGAATAAAACTACACCGAAGGATCCTTATCTGGAGAACTTCGT
AAGTAGTGGCTACTCGACCGATTTCGTACCACTTTTAGATCATATTCACATGGAGAAATCTGAGA
TCATCGCATTTCTCAAGACTGACTACTTTTTGCATAAAACTTTGGCGTTTATTATTACGTCCCAA
AGAGCTGTAGAAATGCTGAATGAGTGTATGCAAATACTGAGACGTACTGATCCTGAAATTACACA
AATCATCTATAGTAAACCTGTCTATACAGTTGGCCCTGCCACCTACAGAATACTTGCGGATGCTG
GCTTCGTGGATCTACGAGGCGGAGATAAGGCAGGAAACGGATCCATTCTAGCCCAGATAATTTTG
AATGATGACATTTACACTGGAATTGAAGATTCTGACAAGCATATAACGTTTTTCACGGGAGAAAC
AAGGAGAGACATAATTCCCAAATGTTTACTCTCTAACAACTTTCAACTTTACGAAAAGATTGTCT
ACAAGACTCTTCCTAGGGATGATATCGTGACTAGATTCAAGTCTGCCGTTGACAGCATCGACCAA
TCGCAAAGAAGTTCCAGTTGGGTGGTCTTCTTTTCGCCTCAAGGAACAGAGGACATTGTAACGTA
TCTTCAACACACCAAAGACCAATTTAATATTGCATCTATCGGGCCAACCACAGAAAAATACCTTC
```

Heme biosynthesis enzyme 5-Uroporphyrinogen III decarboxylase
(SEQ ID NO: 15)
ATGAGTAGATTTCCAGAACTGAAGAATGACCTTATTTTAAGGGCAGCTCGTGGTGAAAAAGTTGA

ACGTCCCCCAATATGGATTATGAGACAGGCCGGAAGATATCTTCCGGAGTACCATGAGGTCAAAG

GAGGTAGGGACTTCTTTGAAACTTGCAGGGATGCTGAGATTGCTTCTGAAATTACTATCCAGCCG

ATTACGCATTTTGACGGTCTGATCGATGCAGCTATTATCTTCAGTGATATCTTGGTGATTCCTCA

AGCTATGGGCATGGAAGTTAAGATGGTGGACAAAGTTGGCCCACAGTTCCCCAATCCGCTAAGAA

AACCGTCTGACTTGGATCATTTGAAAAAGACGTTGACGTTTTGAAGGAACTCGATTGGGCCTTC

AAAGCTATCTCATTGACCAGAAAAAAACTCAATGGACGAGTGCCTTTGCTTGGATTTTGTGGTGC

TCCTTGGACTCTACTGGTTTATATGACTGAAGGAGGCGGTACCAAGATGTTTCGATTTGCAAAAG

AGTGGATCTACAAGTTTACCAAGGAATCTCATCAATTACTCCAACAGATCACTGACGTTGCAGTT

GAATTCTTAGCTCAGCAAGTTGTTGCAGGTGCCCAAATGTTACAAGTTTTTGAATCTTGGGCGG

TGAATTGGGGCCTGATGAATTCGATGAGTTTTCTTTGCCTTATTTGAGACAGATTTCCTCTAAAC

TTCCCCTGAGGTTGAAGGAACTTGGAATCACAGAGAATGTTCCCATAACTGTCTTTGCTAAAGGC

TCTTGGTACGCCTTGGAGCAATTGTGCGACAGTGGTTATGATGTTGTCTCGTTGGATTGGTTATT

CCGTCCAAGTGATGCTGTCCAGATTGCTAACGGAAGAATCGCATTGCAAGGTAATCTTGACCCTG

GAACCATGTACGGCTCCAAAGAAACCATTTCCAAGAAAGTGGACAAAATGATCAAGGGTTTTGGT

GGAGGAAAGCAAAACTACATAATTAATTTTGGACACGGCACTCATCCATTCATGGATCCAGAACA

GATCAGATGGTTCTTACAAGAATGTCATCGCATTGGATCTCAATAG

Heme biosynthesis enzyme 6-Coproporphyrinogen III oxidase
(SEQ ID NO: 16)
ATGGCCATCGACTCTGATATCAATCTAAGCTCTCCCAATGATTCCATCCGTCAAAGGATGTTCGA

GCTTATCCAGCGGAAGCAACTCGAAATTGTCGCTGCATTGGAGGCAATTGAAGGAAACGATACCA

AATTTCGTTCTGATTCTTGGGAAAGAGGAGCCGAAGGTGGAGGAGGAAGATCTATGCTTATTCAA

GATGGAAGAGTGTTTGAAAAGGCTGGTGTAAATATTTCCAAGGTTCATGGCGTATTGCCTCCTCA

AGCTGTGAGCCAGATGAGAAATGACCACTCCAAGCTAGATCTGCCTGCGGGAACCTCTCTGAAGT

TCTTTGCCTGTGGGCTTTCGTTGGTCATTCATCCCCATAATCCCCATGCTCCAACTACCCATCTG

AATTATCGCTACTTCGAAACTTGGGATGAAACTGGAAAGCCTCACACCTGGTGGTTTGGGGCGG

TGCTGATTTAACGCCTTCGTACCTGTATCCCGAGGATGCCAAGCAATTCCATCAAGCCCATAAGG

ATGCCCTGGACAAACACGATGTTAGCTTGTACCCGAGATTCAAAAAGTGGTGTGATGAATACTTT

CTGATCAAACATCGAAATGAAACTAGAGGTATTGGGGGTATTTTCTTTGATGATTTTGACGAGTT

TGATGCTGAGAGGTCCCTGAAGTTGGTTGAAGATTGTTTCAATGCTTTCTTGGAATCTTATCCCG

CTATCACTCGAAAAAGGATGGACACCCCTTCAACTGATGCTGAGAAGAACTGGCAACAAATTAGA

AGAGGAAGATATGTCGAATTCAACTTAGTATTGGATAGAGGTACTCAATTTGGTTTGAGAACGCC

TGGATCTCGTGTTGAAAGTATTTTGATGTCGTTGCCAAGAACAGCTGGTGGGTCTATGATCATC

ATCCAGAGCCTGGCTCCAGAGAAGAGGAGTTATTGCAGGTACTACAAAATCCTATTGAATGGGTA

TGA

Heme biosynthesis enzyme 7-Protoporphyrinogen oxidase
(SEQ ID NO: 17)
ATGCTGAAAAGTCTTGCACCAAATTCCTCAATTGCCGTTTTAGGTTCAGGGATATCTGGATTGAC

TTTCAGCTTTTTTTGAATCGGTTGCGTCCCGATGTTAAGATCCATATCTTTGAAAAATCCAAGC

AGGTTGGAGGATGGATCAGATCAGAAGAGCATGAAACTTTTCATTTTGAAAAGGGACCCAGAACT

```
TTGAGAGGCACAAATACGGGTACCTTGATGTTGTTGGATCTTCTTACCAAGATAGGAGCAAATGA

CAAGGTCCTGGGACTGCACAAAGATTCTCTTGCTAATAAAAAGTATCTGTTGTCCCCGTTCTCAG

ATGTTCACGGAAACAACGCAAAGCTTCTTCAAGTGCCACAGGATTTCAGCTCTTTTGTAAAGTTC

ATGTTTGACCCGTTGTCTAAGGATCTCATTCTCGGTCTTTTGAAAGAACCATGGCAACCAAAATT

AAAGTATTCAGATGAGTCGGTTGACCATTTTTTCAACAGAAGATTTGCTACCAAACTATCAGAGA

ATATCGTCAGCGCAATTGTGCATGGAATCTATGCGGGCGACGTGAAGAAGTTAAGTGTGAAAGCC

ATCTTCCCTAGGCTCCCTGAGATGGAACAGGAAAGTGGCTCTATTATAAGGTATATGATCGCCCA

ATACAGGACAAAAAGAACGTCAAACAAAAGTTGACCCTTTTTGGCAGATTATGAAAAATTGA

TCGGTACATCTTTGAGTTTCAAAAATATTTCTTTGTTTCTGAAAAACTTTCCCATGCTGAGTTTT

CAGGGTGGACTACAGAAACTTCCCATCTCATTGAAGAACCATTTATCACAGATTGAAAACATCAA

GTTTCATTTTGACAGCAAAATCAAAAACATTGCTTTGGAGAGCGGTAAGGTGGCATTGACTGACC

ATGATCAGGTTTATCTTGTTGACCATGTGAGATCTACCATTAATACCAACGAATTGGCCAAAATC

ATTTCACCCGTTGTTCCAAGTTCTACTAAGAAAAAATCCGTTTTCAAATCCAAAGCGAATGGCCC

AGGGCTGGTCAAATGTTTGAGCTGGCTACACTATACAAATATACTAATGTGCAACATTTATATAC

CTAAGCACGTCTCAAAATCTATCACCGGATTTGGATACTTGGTTCCTCGATCAATGTCTTCTCAG

GCATCCAAACTTCTCGGTGTCATATTTGACTCAGACATCGAGACTGCAATGACTCCTAATTTTAC

AGAGGCCAACATTACGGCGATAAACAGTAACTCTGCATCTCCCAAGCAACTCCAAAAGTTTTCTG

ACCAATTCGTCAATAATGATCTCCCTAAATACACCAAGTTGACGCTAATGCTTGGAGGTCATTAT

CTCAAGTCGGAGGCAGACATGCCCGGTTCCGCAGAGAGTAAACATGCTGTCAAGGCGATTCTGTC

AAATCACCTGAATATTGATCTAGATGAGTTTGCATCTTTGCCAGACTTCAAGATGGAAATCACCA

AGATCCCCAACTGCATTCCCCAATATGAAGTTGGGTATCTTGATCTCAAGAGAAAGGTTCAGAAT

GCAGCCTCCAAAGAGTTCAACGACCAAATAAGTTTTGGAGGCATGGCATTTGGTGATGGTGTGGG

GATCCCTGACTGTGTCCAGAATGCATTCAAAGATTCGGCTACCCTCAGTGGCATTTAA
```
Heme biosynthesis enzyme 8-Ferrochelatase (SEQ ID NO: 18)
```
ATGCTTAACCGTCGTTTCCAATCTACCGTGTCCTCGAGTCTGAACAAGGGCACTGGAATAGTGTT

CATGAATATGGGTGGTCCCTCCACTGTCAAGGAAACCTATGACTTTTTATTTCGTCTTTTCTCGG

ACGGAGATTTAATCCCGTTTGGCAGATTTCAGAACATCCTGGCCCGCTTCATTGCAAGTAGAAGA

ACACCCAAAATTGAATCCTACTACAAAGCTATCGGAGGTGGGTCTCCTATCCGAAAGTGGTCTGA

ATACCAGAGTTCTAAACTATGTGAAAAATTAGACATTATCAGTCCACAATCGGCTCCTCATAAGC

CTTATGTTGCCTTCAGATACGCTAATCCTCTCACTGAAGATACTTTACAAAAGATGAAAAATGAT

GGAATTACTAAGGCCATTGCCTTTTCTCAATATCCGCAATTTAGTTATTCAACCACCGGATCATC

GATTAACGAACTTTACAGGCAATCGAAAATTTTGGACCCTGATCAATCTATTAAATGGACAGTTA

TAGATCGCTGGCCTGACCACCCAGCCTTAGTTAAAACTTTCGCAGCTCATATCAAAGATACTCTA

AACAGATTCAAAACTGAAAATGGACTGACTGACACAAAAGACGTCGTCCTCCAATTCAGTGCTCA

TTCTTTACCAATGGATATTGTCAATAAAGGAGATTCGTATCCTGCAGAAGTCGCAGCGAGTGTCT

TTGCCATTATGAAAGAACTTAACTTCTCAAATCCTTATAAATTAACCTGGCAATCACAGGTTGGC

CCAAAGCCTTGGCTGGGTGCTCAAACTGAAAAAATTACCAAGCAGCTAGCATCCAGTGATGTTCC

TGGAGTCGTTTTGGTTCCTATTGCCTTTACCTCTGATCATATTGAAACTCTCCATGAACTGGATA

TTGAACTGATTCAAGAACTACCTAATCCTTCAAAAGTAAAGCGAGTTGAATCGTTGAACGGAGAC

CAAACTTTCATTGACTCCTTGGCAGAACTAGTGAAGAGTCACATTGATTCGAAGGTTGTATTTTC
```

```
-continued
CAACCAGTTGCCATTGGATTCCATGCTGGGAGTAGTGTCAGATAATTCCCTCACAGATCCAAAAG

AGTTTTTCAGAGCCCATTGA
```

Part C. Results and Discussion

Example 24—Characterization of Strain MXY0183

Optimum growth conditions for Strain MXY0183 include a target pH of 3.0 to 6.0 and temperatures of 28-35° C. In order to produce the LegH protein, strain MXY0183 must be alive and growing aerobically for a period of 6 days.

Figure 8:
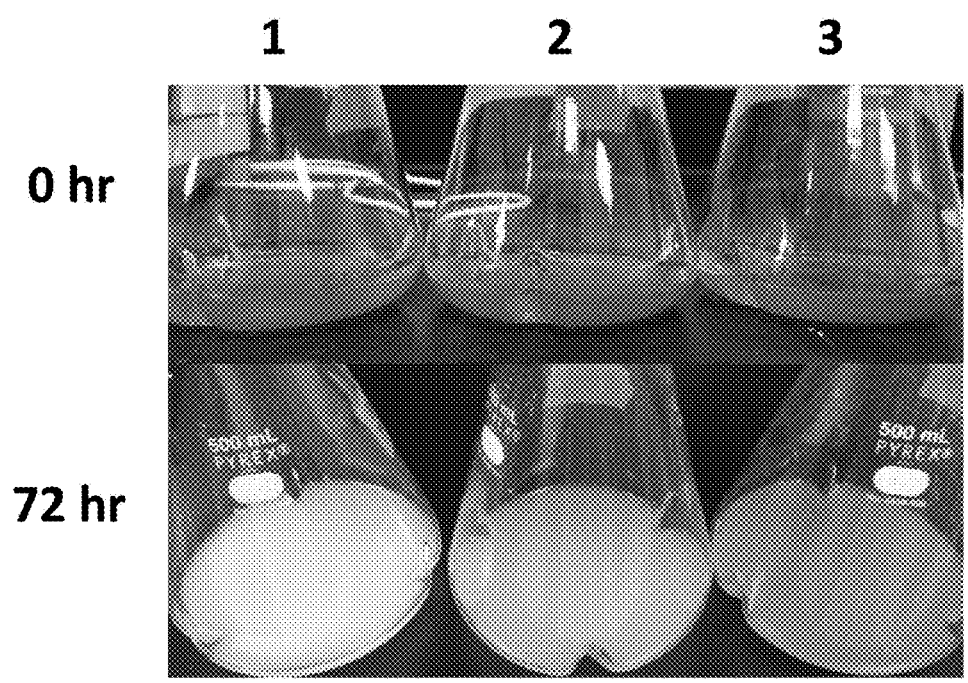
FIG. 8 is a photograph showing the phenotypic changes associated with strain, MXY0183. Shake flasks at the start of induction (0 hr) and 72 hr post-induction are shown. 1, MXY0051; 2, MXY0118; 3, MXY0183.

Expression of the genes associated with strain MXY0183 resulted in phenotypic changes to the strain. FIG. 8 shows photographs of shake flasks at the start of induction (0 hr) and 72 hr post-induction. The flasks designated #1 contain the host strain, MXY0051. The flasks designated #2 and #3 contain one of the intermediate strains (i.e., MXY0118, containing >10 copies of the LegH gene and the ALA dehydratase from the heme biosynthetic pathway) and the production strain (i.e., MXY0183, containing >10 copies of the LegH gene and the 8 enzymes from the heme biosynthetic pathway), respectively. The characteristic red color in flask #3 after 72 hours demonstrates the production of heme-bound LegH.

Figure 9:
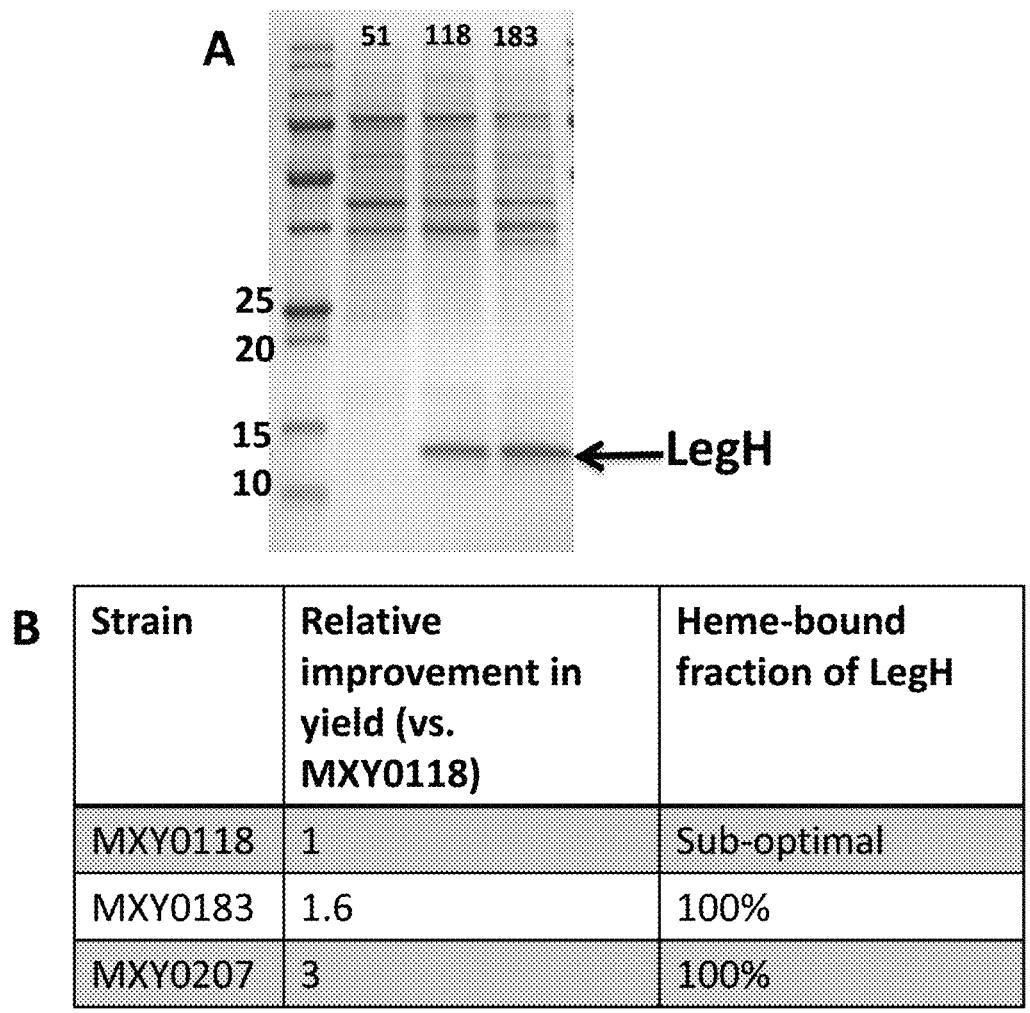
FIG. 9 shows the production of LegH from the modified *P. pastoris* strains. Panel A is a SDS gel showing lysates from *P. pastoris* strains grown in shake flasks: 51, MXY0051; 118, MXY0118; 183, MXY0183. Panel B is a table comparing LegH production from strains MXY0118, MXY0183, and MXY0207.

After growing in shake flasks, the P. pastoris strains indicated above, MXY0051, MXY0118, and MXY0183, were lysed and the proteins run on a SDS gel (FIG. 9A). The arrow shows the position of the LegH protein. A comparison of LegH production in strain MXY0183 and in strain MXY0118 is shown in FIG. 9B, which demonstrates the efficiency of heme loading of the LegH protein by the MXY0183 strain.

Example 25—Characterization of Strain MXY0207

Figure 10:
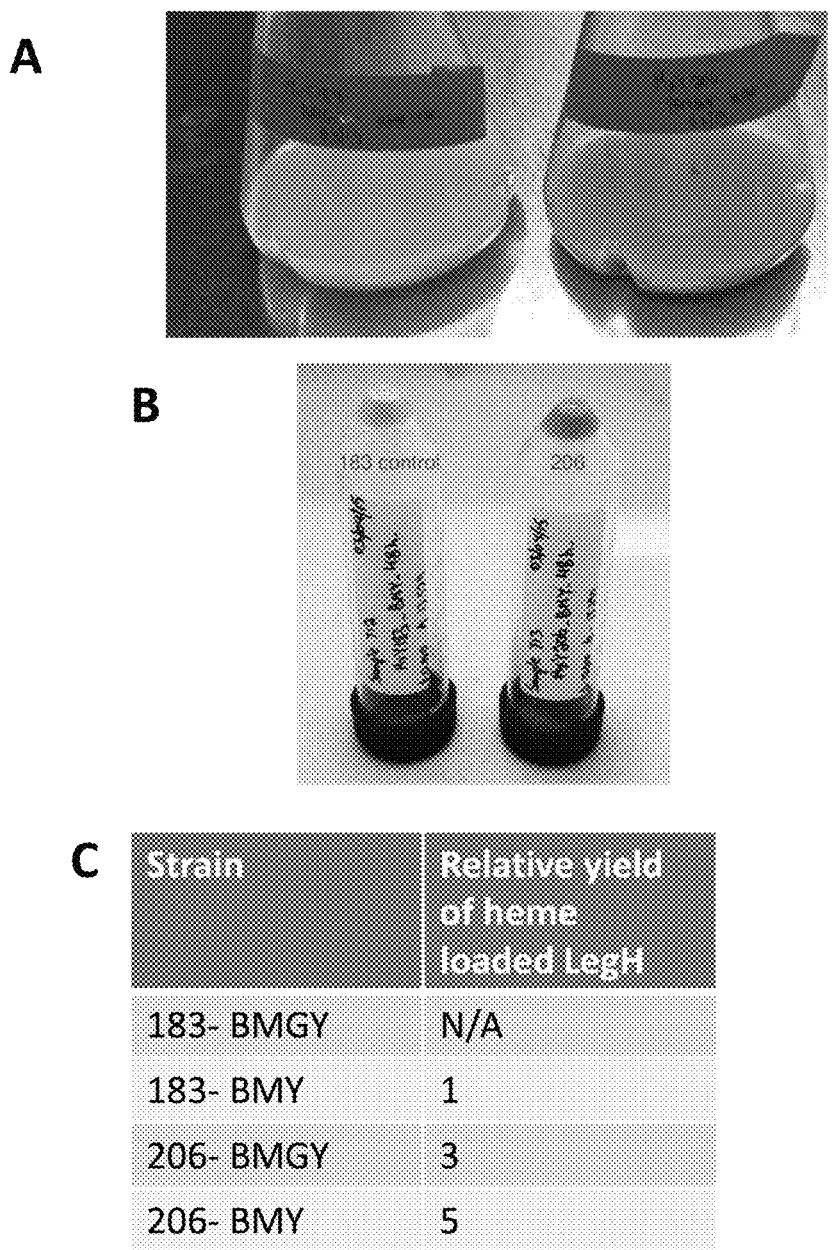
FIG. 10 shows data from experiments with strain MXY0206. Panel A is a photograph of shake flask cultures of strains MXY0183 (left) and MXY0206 (right) after 48 hr of growth in repressing carbon source. Panel B is a photograph of cell pellets from shake flask cultures of strains MXY0183 (left) and MXY0206 (right) after 48 hr of growth in BMY media. Panel C is a graph showing the relative yield of heme-loaded LegH (in the absence of any induction agent).

Experiments were then performed to determine the benefits of overexpressing the transcriptional activator, Mxr1, in the presence of the genes encoding the 8 enzymes involved in heme biosynthesis. Strain MXY0183, which contains >10 copies of the LegH sequence and the genes encoding the 8 enzymes involved in heme biosynthesis, and sister strains MXY0206 and MXY0207, which contain >10 copies of the LegH sequence, the genes encoding the 8 enzymes involved in heme biosynthesis, and the Mxr1 transcriptional activator, were grown in shake flask cultures in the presence of glycerol, which is a repressing carbon source for these strains. Photographs of the shake flask cultures after 48 hr are shown in FIG. 10A, and photographs of the pellets from cells grown on BMY media for 48 hours with no additional source of carbon are shown in FIG. 10B; these experiments demonstrated that significant expression of transgenes (e.g. heme enzymes) under the control of the AOX1 promoter occurs in the absence of an inducing carbon source when a repressing carbon source is consumed in the growth medium of a strain in which Mxr1 is also expressed from the AOX1 promoter. The relative yield of heme-loaded LegH, when shake flask cultures were grown in the absence of induction agent, is shown in FIG. 10C. These experiments demonstrated that significant production of a recombinant, heme-loaded protein is accomplished from AOX1 promoter-driven transgenes in the absence of methanol induction in Pichia strains in which Mxr1 expression is also driven by the AOX1 promoter.

Select strains were grown in 2 L fermenter tanks, and the relative yield of LegH and heme-loaded LegH was determined (FIG. 11). Compared to strain MXY0183, the MXY0207 strain produced even more LegH and was able to produce enough heme to heme-load the LegH protein very effectively.

Example 26—Characterization of Strain MXY0291

As described above in Examples 18-20, strain MXY0291 was constructed to recapitulate the LegH production ability of MXY0207, while being free of antibiotic resistance genes. It was determined that strain MXY0291 contained ~16 copies of LegH var3, Mxr1 and 7 of the 8 heme biosynthetic enzymes. When grown in 2 L fermenter tanks, this strain showed improved LegH yield compared to MXY0207. This improvement was seen both in induction media containing methanol/glycerol and methanol/dextrose (D-glucose) (FIG. 11).

Example 27—Characterization of Hybrid Promoter Strains

Additional copies of soybean leghemoglobin (LegH) were expressed under three different constitutive promoters, pGAP, pGCW14 and pTEF1, in a strain that already contains several copies of LegH, all heme biosynthetic enzymes, and the transcriptional factor Mxr1 under control of the promoter, pAOX1 (referred to above as MXY0291). When induced by methanol in the presence of dextrose (i.e., D-glucose), the constitutive promoters and pAOX1 drive expression of LegH while only the pAOX1 promoter drives expression of the heme enzymes. This leads to further improvement in LegH yield compared to previous strain MXY0291 (FIG. 11).

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A nucleic acid construct comprising:
a first nucleic acid encoding a transcriptional activator operably linked to a promoter element, wherein the promoter element comprises a second nucleic acid that binds to the transcriptional activator,
wherein the transcriptional activator is selected from the group consisting of methanol expression regulator 1 (Mxr1), alcohol dehydrogenase regulator 1 (Adr1), transcriptional regulation of methanol induction 1 (Trm1), and transcriptional regulation of methanol induction 2 (Trm2).

2. The nucleic acid construct of claim 1, wherein the promoter element is a methanol-inducible promoter element.

3. The nucleic acid construct of claim 1, wherein the promoter element is selected from the group consisting of alcohol oxidase 1 (AOX1), methanol oxidase (MOX), alcohol oxidase (AOD1), methanolica alcohol oxidase 1 (MOD1), methanolica alcohol oxidase 2 (MOD2), dihydroxyacetone synthase (DHAS), and peroxin 8 (PEX8).

4. The nucleic acid construct of claim 1, wherein the promoter element is AOX1.

5. The nucleic acid construct of claim 1, wherein the transcriptional activator is Mxr1.

6. The nucleic acid construct of claim 5, wherein the promoter element is formaldehyde dehydrogenase (FLD1).

7. The nucleic acid construct of claim 5, wherein the promoter element is selected from the group consisting of AOX1, DHAS, and PEX8.

8. The nucleic acid construct of claim 1, wherein the transcriptional activator is Adr1.

9. The nucleic acid construct of claim 8, wherein the promoter element is MOX.

10. The nucleic acid construct of claim 1, wherein the transcriptional activator is Trm1 or Trm2.

11. The nucleic acid construct of claim 10, wherein the promoter element is AOD1.

12. The nucleic acid construct of claim 1, further comprising a termination sequence.

13. The nucleic acid construct of claim 1, wherein the promoter element comprises a plurality of the second nucleic acid that bind to the transcriptional activator.

14. The nucleic acid construct of claim 1, further comprising a third nucleic acid encoding a second transcriptional activator operably linked to a second promoter element, wherein the second promoter element comprises a fourth nucleic acid that binds to the second transcriptional activator, and the second transcriptional activator is different from the transcriptional activator encoded by the first nucleic acid.

15. The nucleic acid construct of claim 14, wherein the second transcriptional activator is selected from the group consisting of Mxr1, alcohol dehydrogenase regulator 1 (Adr1), transcriptional regulation of methanol induction 1 (Trm1), and transcriptional regulation of methanol induction 2 (Trm2).

16. The nucleic acid construct of claim 14, wherein the second transcriptional activator is methanol-induced transcription factor 1 (Mit1).

17. The nucleic acid construct of claim 1, wherein the promoter element is formaldehyde dehydrogenase (FLD1).

18. A methylotrophic yeast cell comprising a nucleic acid construct comprising:
a first nucleic acid encoding a transcriptional activator operably linked to a promoter element,
wherein the promoter element comprises a second nucleic acid that binds to the transcriptional activator,
wherein the transcriptional activator is selected from the group consisting of methanol expression regulator 1 (Mxr1), alcohol dehydrogenase regulator 1 (Adr1), transcriptional regulation of methanol induction 1 (Trm1), and transcriptional regulation of methanol induction 2 (Trm2), and
wherein the nucleic acid construct is stably integrated into the genome of the methylotrophic yeast cell.

19. The methylotrophic yeast cell of claim 18, wherein the methylotrophic yeast cell is from a *Pichia* species, a *Candida* species, a *Hansenula* species, or a *Torulopsis* species.

20. The methylotrophic yeast cell of claim 19, wherein the methylotrophic yeast cell is a *Pichia pastoris* cell, a *Hansenula polymorpha* cell a *Candida boidinii* cell, or a *Pichia methanolica* cell.

21. The methylotrophic yeast cell of claim 18, further comprising a second nucleic acid construct encoding an exogenous protein operably linked to a second promoter element,
wherein the second promoter element comprises a third nucleic acid that binds to the transcriptional activator.

22. The methylotrophic yeast cell of claim 21, wherein the second nucleic acid construct encoding the exogenous protein is a nucleic acid construct encoding a dehydrin, a phytase, a protease, a catalase, a lipase, a peroxidase, an amylase, a transglutaminase, an oxidoreductase, a transferase, a hydrolase, a lyase, an isomerase, a ligase, or an antibody.

23. The methylotrophic yeast cell of claim 21, wherein the second nucleic acid construct encoding the exogenous protein is a nucleic acid construct encoding an enzyme involved in a pathway for production of ethanol, lactic acid, butanol, adipic acid, or succinic acid.

24. The methylotrophic yeast cell of claim 21, wherein the second nucleic acid construct encoding the exogenous protein is a nucleic acid construct encoding a heme-containing protein or a nucleic acid construct encoding at least one protein involved in heme biosynthesis.

25. The methylotrophic yeast cell of claim 21, wherein the exogenous protein is a heterologous protein.

26. The methylotrophic yeast cell of claim 18, further comprising a second nucleic acid construct encoding a second transcriptional activator operably linked to a second promoter element, wherein the second promoter element comprises a third nucleic acid that binds to the second transcriptional activator, and the second transcriptional activator is different from the transcriptional activator.

27. The methylotrophic yeast cell of claim 26, wherein the second transcriptional activator is selected from the group consisting of Mxr1, Adr1, Trm1, and Trm2.

28. The methylotrophic yeast cell of claim 26, wherein the second transcriptional activator is methanol-induced transcription factor 1 (Mit1).

29. A methylotrophic *Pichia* yeast cell comprising:
a nucleic acid construct encoding a methanol expression regulator 1 (Mxr1) transcriptional activator operably linked to an alcohol oxidase 1 (AOX1) promoter element, wherein the AOX1 promoter element comprises a second nucleic acid, wherein the second nucleic acid comprises a plurality of nucleic acid sequences that bind to the Mxr1 transcriptional activator; and a nucleic acid construct encoding an exogenous protein operably linked to a second AOX1 promoter element, wherein the second AOX1 promoter element comprises a third nucleic acid, wherein the third nucleic acid comprises a plurality of nucleic acid sequences that bind to the Mxr1 transcription activator.

* * * * *

UNITED STATES PATENT AND TRADEMARK OFFICE
CERTIFICATE OF CORRECTION

PATENT NO. : 11,319,544 B2
APPLICATION NO. : 16/123121
DATED : May 3, 2022
INVENTOR(S) : Shankar et al.

Page 1 of 1

It is certified that error appears in the above-identified patent and that said Letters Patent is hereby corrected as shown below:

In the Claims

Claim 1: In Column 87, Line 6, please delete "activator" and insert -- activator and --, therefor.

Claim 19: In Column 88, Line 16, please delete "*polymorpha* cell" and insert -- *polymorpha* cell, --, therefor.

Signed and Sealed this
Nineteenth Day of July, 2022

Katherine Kelly Vidal
*Director of the United States Patent and Trademark Office*

SEQUENCE LISTING

<160> NUMBER OF SEQ ID NOS: 58

<210> SEQ ID NO 1
<211> LENGTH: 3486
<212> TYPE: DNA
<213> ORGANISM: Komagataella phaffii

<400> SEQUENCE: 1

```
atgcgagacc gcggccgcat gagcaatcta cccccaactt ttggttccac tagacaatct      60
ccagaagacc aatcacctcc cgtgcccaag gagctgtcat caatgggac cacaccctca     120
ggaaagctac gcttatttgt ctgtcagaca tgtactcgag catttgctcg tcaggaacac     180
ttgaaacgac acgaaaggtc tcacaccaag gagaaacctt tcagctgcgg catttgttct     240
cgtaaattca gccgtcgaga tctgttattg agacatgccc aaaaactgca cagcaactgc     300
tctgatgcgg ccataacaag actaaggcgc aaggcaactc gtcggtcttc taatgccgcg     360
ggttccatat ctggttctac tccggtgaca acgccaaata ctatgggtac gcccgaagat     420
ggcgagaaac gaaaagttca gaaactggcc ggccgccggg actcaaatga acagaaactg     480
caactgcaac aacaacatct acagcaacaa ccacagttgc aataccaaca atctcttaag     540
cagcatgaaa atcaagtcca gcagcctgat caagatccat tgatatcccc gagaatgcaa     600
ttattcaatg attccaacca tcacgtaaac aatttgtttg atcttggact aagaagagct     660
tccttctccg ccgttagtgg aaataattat gcccattatg tgaataattt tcaacaagat     720
gcctcttcta ccaatccaaa tcaagattca aataatgccg aatttgagaa tattgaattt     780
tctaccccac aaatgatgcc cgttgaagat gctgaaactt ggatgaacaa catgggtcca     840
attccgaact tctctctcga tgtgaacagg aacattggtg atagctttac agatatacaa     900
cacaagaatt cagagcctat tatatccgaa ccgcccaagg acaccgctcc aaacgacaag     960
aagttgaatg ctactctttt tacgaagcc cccatcaagc cattagaatc cctatttct    1020
gtcaggaata caaagagaaa caagtataaa acaaatgacg actctccaga caccgtggat    1080
aataactccg caccggctgc taataccatt caagaacttg agtcttcttt gaatgcatcc    1140
aagaattttt gcttgccaac tggttattcc ttctatggta atttggacca acagactttc    1200
tctaacacgt tatcatgcac ttcttctaat gccacaattt cgcccattct actcgataac    1260
tccattaata ataactccac tagtgacgtg agaccagaat ttagaacaca agtgtcacc    1320
tctgaaatga gtcaagcccc tccccctcct caaaaaaaca actcgaaata ttccaccgaa    1380
gttctttta ccagcaacat gcggtcgttt attcactacg ctctttccaa gtatccttt    1440
attggtgtgc ccactccaac tcttccggag aacgaaagac taaatgaata tgctgattca    1500
ttcaccaacc gtttcttaaa tcattatcct ttcatacatg tcacgattct caaagaatac    1560
tccctttca aggcaatttt agatgagaat gagtcgacta agaactggga aaataatcag    1620
ttttacttag agaaccaacg aatatcaatt gtttgtcttc ctcttttggt ggctacgata    1680
ggtgcagtac tatcaaacaa caaaaaggat gcttcgaatt tatacgaagc ttcaaggcgt    1740
tgtattcatg tttacttaga ttccaggaaa agataccca cttccttgtc cgcaaataac    1800
aatgactctc cactttggct aattcaatcc ctgacgttat ctgttatgta tgggttattt    1860
gcggacaatg acattagttt gaatgtcgtg atcagacaag ttaacgcact taattctctg    1920
gtcaagactt cgggcctgaa taggacctca attatagatc ttttcaacat caacaaacct    1980
ttggataatg aactctggaa tcaattcgtg aaaatagagt ccaccgtaag gacaatccac    2040
acgattttc aaatcagttc caacttaagc gccttgtaca atattattcc atcgttgaaa    2100
```

```
attgatgacc taatgattac tctaccagtt cccacaacac tttggcaagc tgattctttt    2160
gtgaaattca aaagtctaag ttacggaaat cagatccctt tcaatatac aagagtacta     2220 cagaatttga ttgattacaa tcagccattg agcgatggaa aattttgta tgaaaaccat     2280 gtaagtgagt ttggactcat atgcctacag aatggtctac accaatacag ctatttccaa    2340
aaattgactg ctgtcaataa cagagaagat gcgctattca caaaggttgt taattcactt    2400
cacagtgggg ataggatgat ttcgaattct gatttgtttc caaagaagat atatcagcag    2460
agttgcttga ttttggactc aaagttgctt aataatttcc tgattgtcaa gagctcattg    2520
aaagtttcga ccggagacgt tagttctttg aataagttaa agaaaacgt gtggcttaaa     2580 aactggaatc aagtgtgtgc tatctattat aacagcttca tgaacattcc tgctcccagt    2640
attcaaaaga agtacaatga catagagttt gtggatgaca tgattaattt gagtctaatc    2700
atcatcaaga ttatgaaact cattttctat aacaatgtca aagacaatta tgaggatgaa    2760
aatgacttca aattgcaaga gttaaattta acatttgaca attttgatga aaaatatcc     2820 ttgaatttga caatattatt cgatatattt ttgatgatct acaagataat taccaattac    2880
gaaaagttta tgaagatcaa acacaagttt aattactaca attctaattc gaatataagc    2940
ttcttgcatc atttcgaact ctcctcggtt atcaataaca cccaaatgaa ccagaatgat    3000
tatatgaaaa cagatattga tgaaaagctt gatcagcttt tccacatcta tcaaacattt    3060
ttccggctgt atctggattt agaaaagttt atgaagttca aattcaacta tcatgacttt    3120
gagacagagt tttcaagtct ctcaatatcc aatatactga acactcatgc tgcttctaac    3180
aatgacacaa atgctgctga tgctatgaat gccaaggatg aaaaaatatc tcccacaact    3240
ttgaatagcg tattacttgc tgatgaagga aatgaaaatt ccggtcgtaa taacgattca    3300
gaccgcctgt tcatgctgaa cgagctaatt aattttgaag taggtttgaa atttctcaag    3360
ataggtgagt cattttttga tttcttgtat gagaataact acaagttcat ccacttcaaa    3420
aacttaaatg acggaatgtt ccacatcagg atataccta aaaaccgact agatggtggt    3480
gtctag                                                              3486
```

<210> SEQ ID NO 2
<211> LENGTH: 1161
<212> TYPE: PRT
<213> ORGANISM: Komagataella phaffii

<400> SEQUENCE: 2

```
Met Arg Asp Arg Gly Arg Met Ser Asn Leu Pro Pro Thr Phe Gly Ser
1               5                   10                  15

Thr Arg Gln Ser Pro Glu Asp Gln Ser Pro Val Pro Lys Glu Leu
            20                  25                  30

Ser Phe Asn Gly Thr Thr Pro Ser Gly Lys Leu Arg Leu Phe Val Cys
        35                  40                  45

Gln Thr Cys Thr Arg Ala Phe Ala Arg Gln Glu His Leu Lys Arg His
    50                  55                  60

Glu Arg Ser His Thr Lys Glu Lys Pro Phe Ser Cys Gly Ile Cys Ser
65                  70                  75                  80

Arg Lys Phe Ser Arg Arg Asp Leu Leu Leu Arg His Ala Gln Lys Leu
                85                  90                  95

His Ser Asn Cys Ser Asp Ala Ala Ile Thr Arg Leu Arg Arg Lys Ala
            100                 105                 110

Thr Arg Arg Ser Ser Asn Ala Ala Gly Ser Ile Ser Gly Ser Thr Pro
```

```
            115                 120                 125
Val Thr Thr Pro Asn Thr Met Gly Thr Pro Glu Asp Gly Glu Lys Arg
        130                 135                 140

Lys Val Gln Lys Leu Ala Gly Arg Arg Asp Ser Asn Glu Gln Lys Leu
145                 150                 155                 160

Gln Leu Gln Gln Gln His Leu Gln Gln Gln Pro Gln Leu Gln Tyr Gln
                165                 170                 175

Gln Ser Leu Lys Gln His Glu Asn Gln Val Gln Gln Pro Asp Gln Asp
            180                 185                 190

Pro Leu Ile Ser Pro Arg Met Gln Leu Phe Asn Asp Ser Asn His His
        195                 200                 205

Val Asn Asn Leu Phe Asp Leu Gly Leu Arg Arg Ala Ser Phe Ser Ala
210                 215                 220

Val Ser Gly Asn Asn Tyr Ala His Tyr Val Asn Phe Gln Gln Asp
225                 230                 235                 240

Ala Ser Ser Thr Asn Pro Asn Gln Asp Ser Asn Asn Ala Glu Phe Glu
                245                 250                 255

Asn Ile Glu Phe Ser Thr Pro Gln Met Met Pro Val Glu Asp Ala Glu
            260                 265                 270

Thr Trp Met Asn Asn Met Gly Pro Ile Pro Asn Phe Ser Leu Asp Val
        275                 280                 285

Asn Arg Asn Ile Gly Asp Ser Phe Thr Asp Ile Gln His Lys Asn Ser
290                 295                 300

Glu Pro Ile Ile Ser Glu Pro Pro Lys Asp Thr Ala Pro Asn Asp Lys
305                 310                 315                 320

Lys Leu Asn Gly Tyr Ser Phe Tyr Glu Ala Pro Ile Lys Pro Leu Glu
                325                 330                 335

Ser Leu Phe Ser Val Arg Asn Thr Lys Arg Asn Lys Tyr Lys Thr Asn
            340                 345                 350

Asp Asp Ser Pro Asp Thr Val Asp Asn Asn Ser Ala Pro Ala Ala Asn
        355                 360                 365

Thr Ile Gln Glu Leu Glu Ser Ser Leu Asn Ala Ser Lys Asn Phe Cys
    370                 375                 380

Leu Pro Thr Gly Tyr Ser Phe Tyr Gly Asn Leu Asp Gln Gln Thr Phe
385                 390                 395                 400

Ser Asn Thr Leu Ser Cys Thr Ser Ser Asn Ala Thr Ile Ser Pro Ile
                405                 410                 415

Leu Leu Asp Asn Ser Ile Asn Asn Asn Ser Thr Ser Asp Val Arg Pro
            420                 425                 430

Glu Phe Arg Thr Gln Ser Val Thr Ser Glu Met Ser Gln Ala Pro Pro
        435                 440                 445

Pro Pro Gln Lys Asn Asn Ser Lys Tyr Ser Thr Glu Val Leu Phe Thr
    450                 455                 460

Ser Asn Met Arg Ser Phe Ile His Tyr Ala Leu Ser Lys Tyr Pro Phe
465                 470                 475                 480

Ile Gly Val Pro Thr Pro Thr Leu Pro Glu Asn Glu Arg Leu Asn Glu
                485                 490                 495

Tyr Ala Asp Ser Phe Thr Asn Arg Phe Leu Asn His Tyr Pro Phe Ile
            500                 505                 510

His Val Thr Ile Leu Lys Glu Tyr Ser Leu Phe Lys Ala Ile Leu Asp
        515                 520                 525

Glu Asn Glu Ser Thr Lys Asn Trp Glu Asn Asn Gln Phe Tyr Leu Glu
    530                 535                 540
```

```
Asn Gln Arg Ile Ser Ile Val Cys Leu Pro Leu Leu Val Ala Thr Ile
545                 550                 555                 560

Gly Ala Val Leu Ser Asn Asn Lys Lys Asp Ala Ser Asn Leu Tyr Glu
                565                 570                 575

Ala Ser Arg Arg Cys Ile His Val Tyr Leu Asp Ser Arg Lys Lys Ile
            580                 585                 590

Pro Thr Ser Leu Ser Ala Asn Asn Asn Asp Ser Pro Leu Trp Leu Ile
        595                 600                 605

Gln Ser Leu Thr Leu Ser Val Met Tyr Gly Leu Phe Ala Asp Asn Asp
    610                 615                 620

Ile Ser Leu Asn Val Val Ile Arg Gln Val Asn Ala Leu Asn Ser Leu
625                 630                 635                 640

Val Lys Thr Ser Gly Leu Asn Arg Thr Ser Ile Ile Asp Leu Phe Asn
                645                 650                 655

Ile Asn Lys Pro Leu Asp Asn Glu Leu Trp Asn Gln Phe Val Lys Ile
            660                 665                 670

Glu Ser Thr Val Arg Thr Ile His Thr Ile Phe Gln Ile Ser Ser Asn
        675                 680                 685

Leu Ser Ala Leu Tyr Asn Ile Ile Pro Ser Leu Lys Ile Asp Asp Leu
    690                 695                 700

Met Ile Thr Leu Pro Val Pro Thr Thr Leu Trp Gln Ala Asp Ser Phe
705                 710                 715                 720

Val Lys Phe Lys Ser Leu Ser Tyr Gly Asn Gln Ile Pro Phe Gln Tyr
                725                 730                 735

Thr Arg Val Leu Gln Asn Leu Ile Asp Tyr Asn Gln Pro Leu Ser Asp
            740                 745                 750

Gly Lys Phe Leu Tyr Glu Asn His Val Ser Glu Phe Gly Leu Ile Cys
        755                 760                 765

Leu Gln Asn Gly Leu His Gln Tyr Ser Tyr Phe Gln Lys Leu Thr Ala
    770                 775                 780

Val Asn Asn Arg Glu Asp Ala Leu Phe Thr Lys Val Val Asn Ser Leu
785                 790                 795                 800

His Ser Trp Asp Arg Met Ile Ser Asn Ser Asp Leu Phe Pro Lys Lys
                805                 810                 815

Ile Tyr Gln Gln Ser Cys Leu Ile Leu Asp Ser Lys Leu Leu Asn Asn
            820                 825                 830

Phe Leu Ile Val Lys Ser Ser Leu Lys Val Ser Thr Gly Asp Val Ser
        835                 840                 845

Ser Leu Asn Lys Leu Lys Glu Asn Val Trp Leu Lys Asn Trp Asn Gln
    850                 855                 860

Val Cys Ala Ile Tyr Tyr Asn Ser Phe Met Asn Ile Pro Ala Pro Ser
865                 870                 875                 880

Ile Gln Lys Lys Tyr Asn Asp Ile Glu Phe Val Asp Asp Met Ile Asn
                885                 890                 895

Leu Ser Leu Ile Ile Lys Ile Met Lys Leu Ile Phe Tyr Asn Asn
            900                 905                 910

Val Lys Asp Asn Tyr Glu Asp Glu Asn Asp Phe Lys Leu Gln Glu Leu
        915                 920                 925

Asn Leu Thr Phe Asp Asn Phe Asp Glu Lys Ile Ser Leu Asn Leu Thr
    930                 935                 940

Ile Leu Phe Asp Ile Phe Leu Met Ile Tyr Lys Ile Ile Thr Asn Tyr
945                 950                 955                 960
```

```
Glu Lys Phe Met Lys Ile Lys His Lys Phe Asn Tyr Tyr Asn Ser Asn
            965                 970                 975

Ser Asn Ile Ser Phe Leu His His Phe Glu Leu Ser Ser Val Ile Asn
            980                 985                 990

Asn Thr Gln Met Asn Gln Asn Asp Tyr Met Lys Thr Asp Ile Asp Glu
            995                 1000                1005

Lys Leu Asp Gln Leu Phe His Ile Tyr Gln Thr Phe Phe Arg Leu
        1010                1015                1020

Tyr Leu Asp Leu Glu Lys Phe Met Lys Phe Lys Phe Asn Tyr His
        1025                1030                1035

Asp Phe Glu Thr Glu Phe Ser Ser Leu Ser Ile Ser Asn Ile Leu
        1040                1045                1050

Asn Thr His Ala Ala Ser Asn Asn Asp Thr Asn Ala Ala Asp Ala
        1055                1060                1065

Met Asn Ala Lys Asp Glu Lys Ile Ser Pro Thr Thr Leu Asn Ser
        1070                1075                1080

Val Leu Leu Ala Asp Glu Gly Asn Glu Asn Ser Gly Arg Asn Asn
        1085                1090                1095

Asp Ser Asp Arg Leu Phe Met Leu Asn Glu Leu Ile Asn Phe Glu
        1100                1105                1110

Val Gly Leu Lys Phe Leu Lys Ile Gly Glu Ser Phe Phe Asp Phe
        1115                1120                1125

Leu Tyr Glu Asn Asn Tyr Lys Phe Ile His Phe Lys Asn Leu Asn
        1130                1135                1140

Asp Gly Met Phe His Ile Arg Ile Tyr Leu Glu Asn Arg Leu Asp
        1145                1150                1155

Gly Gly Val
        1160

<210> SEQ ID NO 3
<211> LENGTH: 438
<212> TYPE: DNA
<213> ORGANISM: Artificial Sequence
<220> FEATURE:
<223> OTHER INFORMATION: Glycine max leghemoglobin codon-optimized for
      Pichia pastoris

<400> SEQUENCE: 3
atgggtgctt tcaccgagaa gcaggaagca cttgtttcct cttcgttcga agcttttaag      60
gctaacatcc ctcaatactc tgttgtgttt tacacgtcca ttctagaaaa agctcctgct     120
gccaaggacc tcttctcttt tctgtccaac ggtgtagatc catccaatcc caaattaaca     180
ggtcacgctg agaaattgtt cggtttagtc agagatagcg ctggacaatt gaaagcaaat     240
ggtactgtgg ttgctgatgc tgccttgggc agcatccatg cacagaaggc aattacagac     300
ccacaatttg ttgttgtgaa ggaagctctg cttaaaacta aaggaagc cgtcggagac       360 aaatggagtg acgagttgtc atcagcttgg gaggtagctt atgatgagtt ggccgcagca     420
atcaaaaagg cattctaa                                                   438

<210> SEQ ID NO 4
<211> LENGTH: 145
<212> TYPE: PRT
<213> ORGANISM: Artificial Sequence
<220> FEATURE:
<223> OTHER INFORMATION: Glycine max leghemoglobin codon-optimized for
      Pichia pastoris

<400> SEQUENCE: 4
```

```
Met Gly Ala Phe Thr Glu Lys Gln Glu Ala Leu Val Ser Ser Ser Phe
1               5                   10                  15

Glu Ala Phe Lys Ala Asn Ile Pro Gln Tyr Ser Val Val Phe Tyr Thr
                20                  25                  30

Ser Ile Leu Glu Lys Ala Pro Ala Ala Lys Asp Leu Phe Ser Phe Leu
            35                  40                  45

Ser Asn Gly Val Asp Pro Ser Asn Pro Lys Leu Thr Gly His Ala Glu
        50                  55                  60

Lys Leu Phe Gly Leu Val Arg Asp Ser Ala Gly Gln Leu Lys Ala Asn
65                  70                  75                  80

Gly Thr Val Val Ala Asp Ala Ala Leu Gly Ser Ile His Ala Gln Lys
                85                  90                  95

Ala Ile Thr Asp Pro Gln Phe Val Val Val Lys Glu Ala Leu Leu Lys
            100                 105                 110

Thr Ile Lys Glu Ala Val Gly Asp Lys Trp Ser Asp Glu Leu Ser Ser
        115                 120                 125

Ala Trp Glu Val Ala Tyr Asp Glu Leu Ala Ala Ile Lys Lys Ala
    130                 135                 140

Phe
145

<210> SEQ ID NO 5
<211> LENGTH: 438
<212> TYPE: DNA
<213> ORGANISM: Artificial Sequence
<220> FEATURE:
<223> OTHER INFORMATION: Glycine max leghemoglobin codon-optimized for
      Pichia pastoris

<400> SEQUENCE: 5
atgggtgcat ttacagaaaa acaagaggct ttagtatcct catcttttga agctttcaaa      60
gccaatattc tcaatactc cgttgttttc tatacgtcca ttttggaaaa ggctccagca     120
gctaaggacc ttttctcttt cttgtcgaac ggcgtggatc cctcaaatcc taagctgact     180
ggtcacgccg agaagctttt tggtttggtc agagacagcg ccggacagct gaaagctaac     240
ggtacagttg tggcagatgc tgccttggga tctatacatg cacaaaaggc tatcaccgac     300
ccacagtttg tggttgtaaa agaggctcta ctcaaaacta tcaaggaagc agttggtgac     360
aaatggagcg atgaattgtc cagtgcatgg gaggtcgctt acgatgagtt agctgctgca     420
atcaaaaagg cttttctaa                                                  438

<210> SEQ ID NO 6
<211> LENGTH: 145
<212> TYPE: PRT
<213> ORGANISM: Artificial Sequence
<220> FEATURE:
<223> OTHER INFORMATION: Glycine max leghemoglobin codon-optimized for
      Pichia pastoris

<400> SEQUENCE: 6

Met Gly Ala Phe Thr Glu Lys Gln Glu Ala Leu Val Ser Ser Ser Phe
1               5                   10                  15

Glu Ala Phe Lys Ala Asn Ile Pro Gln Tyr Ser Val Val Phe Tyr Thr
                20                  25                  30

Ser Ile Leu Glu Lys Ala Pro Ala Ala Lys Asp Leu Phe Ser Phe Leu
            35                  40                  45

Ser Asn Gly Val Asp Pro Ser Asn Pro Lys Leu Thr Gly His Ala Glu
```

```
            50                  55                  60
Lys Leu Phe Gly Leu Val Arg Asp Ser Ala Gly Gln Leu Lys Ala Asn
 65                  70                  75                  80

Gly Thr Val Val Ala Asp Ala Ala Leu Gly Ser Ile His Ala Gln Lys
                 85                  90                  95

Ala Ile Thr Asp Pro Gln Phe Val Val Lys Glu Ala Leu Leu Lys
            100                 105                 110

Thr Ile Lys Glu Ala Val Gly Asp Lys Trp Ser Asp Glu Leu Ser Ser
        115                 120                 125

Ala Trp Glu Val Ala Tyr Asp Glu Leu Ala Ala Ile Lys Lys Ala
    130                 135                 140

Phe
145

<210> SEQ ID NO 7
<211> LENGTH: 939
<212> TYPE: DNA
<213> ORGANISM: Pichia pastoris

<400> SEQUENCE: 7
gatctaacat ccaaagacga aaggttgaat gaaacctttt tgccatccga catccacagg      60
tccattctca cacataagtg ccaaacgcaa caggagggga tacactagca gcagaccgtt     120
gcaaacgcag gacctccact cctcttctcc tcaacaccca cttttgccat cgaaaaacca     180
gcccagttat tgggcttgat tggagctcgc tcattccaat tccttctatt aggctactaa     240
caccatgact ttattagcct gtctatcctg gccccctgg cgaggttcat gtttgtttat      300
ttccgaatgc aacaagctcc gcattacacc cgaacatcac tccagatgag gctttctga     360 gtgtggggtc aaatagtttc atgttcccca aatgggccaa aactgacagt ttaaacgctg     420
tcttggaacc taatatgaca aaagcgtgat ctcatccaag atgaactaag tttggttcgt     480
tgaaatgcta acggccagtt ggtcaaaaag aaacttccaa aagtcggcat accgtttgtc     540
ttgtttggta ttgattgacg aatgctcaaa ataatctca ttaatgctta gcgcagtctc      600
tctatcgctt ctgaaccccg gtgcacctgt gccgaaacgc aaatgggaa acacccgctt      660 tttggatgat tatgcattgt ctccacattg tatgcttcca agattctggt gggaatactg     720
ctgatagcct aacgttcatg atcaaaattt aactgttcta ccccctactt gacagcaata     780
tataaacaga aggaagctgc cctgtcttaa accttttttt ttatcatcat tattagctta     840
ctttcataat tgcgactggt tccaattgac aagcttttga ttttaacgac ttttaacgac     900
aacttgagaa gatcaaaaaa caactaatta ttcgaaacg                            939

<210> SEQ ID NO 8
<211> LENGTH: 558
<212> TYPE: DNA
<213> ORGANISM: Pichia pastoris

<400> SEQUENCE: 8
cgactattat cgatcaatga aatccatcaa gattgaaatc ttaaaattgc ccctttcact      60
tgacaggatc cttttttgta gaaatgtctt ggtgtcctcg tccaatcagg tagccatctc     120
tgaaatatct ggctccgttg caactccgaa cgacctgctg gcaacgtaaa attctccggg     180
gtaaaactta aatgtggagt aatggaacca gaaacgtctc ttcccttctc tctccttcca     240
ccgcccgtta ccgtccctag gaaatttac tctgctggag agcttcttct acggccccct      300
tgcagcaatg ctcttcccag cattacgttg cgggtaaaac ggaggtcgtg tacccgacct     360
```

| | | |
|---|---|---|
| agcagcccag ggatggaaaa gtcccggccg tcgctggcaa taatagcggg cggacgcatg | 420 | |
| tcatgagatt attggaaacc accagaatcg aatataaaag gcgaacacct ttcccaattt | 480 | |
| tggtttctcc tgacccaaag actttaaatt taatttattt gtccctattt caatcaattg | 540 | |
| aacaactatc aaaacacg | 558 | |

```
<210> SEQ ID NO 9
<211> LENGTH: 822
<212> TYPE: DNA
<213> ORGANISM: Pichia pastoris

<400> SEQUENCE: 9
```

| | |
|---|---|
| caggtgaacc cacctaacta tttttaactg ggatccagtg agctcgctgg gtgaaagcca | 60 |
| accatctttt gtttcgggga accgtgctcg ccccgtaaag ttaatttttt tttcccgcgc | 120 |
| agctttaatc tttcggcaga gaaggcgttt tcatcgtagc gtgggaacag aataatcagt | 180 |
| tcatgtgcta tacaggcaca tggcagcagt cactattttg cttttaacc ttaaagtcgt | 240 |
| tcatcaatca ttaactgacc aatcagattt tttgcatttg ccacttatct aaaaatactt | 300 |
| ttgtatctcg cagatacgtt cagtggtttc caggacaaca cccaaaaaaa ggtatcaatg | 360 |
| ccactaggca gtcggtttta ttttggtca cccacgcaaa gaagcaccca cctctttag | 420 |
| gttttaagtt gtgggaacag taacaccgcc tagagcttca ggaaaaacca gtacctgtga | 480 |
| ccgcaattca ccatgatgca gaatgttaat ttaaacgagt gccaaatcaa gatttcaaca | 540 |
| gacaaatcaa tcgatccata gttacccatt ccagcctttt cgtcgtcgag cctgcttcat | 600 |
| tcctgcctca ggtgcataac tttgcatgaa aagtccagat tagggcagat tttgagttta | 660 |
| aaataggaaa tataaacaaa tataccgcga aaaaggtttg tttatagctt ttcgcctggt | 720 |
| gccgtacggt ataaatacat actctcctcc cccccctggt tctcttttc ttttgttact | 780 |
| tacattttac cgttccgtca ctcgcttcac tcaacaacaa aa | 822 |

```
<210> SEQ ID NO 10
<211> LENGTH: 424
<212> TYPE: DNA
<213> ORGANISM: Pichia pastoris

<400> SEQUENCE: 10
```

| | |
|---|---|
| ataactgtcg cctcttttat ctgccgcact gcatgaggtg tccccttagt gggaaagagt | 60 |
| actgagccaa ccctggagga cagcaaggga aaaataccta caacttgctt cataatggtc | 120 |
| gtaaaacaa tccttgtcgg atataagtgt tgtagactgt cccttatcct ctgcgatgtt | 180 |
| cttcctctca agtttgcga tttctctcta tcagaattgc catcaagaga ctcaggacta | 240 |
| atttcgcagt cccacacgca ctcgtacatg attggctgaa attccctaa agaatttctt | 300 |
| tttcacgaaa attttttttt tacacaagat tttcagcaga tataaaatgg agagcaggac | 360 |
| ctccgctgtg actcttcttt tttttctttt attctcacta catacatttt agttattcgc | 420 |
| caac | 424 |

```
<210> SEQ ID NO 11
<211> LENGTH: 1683
<212> TYPE: DNA
<213> ORGANISM: Pichia pastoris

<400> SEQUENCE: 11
```

| | |
|---|---|
| atggagtttg tcgcccgtca gtccatgaat gcctgtccct tgtcaggtc aacttctacc | 60 |

-continued

| | |
|---|---|
| caccatttga agaagttggc agcaaacagt tctctagctg ctactgctag tcattgtccc | 120 |
| gtggttggcc ctgctctcca acagcagaga tactactctc aaccttccaa gccagcccaa | 180 |
| gcccaaacct ccgacattgc tactgggatc aagaaggatg tttctccgat ccgtatggac | 240 |
| tctaatgaaa ccgcctttga ttacaatgga atgtatgagt ctgatcttgc gaataaacgt | 300 |
| aaagataact cgtatcgtta tttcaataac atcaaccgtc tagccaagga gtttcccaag | 360 |
| gcacatcgcc agaccgaaga tgacaaggtg accgtctggt gctctaacga ctacttagga | 420 |
| atgggtaggc atcctgagat tatcaaaacc atgaaggcta ccatggacaa gtacggttcc | 480 |
| ggagcaggag gaactaggaa cattgcaggt cataaccacg ccgctatcaa tttggaaagc | 540 |
| gagttggctt gcttgaacaa gaaggaagcg gctctggtgt tttcatcatg tttcatagct | 600 |
| aacgatgcaa tcatctcgtt gttgggacaa aaaatcaaaa atttggtcat tttctctgac | 660 |
| cagtcgaatc atgcttccat gatattgggt gtgcgtaact ccaaagcgaa gaagcacatc | 720 |
| ttcaagcaca acaatttgaa ggatctggag tcgcagttag ctcagtaccc caagtcgact | 780 |
| cctaaactga tcgccttcga gtcagtttac tctatgtgtg gatctgtggc tcccattgag | 840 |
| aagatttgcg atttggctaa aaggtacggt gccctcacct tcttggatga agttcatgct | 900 |
| gttggaatgt atggtcctca tggacagggt gtagctgagc atttggactt tgatctgcat | 960 |
| ttacagtctg gaatcgccag tcctagcgtg gtggacaaac gcaccatatt ggatcgtgtc | 1020 |
| gacatgatta ctggtacttg cggaaagtca tttggtactt ttggaggtta cgttgctggt | 1080 |
| agtgccaacc taattgattg gttaagatcc tatgcgccag gtttcatttt cactaccaca | 1140 |
| cttcctcctg ctatcatggc tggtacagcc acttctgttc gtattgttag ggccgacatt | 1200 |
| gaggcccgta tcaagcaaca gcttaatact cgctacgtca agactcatt tgaaaacctt | 1260 |
| ggtattccag tcattccaaa cccaagtcac attgttcctg ttctagttgg aaatgctgca | 1320 |
| gatgccaaga aggcatccga tatgttaatg aacaaacacc gtatttatgt tcaagctatt | 1380 |
| aactacccta ctgtgcctgt cggtgaagaa cgactaagga ttactcctac tccaggtcat | 1440 |
| ggaaaggaga tttgtgacca gctgatcagc gctgtcgacg atgttttac tgagcttaat | 1500 |
| ttaccaagaa tcaacaaatg gcagtcccaa ggtggtcatt gcggtgttgg tgatgctaat | 1560 |
| tacgtaccag aacccaatct gtggactcag gaccagctca gcttgacaaa ccaagacttg | 1620 |
| cactccaatg tgcacaaccc agtgattgag cagatcgaaa cctcatcagg agtcagattg | 1680 |
| tag | 1683 |

<210> SEQ ID NO 12
<211> LENGTH: 1026
<212> TYPE: DNA
<213> ORGANISM: Pichia pastoris

<400> SEQUENCE: 12

| | |
|---|---|
| atggtgcata aggctgaata cttggacgac cacccaactc agatttccag cattctttca | 60 |
| ggaggttaca accacccatt acttcgtgaa tggcaacatg aacgtcaact caacaaaaac | 120 |
| atgttcatct ttccctgtt tgtcacagat cgaccagacg aagaagaact tattcctagt | 180 |
| ctacctaata tcaagaggtt tggcgttaac aagttgattc cttatgtagg aggtttggtt | 240 |
| tccaaaggat tgagggcggt gatcctattt ggtgttcctc tgaagcccgg tgtgaaagat | 300 |
| gaagaaggaa cggccgctga tgatccagag ggacctgtta tccaagccat caaacacttg | 360 |
| agaaagaact ttcctgacct gtatatcatc accgatgtct gtctatgtga gtacaccagc | 420 |
| catggacatt gtggaatact atatgaggat ggcactatca acagagagct ctcagtccgt | 480 |

```
cgtattgctg ctgtagctgt caaatatgct caagctggag ccaactctgt ggctccttct     540
gatatgactg acggcagaat aagagatatt aagaaggct tactaagtgc aggactggca     600
cataaaacgt ttgttatgtc ctacgctgca aaattctctg gtaatttgta tggccctttc    660
agagatgctg caggttcctg tccatctcaa ggggacagaa aatgttacca gcttccttct    720
ggaggaaaag ggttggccca tcgtgctctg attcgtgata tgaatgaagg cactgatgga    780
attattgtca aaccatctac attctatttg gacattgtcg ctgatgctta tcagctttgt    840
aaagactatc ctatctgctg ttaccaggtt tctggagagt acgccatgct acatgcagcg    900
gcagagaaga atattgttga tctgaaatca atcgcttttg aagctcatca aggattcttg    960
cgggctggag ctcgtttaat cattagttac tttaccccctg aattcctgga gtggttatct    1020
gaatga                                                              1026

<210> SEQ ID NO 13
<211> LENGTH: 1035
<212> TYPE: DNA
<213> ORGANISM: Pichia pastoris

<400> SEQUENCE: 13
atgaaccaaa tcgaacagag cggacccatt gattgcagtt ccttgaaatt ggggtcccga     60
aagtccgctc tggctataat ccaggcagaa atcgtccgcc aattgatatt gaaagaatac    120
cctgaattgg agacgaagtt ggtcagtgtg tccacccctg gggaccaagt ccagaataaa    180
gcacttttca cgtttggagg aaaatctttg tggaccaaag aacttgagat gttgttgttg    240
gagagtgtgg gaggatttga ccaaatagac atgattgtac actcgttgaa agacatgcca    300
actcatttac cagacgaatt tgagctgggt tgcattattg aaagagaaga ccctagagac    360
gctttggtcg tgcaagatgg tttatcttac aagtcattgg ccgaccttcc agagggagct    420
gtggtcggta cgtcttcggt tagaagatcg gctcaactac tgaagaattt ccctcatctg    480
aaattcaaat ctgttagagg aaaccttcag accagactaa gaaaattaga tgatccagat    540
tccgagtact gctgtctcct ccttgcagca gccggtttaa tcaggacagg cttacaacac    600
agaatttcaa tgtatttgaa cgacgatgtg atgtaccact ccgtcggaca aggagcatta    660
ggagtagaga tcagaaaagg tgaccaattc atgaaaaata tctgtgaaaa gattgggcat    720
agaaccacca cccttcgttg tcttgcagag agagcactgc tgagatatct agagggaggc    780
tgctcggtgc caattggggt ctccactatt tatagcgagg atacgaagga acttaccatg    840
aactccctag tcgtcagttg taacggtcgt gactcggtaa cagaatcaat gactgaagtc    900
gtgactactg aagagcaagc tgaagatttc ggtgaaaggc tggcccagaa gctcatagat    960
caaggtgcga aacgcattct tgacgagatc aacttcaaca agatcaaaga gattaaggaa   1020
gagggtttac attaa                                                    1035

<210> SEQ ID NO 14
<211> LENGTH: 798
<212> TYPE: DNA
<213> ORGANISM: Pichia pastoris

<400> SEQUENCE: 14
atgccaaaag ccattcttct gaagaataaa actacaccga aggatcctta tctggagaac     60
ttcgtaagta gtggctactc gaccgatttc gtaccacttt tagatcatat tcacatggag    120
aaatctgaga tcatcgcatt tctcaagact gactactttt gcataaaaac tttggcgttt    180
```

-continued

| | |
|---|---|
| attattacgt cccaaagagc tgtagaaatg ctgaatgagt gtatgcaaat actgagacgt | 240 |
| actgatcctg aaattacaca atcatctat agtaaacctg tctatacagt tggccctgcc | 300 |
| acctacagaa tacttgcgga tgctggcttc gtggatctac gaggcggaga taaggcagga | 360 |
| aacggatcca ttctagccca gataattttg aatgatgaca tttacactgg aattgaagat | 420 |
| tctgacaagc atataacgtt tttcacggga gaaacaagga gagacataat tcccaaatgt | 480 |
| ttactctcta acaactttca actttacgaa aagattgtct acaagactct tcctagggat | 540 |
| gatatcgtga ctagattcaa gtctgccgtt gacagcatcg accaatcgca aagaagttcc | 600 |
| agttgggtgg tcttcttttc gcctcaagga acagaggaca ttgtaacgta tcttcaacac | 660 |
| accaaagacc aatttaatat tgcatctatc gggccaacca cagaaaaata ccttctaagc | 720 |
| aaaaacctga aaccaaaagt tgtggcacct aagccagagc ctatctcttt actattgtct | 780 |
| atacaaaaag tgcactaa | 798 |

<210> SEQ ID NO 15
<211> LENGTH: 1086
<212> TYPE: DNA
<213> ORGANISM: Pichia pastoris

<400> SEQUENCE: 15

| | |
|---|---|
| atgagtagat ttccagaact gaagaatgac cttattttaa gggcagctcg tggtgaaaaa | 60 |
| gttgaacgtc ccccaatatg gattatgaga caggccggaa gatatcttcc ggagtaccat | 120 |
| gaggtcaaag gaggtaggga cttctttgaa acttgcaggg atgctgagat tgcttctgaa | 180 |
| attactatcc agccgattac gcattttgac ggtctgatcg atgcagctat tatcttcagt | 240 |
| gatatcttgg tgattcctca agctatgggc atggaagtta agatggtgga caaagttggc | 300 |
| ccacagttcc ccaatccgct aagaaaaccg tctgacttgg atcatttgaa aaagacgtt | 360 |
| gacgttttga aggaactcga ttgggccttc aaagctatct cattgaccag aaaaaaactc | 420 |
| aatgacgag tgcctttgct tggattttgt ggtgctcctt ggactctact ggtttatatg | 480 |
| actgaaggag gcggtaccaa gatgtttcga tttgcaaaag agtggatcta caagtttacc | 540 |
| aaggaatctc atcaattact ccaacagatc actgacgttg cagttgaatt cttagctcag | 600 |
| caagttgttg caggtgccca atgttacaa gttttttgaat cttggggcgg tgaattgggg | 660 |
| cctgatgaat tcgatgagtt ttcttttgcct tatttgagac agatttcctc taaacttccc | 720 |
| ctgaggttga aggaacttgg aatcacagag aatgttccca taactgtctt tgctaaaggc | 780 |
| tcttggtacg ccttggagca attgtgcgac agtggttatg atgttgtctc gttggattgg | 840 |
| ttattccgtc caagtgatgc tgtccagatt gctaacggaa gaatcgcatt gcaaggtaat | 900 |
| cttgaccctg gaaccatgta cggctccaaa gaaaccattt ccaagaaagt ggacaaaatg | 960 |
| atcaagggtt ttggtggagg aaagcaaaac tacataatta atttggaca cggcactcat | 1020 |
| ccattcatgg atccagaaca gatcagatgg ttcttacaag aatgtcatcg cattggatct | 1080 |
| caatag | 1086 |

<210> SEQ ID NO 16
<211> LENGTH: 978
<212> TYPE: DNA
<213> ORGANISM: Pichia pastoris

<400> SEQUENCE: 16

| | |
|---|---|
| atggccatcg actctgatat caatctaagc tctcccaatg attccatccg tcaaaggatg | 60 |
| ttcgagctta tccagcggaa gcaactcgaa attgtcgctg cattggaggc aattgaagga | 120 |

-continued

| | |
|---|---|
| aacgatacca aatttcgttc tgattcttgg gaaagaggag ccgaaggtgg aggaggaaga | 180 |
| tctatgctta ttcaagatgg aagagtgttt gaaaaggctg gtgtaaatat ttccaaggtt | 240 |
| catggcgtat tgcctcctca agctgtgagc cagatgagaa atgaccactc caagctagat | 300 |
| ctgcctgcgg gaacctctct gaagttcttt gcctgtgggc tttcgttggt cattcatccc | 360 |
| cataatcccc atgctccaac tacccatctg aattatcgct acttcgaaac ttgggatgaa | 420 |
| actgaaaagc ctcacacctg gtggtttggg ggcggtgctg atttaacgcc ttcgtacctg | 480 |
| tatcccgagg atgccaagca attccatcaa gcccataagg atgccctgga caaacacgat | 540 |
| gttagcttgt acccgagatt caaaaagtgg tgtgatgaat actttctgat caaacatcga | 600 |
| aatgaaacta gaggtattgg gggtattttc tttgatgatt ttgacgagtt tgatgctgag | 660 |
| aggtccctga agttggttga agattgtttc aatgctttct ggaatctta tcccgctatc | 720 |
| actcgaaaaa ggatggacac cccttcaact gatgctgaga agaactggca acaaattaga | 780 |
| agaggaagat atgtcgaatt caacttagta ttggatagag gtactcaatt tggtttgaga | 840 |
| acgcctggat ctcgtgttga agtatttttg atgtcgttgc caagaacagc tggttgggtc | 900 |
| tatgatcatc atccagagcc tggctccaga gaagaggagt tattgcaggt actacaaaat | 960 |
| cctattgaat gggtatga | 978 |

<210> SEQ ID NO 17
<211> LENGTH: 1683
<212> TYPE: DNA
<213> ORGANISM: Pichia pastoris

<400> SEQUENCE: 17

| | |
|---|---|
| atgctgaaaa gtcttgcacc aaattcctca attgccgttt taggttcagg gatatctgga | 60 |
| ttgactttca gcttttttttt gaatcggttg cgtcccgatg ttaagatcca tatctttgaa | 120 |
| aaatccaagc aggttggagg atggatcaga tcagaagagc atgaaacttt tcattttgaa | 180 |
| aagggaccca gaactttgag aggcacaaat acgggtacct tgatgttgtt ggatcttctt | 240 |
| accaagatag gagcaaatga caaggtcctg ggactgcaca agattctct tgctaataaa | 300 |
| aagtatctgt tgtccccgtt ctcagatgtt cacgaaaaca acgcaaagct tcttcaagtg | 360 |
| ccacaggatt tcagctcttt tgtaaagttc atgtttgacc cgttgtctaa ggatctcatt | 420 |
| ctcggtctttt tgaaagaacc atggcaacca aaattaaagt attcagatga gtcggttgac | 480 |
| catttttttca acagaagatt tgctaccaaa ctatcagaga atatcgtcag cgcaattgtg | 540 |
| catgaatct atgcgggcga cgtgaagaag ttaagtgtga agccatctt ccctaggctc | 600 |
| cctgagatgg aacaggaaag tggctctatt ataaggtata tgatcgccca atacaggaca | 660 |
| aaaaagaacg tcaaacaaaa agttgaccct tttttggcag attatgaaaa attgatcggt | 720 |
| acatctttga gtttcaaaaa tatttctttg tttctgaaaa actttcccat gctgagtttt | 780 |
| cagggtggac tacagaaact tcccatctca ttgaagaacc atttatcaca gattgaaaac | 840 |
| atcaagtttc atttttgacag caaaatcaaa acattgctt tggagagcgg taaggtggca | 900 |
| ttgactgacc atgatcaggt ttatcttgtt gaccatgtga gatctaccat taataccaac | 960 |
| gaattggcca aaatcatttc acccgttgtt ccaagttcta ctaagaaaaa atccgttttc | 1020 |
| aaatccaaag cgaatggccc agggctggtc aaatgtttga gctggctaca ctatacaaat | 1080 |
| atactaatgt gcaacatttta tatacctaag cacgtctcaa aatctatcac cggatttgga | 1140 |
| tacttggttc ctcgatcaat gtcttctcag gcatccaaac ttctcggtgt catatttgac | 1200 |

```
tcagacatcg agactgcaat gactcctaat tttacagagg ccaacattac ggcgataaac    1260
agtaactctg catctcccaa gcaactccaa aagttttctg accaattcgt caataatgat    1320
ctccctaaat acaccaagtt gacgctaatg cttggaggtc attatctcaa gtcggaggca    1380
gacatgcccg gttccgcaga gagtaaacat gctgtcaagg cgattctgtc aaatcacctg    1440
aatattgatc tagatgagtt tgcatctttg ccagacttca agatggaaat caccaagatc    1500
cccaactgca ttccccaata tgaagttggg tatcttgatc tcaagagaaa ggttcagaat    1560
gcagcctcca aagagttcaa cgaccaaata agttttggag gcatggcatt tggtgatggt    1620
gtggggatcc ctgactgtgt ccagaatgca ttcaaagatt cggctaccct cagtggcatt    1680
taa                                                                 1683

<210> SEQ ID NO 18
<211> LENGTH: 1125
<212> TYPE: DNA
<213> ORGANISM: Pichia pastoris

<400> SEQUENCE: 18
atgcttaacc gtcgtttcca atctaccgtg tcctcgagtc tgaacaaggg cactggaata     60
gtgttcatga atatgggtgg tccctccact gtcaaggaaa cctatgactt tttatttcgt    120
cttttctcgg acggagattt aatcccgttt ggcagatttc agaacatcct ggcccgcttc    180
attgcaagta gaagaacacc caaaattgaa tcctactaca agctatcgg aggtgggtct    240 cctatccgaa agtggtctga ataccagagt tctaaactat gtgaaaaatt agacattatc    300
agtccacaat cggctcctca taagccttat gttgccttca gatacgctaa tcctctcact    360
gaagatactt tacaaaagat gaaaaatgat ggaattacta aggccattgc cttttctcaa    420
tatccgcaat ttagttattc aaccaccgga tcatcgatta acgaacttta caggcaatcg    480
aaaattttgg accctgatca atctattaaa tggacagtta tagatcgctg gcctgaccac    540
ccagccttag ttaaaacttt cgcagctcat atcaaagata ctctaaacag attcaaaact    600
gaaaatggac tgactgacac aaaagacgtc gtcctccaat tcagtgctca ttctttacca    660
atggatattg tcaataaagg agattcgtat cctgcagaag tcgcagcgag tgtctttgcc    720
attatgaaag aacttaactt ctcaaatcct tataaattaa cctggcaatc acaggttggc    780
ccaaagcctt ggctgggtgc tcaaactgaa aaaattacca agcagctagc atccagtgat    840
gttcctggag tcgttttggt tcctattgcc tttacctctg atcatattga actctccat    900 gaactggata ttgaactgat tcaagaacta cctaatcctt caaaagtaaa gcagttgaa    960 tcgttgaacg gagaccaaac tttcattgac tccttggcag aactagtgaa gagtcacatt   1020
gattcgaagg ttgtatttc caaccagttg ccattggatt ccatgctggg agtagtgtca   1080
gataattccc tcacagatcc aaaagagttt ttcagagccc attga                  1125

<210> SEQ ID NO 19
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 19
gagggtctcg gatggagttt gtcgcccgtc                                     30

<210> SEQ ID NO 20
<211> LENGTH: 34
```

```
<212> TYPE: DNA
<213> ORGANISM: Artificial Sequence
<220> FEATURE:
<223> OTHER INFORMATION: Synthetic oligonucleotide

<400> SEQUENCE: 20
gagggtctcg attacaatct gactcctgat gagg                              34

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
gagggtctcg gatggtgcat aaggctgaat acttg                             35

<210> SEQ ID NO 22
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 22
gagggtctcg attattcaga taaccactcc agg                               33

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 23
gagggtctcg gatgccaaaa gccattcttc tgaag                             35

<210> SEQ ID NO 24
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 24
gagggtctcg attagtgcac tttttgtata gac                               33

<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 25
gagggtctcg gatgagtaga tttccagaac tgaag                             35

<210> SEQ ID NO 26
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 26
```

```
gagggtctcg attattgaga tccaatgcg                                         29

<210> SEQ ID NO 27
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 27
gagggtctcg gatggccatc gactctgata tc                                     32

<210> SEQ ID NO 28
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 28
gagggtctcg attataccca ttcaatagga t                                      31

<210> SEQ ID NO 29
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 29
gagggtctcg gatgctgaaa agtcttgcac caaa                                   34

<210> SEQ ID NO 30
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 30
gagggtctcg attaaatgcc actgagggta gc                                     32

<210> SEQ ID NO 31
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 31
caatcgctag catccaacat ccaaagacga aagg                                   34

<210> SEQ ID NO 32
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 32
ggatagcatg caccttatca agatagctag aaatagaaat gg                          42

<210> SEQ ID NO 33
<211> LENGTH: 37
<212> TYPE: DNA
<213> ORGANISM: Artificial Sequence
```

```
<220> FEATURE:
<223> OTHER INFORMATION: Synthetic oligonucleotide

<400> SEQUENCE: 33
caatagcatg caacatccaa agacgaaagg ttgaatg                              37

<210> SEQ ID NO 34
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 34
catggtaccg gtaccttatc aagatagcta gaaatagaaa tgg                       43

<210> SEQ ID NO 35
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 35
caatcgctag catccaacat ccaaagacga agg                                  34

<210> SEQ ID NO 36
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 36
gatattgctc gagaccttat caagatagct agaaatagaa atg                       43

<210> SEQ ID NO 37
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 37
caatctcgag aacatccaaa gacgaaaggt tg                                   32

<210> SEQ ID NO 38
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 38
caaccatttc tatttctagc tatcttgata aggtcttaag tcca                      44

<210> SEQ ID NO 39
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 39
catggtaccg gtaccttatc aagatagcta gaaatagaaa tgg                       43
```

<210> SEQ ID NO 40
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 40
ttacttaagt ccaacatcca aagacgaaag gttg                                    34

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
tcacagacgc gttgaattgt cc                                                 22

<210> SEQ ID NO 42
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 42
ttgctcctca gcttagaaga actcgtccaa catcaagtg                               39

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
ttagtcttgc tcctcagctt agcc                                               24

<210> SEQ ID NO 44
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 44
tcacagacgc gttgaattgt cc                                                 22

<210> SEQ ID NO 45
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 45
ttttgcggcc gcatgagcaa tctaccccca acttttg                                 37

<210> SEQ ID NO 46
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 46
aaaagcggcc gcctagacac caccatctag tcggtt                                  36

<210> SEQ ID NO 47
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 47
actagatggt ggtgtctagt caagaggatg tcagaatgcc atttg                        45

<210> SEQ ID NO 48
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 48
tctgacatcc tcttgactag acaccaccat ctagtcggtt ttctag                       46

<210> SEQ ID NO 49
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 49
aaacgctgtc ttggaaccta atatgac                                            27

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
aaactgtcag ttttgggcca tttg                                               24

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
acgctgtctt ggaacctaat atgac                                              25

<210> SEQ ID NO 52
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 52
tacccattca ataggatttt gtagtacctg c                                       31

<210> SEQ ID NO 53

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
gagcttcttc tacggccccc                                                  20

<210> SEQ ID NO 54
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 54
tccagcagag taaaatttcc tagggac                                          27

<210> SEQ ID NO 55
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 55
ctcttttagg ttttaagttg tgggaacagt aaca                                  34

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
gtgggtgctt ctttgcgtgg                                                  20

<210> SEQ ID NO 57
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 57
agaattgcca tcaagagact caggact                                          27

<210> SEQ ID NO 58
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 58
gatagagaga aatcgcaaac tttgagagga ag                                    32
```